US012338268B2

(12) United States Patent
Frydman et al.

(10) Patent No.: US 12,338,268 B2
(45) Date of Patent: Jun. 24, 2025

(54) COMPOSITIONS AND METHODS FOR TREATING PROTEIN AGGREGATION-ASSOCIATED DISEASES

(71) Applicants: The Board of Trustees of the Leland Stanford Junior University, Stanford, CA (US); The University of Leeds, West Yorkshire (GB); University of Konstanz, Constance (DE)

(72) Inventors: Judith Frydman, Stanford, CA (US); Sheena E. Radford, Leeds (GB); Elke Deuerling, Constance (DE)

(73) Assignees: The Board of Trustees of the Leland Stanford Junior University, Stanford, CA (US); The University of Leeds, West Yorkshire (GB); University of Konstanz, Constance (DE)

(*) Notice: Subject to any disclaimer, the term of this patent is extended or adjusted under 35 U.S.C. 154(b) by 767 days.

(21) Appl. No.: 17/435,628

(22) PCT Filed: Mar. 4, 2020

(86) PCT No.: PCT/US2020/020905
§ 371 (c)(1),
(2) Date: Sep. 1, 2021

(87) PCT Pub. No.: WO2020/180938
PCT Pub. Date: Sep. 10, 2020

(65) Prior Publication Data
US 2022/0259273 A1 Aug. 18, 2022

Related U.S. Application Data

(60) Provisional application No. 62/814,172, filed on Mar. 5, 2019.

(51) Int. Cl.
| | |
|---|---|
| *A61K 38/00* | (2006.01) |
| *A61K 9/00* | (2006.01) |
| *A61K 47/69* | (2017.01) |
| *A61P 25/28* | (2006.01) |
| *C07K 14/47* | (2006.01) |
| *C07K 16/18* | (2006.01) |

(52) U.S. Cl.
CPC ............ *C07K 14/47* (2013.01); *A61K 9/0085* (2013.01); *A61K 47/6903* (2017.08); *A61K 47/6911* (2017.08); *A61P 25/28* (2018.01); *A61K 38/00* (2013.01)

(58) Field of Classification Search
CPC .......... A61K 38/00; A61K 47/6903; A61K 47/6911; A61K 9/0085; A61P 25/28; C07K 14/47; C07K 16/18; C07K 2319/00
See application file for complete search history.

(56) References Cited

U.S. PATENT DOCUMENTS

| | | | | |
|---|---|---|---|---|
| 7,816,491 | B2 * | 10/2010 | Trent | B82Y 10/00 977/773 |
| 9,260,717 | B2 | 2/2016 | Kim et al. | |
| 2003/0233675 | A1 * | 12/2003 | Cao | C12N 15/8247 536/23.6 |
| 2006/0199781 | A1 | 9/2006 | Rothman et al. | |
| 2007/0238182 | A1 * | 10/2007 | Gaiger | G01N 33/57426 435/325 |
| 2008/0234183 | A1 * | 9/2008 | Hallbrink | A61P 3/10 435/320.1 |

OTHER PUBLICATIONS

Shen et al. (2019) "Dual Role of Ribosome-Binding Domain of NAC as a Potent Suppressor of Protein Aggregation and Aging-Related Proteinopathies," Molecular Cell. 74:729-741.
Guo et al. (2014) "The nascent polypeptide-associated complex is essential for autophagic flux," Autophagy 10:1738-1748.
Kirstein-Miles et al. (2013) "The nascent polypeptide-associated complex is a key regulator of proteostasis," EMBO J. 32:1451-1468.
Martin et al. (2018) "Conformational flexibility within the nascent polypeptide-associated complex enables its interactions with structurally diverse client proteins," Journal of Biological Chemistry 293:8554-8568.
Joachimiak et al. (2014) "The structural basis of substrate recognition by the eukaryotic chaperonin TRiC/CCT," Cell 159:1042-1055.
Kakkar et al. (2016) "The S/T-Rich Motif in the DNAJB6 Chaperone Delays Polyglutamine Aggregation and the Onset of Disease in a Mouse Model," Mol Cell 62:272-283.
Wang et al. (2010) "Crystal structures of NAC domains of human nascent polypeptide-associated complex (NAC) and its alphaNAC subunit," Protein Cell 1:406-416.
Wang (1995) "NAC covers ribosome-associated nascent chains thereby forming a protective environment for regions of nascent chains just emerging from the peptidyl transferase center," J. Cell Biol. 130:519-528.
Wegrzyn et al. (2006) "A conserved motif is prerequisite for the interaction of NAC with ribosomal protein L23 and nascent chains," J Biol Chem 281:2847-2857.
Ott et al. (2015) "Functional Dissection of the Nascent Polypeptide-Associated Complex in *Saccharomyces cerevisiae*," PLoS One 10:e0143457.

(Continued)

*Primary Examiner* — Julie Ha
(74) *Attorney, Agent, or Firm* — Jenny L. Buchbinder; Bozicevic, Field & Francis LLP

(57) ABSTRACT

Compositions and methods for treating aggregation-associated diseases are disclosed. In particular, compositions comprising the nascent polypeptide-associated complex (NAC) and the apical domain of CCT1 as well as peptide fragments thereof and fusion proteins containing NAC and CCT1 peptides can be used to suppress pathological protein aggregation and are useful for treatment of diseases associated with polyQ aggregation, amyloid beta aggregation, and alpha-synuclein aggregation.

9 Claims, 57 Drawing Sheets

Specification includes a Sequence Listing.

(56) References Cited

OTHER PUBLICATIONS

Saunders et al. (2009) "Multi-domain misfolding: understanding the aggregation pathway of polyglutamine proteins," Protein Eng. Des. Sel. 22:447-451.

Scarff et al. (2015) "Examination of Ataxin-3 (atx-3) Aggregation by Structural Mass Spectrometry Techniques: A Rationale for Expedited Aggregation upon Polyglutamine (polyQ) Expansion," Mol Cell Proteomics 14:1241-1253.

Sontag et al. (2013) "Exogenous delivery of chaperonin subunit fragment ApiCCT1 modulates mutant Huntingtin cellular phenotypes," Proc. Natl. Acad. Sci. U.S.A. 110(8):3077-3082.

Zhao et al. (2016) "TRiC subunits enhance BDNF axonal transport and rescue striatal atrophy in Huntington's disease," Proc. Natl. Acad. Sci. U.S.A. 113(38):E5655-5664.

Sahl et al. (2016) "Delayed emergence of subdiffraction-sized mutant huntingtin fibrils following inclusion body formation," Q. Rev. Biophys. 49:e2.

Tam et al. (2006) "The chaperonin TRiC controls polyglutamine aggregation and toxicity through subunit-specific interactions," Nat Cell Biol. 8(10):1155-1162.

Tam et al. (2009) "The chaperonin TRIC blocks a huntingtin sequence element that promotes the conformational switch to aggregation," Nat Struct Mol Biol. 16(12):1279-1285.

Machida et al (2016) "Cell-free analysis of polyQ-dependent protein aggregation and its inhibition by chaperone proteins," J. Biotechnol. 239:1-8.

Pongtepaditep et al. (2012) "Polyglutamined expanded androgen receptor interacts with chaperonin CCT," Eur. J. Med. Genet. 55(11):599-604.

Kitamura et al. (2006) "Cytosolic chaperonin prevents polyglutamine toxicity with altering the aggregation state," Nat Cell Biol. 8(10):1163-1170.

Darrow et al. (2015) "Structural Mechanisms of Mutant Huntingtin Aggregation Suppression by the Synthetic Chaperonin-like CCT5 Complex Explained by Cryoelectron Tomography," J. Biol. Chem. 290(28):17451-17461.

Sot et al. (2017) "The chaperonin CCT inhibits assembly of α-synuclein amyloid fibrils by a specific, conformation-dependent interaction," Sci Rep. 7:40859.

\* cited by examiner i. *C. elegans* βNAC, N-term, pI: 11.17
MDSKAIAEKIKKLQAQQEKVKIGGKGTPRKKKVIKKTAA Human βNAC, N-term, pI: 11.61
MKETIMNQEKLAKLQAQVKIGGKGTARKKKVVKRTAT ii. Human αNAC, N-term, pI: 3.73
MPGEATETVPATEQELPQPQAETGSGTESDSDESVPELEEQDSTQATTQQAQLAAAAEIDEEPVSKAKQSRS

FIG. 5A

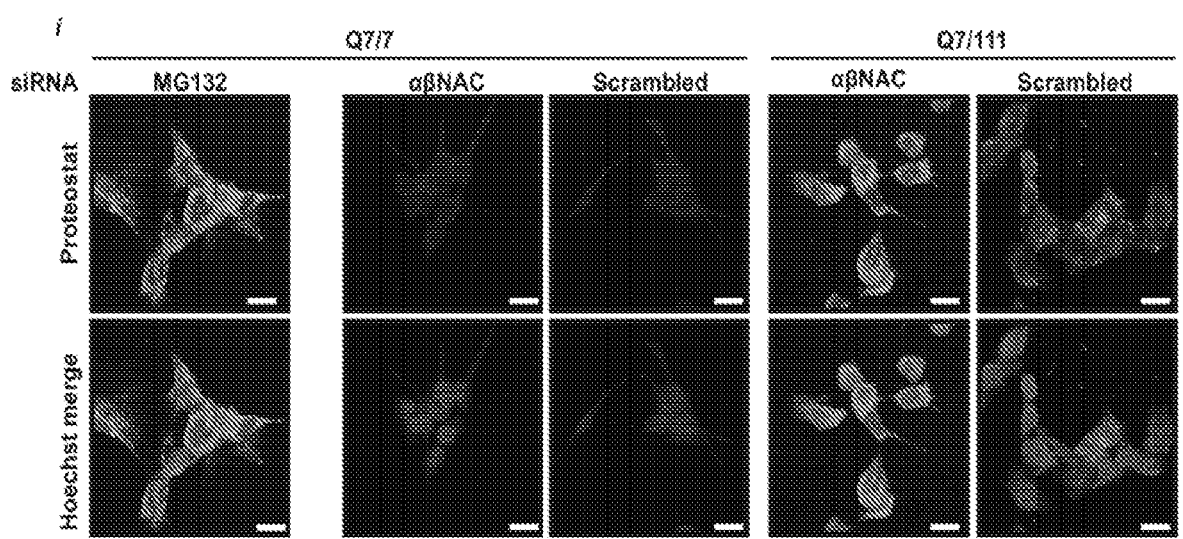
FIG. 6C1

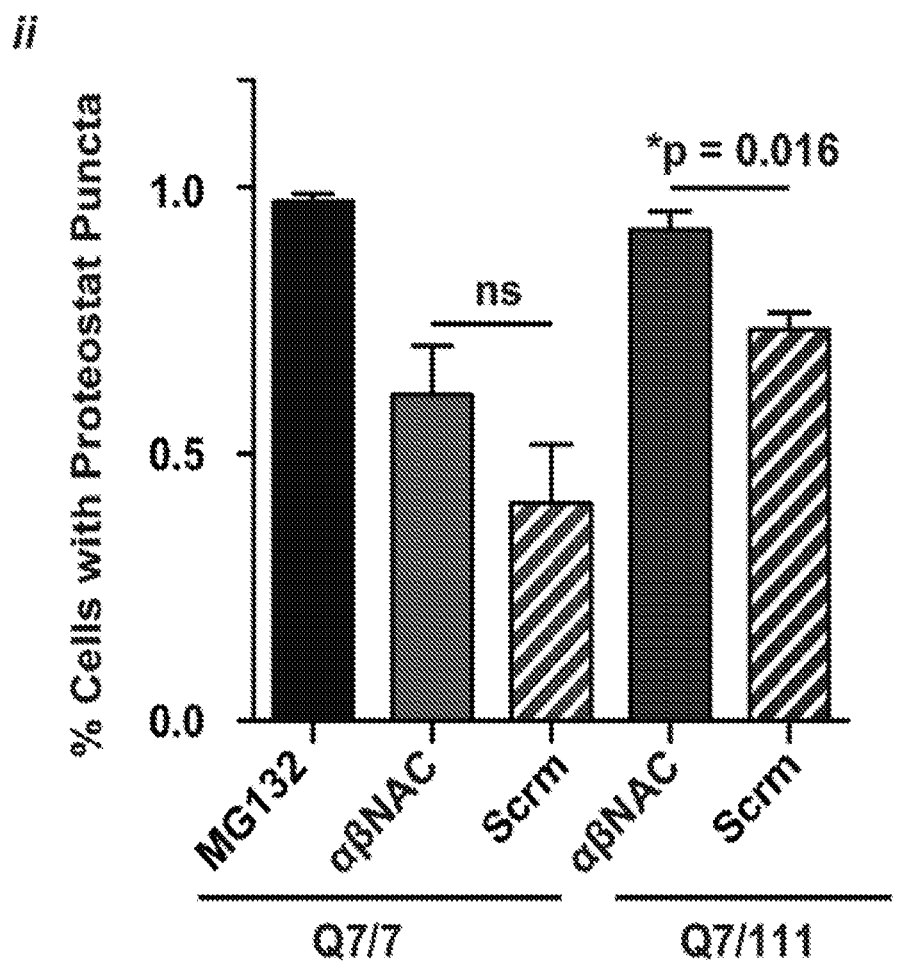
FIG. 6C2

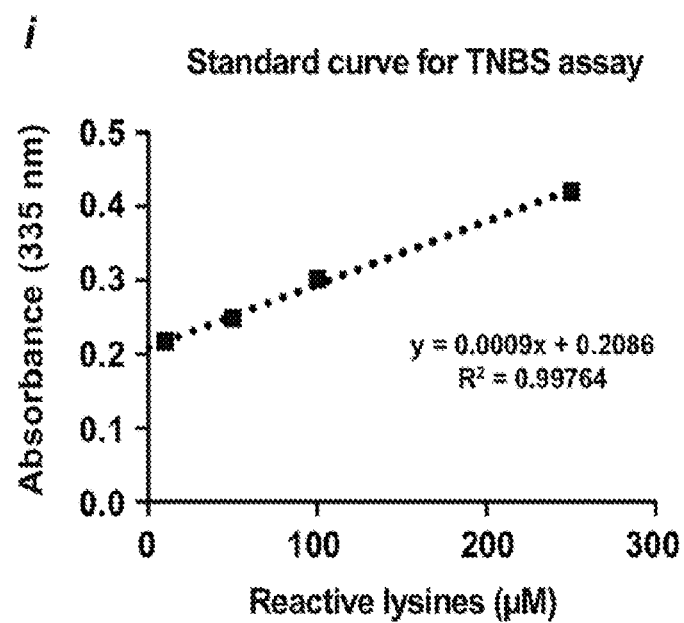
FIG. 13B1

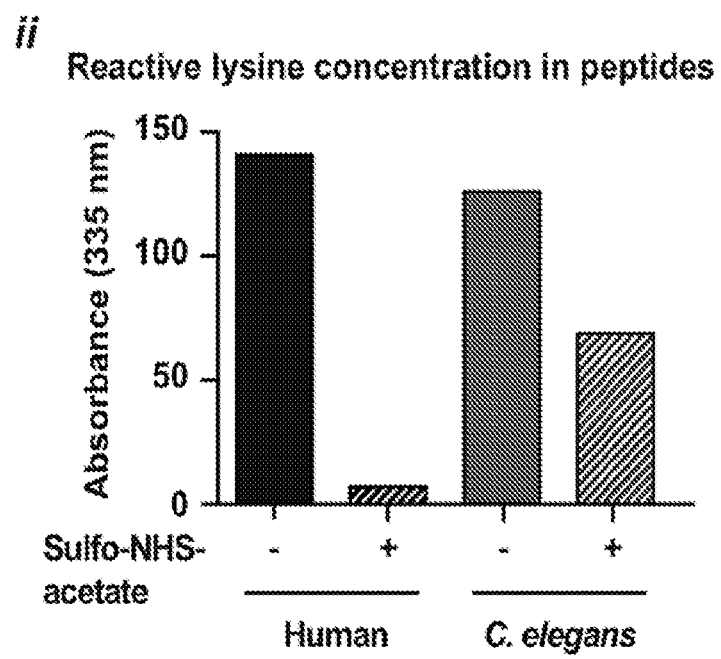
FIG. 13B2

COMPOSITIONS AND METHODS FOR TREATING PROTEIN AGGREGATION-ASSOCIATED DISEASES

STATEMENT REGARDING FEDERALLY SPONSORED RESEARCH OR DEVELOPMENT

This invention was made with Government support under contract NS092525 awarded by the National Institutes of Health. The Government has certain rights in the invention.

BACKGROUND

The frequency of late-onset neurodegenerative diseases is increasing due to the increased life expectancy of the general population in modern societies. These disorders, many of which are linked to aging, are caused by the accumulation of toxic protein aggregation species that are directly responsible for neuronal dysfunction and death. In many cases, such as Spinocerebellar Ataxia and Huntington's disease (HD), aggregation is associated with expanded polyglutamine (polyQ) tracts in the disease gene, usually beyond a critical threshold of approximately 40 or 35 glutamine repeats, respectively. It has become clear that accumulation of these aggregates is linked to the failure to eliminate misfolded and toxic forms of some proteins. As a defense mechanism against these toxic species, the cell deploys molecular chaperones which normally bind misfolded and non-native proteins and facilitate their folding or degradation. This machinery can also modulate aggregation and toxicity of these disease-associated proteins. Recent evidence has indicated that this machinery may become overburdened or less effective during the aging process, highlighting the importance to find ways to enhance or replace this protein folding machinery as therapeutics in these age-related diseases.

There remains a need for improved methods of treating patients having protein aggregation-associated diseases.

SUMMARY

The discovery that the nascent polypeptide-associated complex (NAC) and the apical domain of CCT1 as well as peptide fragments thereof and fusion proteins containing NAC and CCT1 peptides can be used to suppress pathological aggregation of polyQ and amyloid proteins provides the basis for the development of therapeutic methods and compositions. Thus, the present disclosure further pertains to compositions comprising NAC and CCT1 peptides, proteins, and fusion proteins and methods of using them for treatment of aggregation-associated diseases such as Huntington's disease and Spinocerebellar ataxia-3, associated with polyQ aggregation, Alzheimer's disease, associated with amyloid protein aggregation, and synucleinopathies such as Parkinson's disease, associated with alpha-synuclein.

In one aspect, an isolated peptide is provided comprising at least a portion of an N-terminal domain of a beta subunit of NAC, wherein the peptide suppresses aggregation of a protein comprising a polyglutamine (polyQ) sequence, for example, including, without limitation polyQ-expanded huntingtin exon1 or Ataxin-3.

In certain embodiments, the peptide comprises or consists of at least a C-terminal portion of the N-terminal domain corresponding to amino acid residues 23 to 38 numbered relative to the reference sequence of SEQ ID NO:1. In some embodiments, the peptide comprises the entire N-terminal domain.

In certain embodiments, the peptide comprises or consists of an amino acid sequence selected from the group consisting of SEQ ID NOS:1-3, or sequences displaying at least about 80-100% sequence identity thereto, including any percent identity within this range, such as 81, 82, 83, 84, 85, 86, 87, 88, 89, 90, 91, 92, 93, 94, 95, 96, 97, 98, 99% sequence identity thereto, wherein the peptide is capable of suppressing aggregation of a protein comprising a polyQ sequence.

In certain embodiments, the peptide further comprises a cell-penetrating peptide linked to said at least a portion of the N-terminal domain of the beta subunit of the NAC.

In another aspect, a fusion protein is provided comprising any of the NAC peptides described herein connected to a peptide comprising an apical domain of CCT1.

In certain embodiments, the apical domain of CCT1 comprises an amino acid sequence of SEQ ID NO:7, or a sequence displaying at least about 80-100% sequence identity thereto, including any percent identity within this range, such as 81, 82, 83, 84, 85, 86, 87, 88, 89, 90, 91, 92, 93, 94, 95, 96, 97, 98, 99% sequence identity thereto, wherein a fusion protein comprising the apical domain is capable of suppressing aggregation of a protein comprising a polyQ sequence, for example, including, without limitation, polyQ-expanded huntingtin exon1.

In certain embodiments, the fusion protein comprises or consists of an amino acid sequence of SEQ ID NO:8, or a sequence displaying at least about 80-100% sequence identity thereto, including any percent identity within this range, such as 81, 82, 83, 84, 85, 86, 87, 88, 89, 90, 91, 92, 93, 94, 95, 96, 97, 98, 99% sequence identity thereto, wherein the fusion protein suppresses aggregation of a protein comprising a polyQ sequence, for example including, without limitation, polyQ-expanded huntingtin exon1.

In certain embodiments, the fusion protein further comprises a linker (e.g., in between the NAC peptide and the CCT1 peptide).

In certain embodiments, the fusion protein further comprises a cell-penetrating peptide.

In another aspect, a composition for use in the treatment of an aggregation-associated disease is provided, the composition comprising a peptide comprising at least a portion of an N-terminal domain of a beta subunit of NAC or a fusion protein comprising a peptide comprising an apical domain of CCT1 connected to a peptide comprising at least a portion of an N-terminal domain of a beta subunit of NAC, as described herein. The composition may further comprise a pharmaceutically acceptable excipient. In certain embodiments, the composition further comprises a pharmaceutically acceptable carrier selected from the group consisting of a cream, emulsion, gel, liposome, nanoparticle, or ointment.

In another aspect, a method of treating a subject for an aggregation-associated disease is provided, the method comprising administering a therapeutically effective amount of a composition comprising a peptide comprising at least a portion of an N-terminal domain of a beta subunit of NAC or a fusion protein comprising a peptide comprising an apical domain of CCT1 connected to a peptide comprising at least a portion of an N-terminal domain of a beta subunit of NAC, as described herein, to the subject.

Exemplary polyQ aggregation-associated diseases include Huntington's disease, dentatorubropallidoluysian atrophy (DRPLA), spinal and bulbar muscular atrophy (SBMA), and spinocerebellar ataxia (SCA) including, but not limited to, SCA Type 1 (SCA1), SCA Type 2 (SCA2), SCA Type 3 (SCA3) or Machado-Joseph disease, SCA Type 6 (SCA6), SCA Type 7 (SCA7), and SCA Type 17 (SCA17).

In certain embodiments, the protein comprising the polyQ sequence is polyQ-expanded huntingtin exon1 or Ataxin-3.

The composition may be administered by any suitable mode of administration such as, but not limited to, intravenously, intra-arterially, intracerebroventricularly, or intralesionally. In one embodiment, the composition is administered intra-arterially into a blood supply of a lesion comprising a polyQ protein. In another embodiment, the composition is administered stereotactically into the brain of the subject. In a further embodiment, the composition is administered into the spinal cord or cerebrospinal fluid of the subject.

An effective amount of a composition comprising a peptide comprising at least a portion of an N-terminal domain of a beta subunit of NAC or a fusion protein comprising a peptide comprising an apical domain of CCT1 connected to a peptide comprising at least a portion of an N-terminal domain of a beta subunit of NAC, as described herein, can be administered to a subject in one or more administrations, applications or dosages. By "therapeutically effective dose or amount" is intended an amount that, when administered, as described herein, brings about a positive therapeutic response, such as improved neurological recovery from a polyQ aggregation-associated disease. Improved neurological recovery may include a reduction in polyQ protein aggregation, a reduction in insoluble polyQ protein aggregates in the nuclei of neurons, restored neuronal function, improved cognition, or improved memory. Additionally, a therapeutically effective dose or amount may retard loss of cerebellar Purkinje neurons and loss of brain cells.

In certain embodiments, multiple rounds of treatment are administered. The composition may be administered, for example, according to a daily dosing regimen or intermittently.

In another aspect, a method is provided for suppressing aggregation of a protein comprising a polyglutamine (polyQ) sequence in a subject, the method comprising administering a therapeutically effective amount of a composition comprising a peptide comprising at least a portion of an N-terminal domain of a beta subunit of NAC or a fusion protein comprising a peptide comprising an apical domain of CCT1 connected to a peptide comprising at least a portion of an N-terminal domain of a beta subunit of NAC, as described herein, to the subject.

In another aspect, a kit is provided comprising a composition comprising a peptide comprising at least a portion of an N-terminal domain of a beta subunit of NAC or a fusion protein comprising a peptide comprising an apical domain of CCT1 connected to a peptide comprising at least a portion of an N-terminal domain of a beta subunit of NAC, as described herein, and instructions for treating an aggregation-associated disease.

In another aspect, a composition for use in the treatment of Alzheimer's disease or a synucleinopathy is provided comprising a NAC protein. In one embodiment, the NAC protein is a human NAC protein. In another embodiment, the NAC protein comprises a deletion of an N-terminal domain of a beta subunit corresponding to amino acid residues 1 to 38 numbered relative to the reference sequence of SEQ ID NO:1. In certain embodiments, the composition further comprises a pharmaceutically acceptable excipient. In another embodiment, the composition further comprises a pharmaceutically acceptable carrier selected from the group consisting of a cream, emulsion, gel, liposome, nanoparticle, or ointment.

Exemplary synucleinopathies include Parkinson's disease, dementia with Lewy bodies, multiple system atrophy, and neuroaxonal dystrophies.

In another aspect, a method of treating a subject for Alzheimer's disease or a synucleinopathy is provided comprising administering a therapeutically effective amount of a composition comprising a NAC protein to the subject. The composition may be administered by any suitable mode of administration such as, but not limited to, intravenously, intra-arterially, intracerebroventricularly, or intralesionally. In one embodiment, the composition is administered intra-arterially into a blood supply of a lesion comprising an amyloid beta protein (e.g., Aβ40). In another embodiment, the composition is administered stereotactically into the brain of the subject. In a further embodiment, the composition is administered into the spinal cord or cerebrospinal fluid of the subject. In some embodiments, multiple rounds of treatment are administered to the subject. For example, the composition may be administered according to a daily dosing regimen or intermittently.

An effective amount of a composition comprising a NAC protein can be administered to a subject in one or more administrations, applications or dosages. By "therapeutically effective dose or amount" is intended an amount that, when administered, as described herein, brings about a positive therapeutic response, such as improved neurological recovery from Alzheimer's disease or a synucleinopathy. Improved neurological recovery may include a reduction in aggregation of amyloid beta or alpha-synuclein, a reduction in amyloid plaques, a reduction in Lewy bodies, restored neuronal function, improved cognition, or improved memory.

In another aspect, a method of suppressing aggregation of an amyloid beta peptide in a subject is provided, the method comprising administering an effective amount of a composition comprising a NAC protein to the subject. Amyloid beta (Aβ or Abeta) peptides include, but are not limited to, Aβ 36-43, which are components of amyloid plaques associated with Alzheimer's disease. In one embodiment, aggregation of one or more amyloid peptides selected from the group consisting of Aβ36, Aβ37, Aβ38, Aβ39, Aβ40, Aβ41, Aβ42, and Aβ43 is suppressed.

In another aspect, a method of suppressing aggregation of alpha-synuclein in a subject is provided, the method comprising administering an effective amount of a composition comprising a NAC protein to the subject.

The methods disclosed herein may be combined with other treatment regimens for treating an aggregation-associated disease.

BRIEF DESCRIPTION OF THE DRAWINGS

It is emphasized that, according to common practice, the various features of the drawings are not to-scale. On the contrary, the dimensions of the various features are arbitrarily expanded or reduced for clarity. Included in the drawings are the following figures.

(FIG. 1A) Fluorescence microscope images of PolyQ35::YFP *C. elegans* worms overexpressing NAC (FLAG-tagged α- and βNAC) in muscle cells. Images were taken at day 3 of adulthood. Scalebar=500 μm in whole body images and 50 μm in images showing the head region. PolyQ35::YFP aggregates and cell nuclei are indicated by white and blue arrowheads, respectively. ev=empty vector. (FIG. 1B) PolyQ35::YFP aggregation in animals as in (FIG. 1A) was further assessed by semi-denaturing agarose gel electrophoresis (SDD-AGE) immunoblot analysis. Total levels of SDS-soluble PolyQ35::YFP and FLAG-tagged NAC subunits were assessed by denaturing SDS-PAGE immunoblot analysis. Actin served as loading control. See also FIG. 7A. (FIG. 1C) Filter trap aggregation assay of PolyQ51 peptide incubated with 5× molar excess of human NAC in vitro. Aggregation of GST-PolyQ51 was initiated by cleavage of the GST tag using the TEV protease. SDS-insoluble aggregates were detected with an S-tag antibody. (FIG. 1D) Quantification of SDS-insoluble PolyQ51 aggregates obtained in filter trap from (FIG. 1C). Data is representative of at least 3 independent biological replicates. (FIG. 1E) Filter trap aggregation assay of mutant Huntingtin (mHttQ51) incubated with 5× molar excess of human NAC or ovalbumin control (Ova) in vitro. Aggregation of GST-mHttQ51 was initiated by cleavage of the GST tag using the TEV protease. SDS-insoluble aggregates were detected with an S-tag antibody. (FIG. 1F) Quantification of SDS-insoluble mHttQ51 aggregates obtained in filter trap from (FIG. 1E). Data is representative of at least 3 independent biological replicates.

(FIG. 2A) Filter trap aggregation assay of full-length Ataxin-3 containing a stretch of 78 glutamines (AtxQ78) incubated with 1×molar excess of NAC at 37° C. for the indicated time. SDS-insoluble aggregates were detected with an anti-His antibody. See also FIG. 8A. (FIG. 2B) Quantification of SDS-insoluble AtxQ78 aggregates obtained in filter trap from (FIG. 2A). Data is representative of at least 3 independent biological replicates. (FIG. 2C) NAC and AtxQ78 were incubated in a 1:1 molar ratio and crosslinked using the homobifunctional crosslinker $BS^3$. The schematic shows all intermolecular $BS^3$-crosslinks identified by MS analysis of NAC-AtxQ78 complexes excised from the gel shown in FIG. 8C.

(FIG. 3A) Schematics showing the different heterodimeric NAC variants (α- and β-subunit) investigated in (FIGS. 3C-3E). Conserved domains (NAC and UBA) as well as the conserved ribosome binding motif (RRKxxKK) in the β-subunit are highlighted. (FIG. 3B) Sucrose density gradient analysis in wildtype N2 worms on day 2 of adulthood. Upper image shows polysome gradient profile (absorbance at 254 nm). Immunoblot images below show the distribution of NAC (α- and β-subunit) throughout the gradient. uL16 served as a ribosomal marker. (FIG. 3C) Fluorescence microscope images of PolyQ35::YFP worms overexpressing WT-NAC or different mutant NAC versions shown in (A). Images were taken at day 3 of adulthood. Scalebar=500 μm (upper row) and 50 μm (lower row). PolyQ35::YFP aggregates and cell nuclei are indicated by white and blue arrowheads, respectively. ev=empty vector. (FIG. 3D) SDD-AGE immunoblot showing the PolyQ35::YFP aggregation in animals as in (FIG. 3C). Total levels of SDS-soluble PolyQ35::YFP and FLAG-tagged NAC variants were assessed by SDS-PAGE immunoblot analysis. Actin served as loading control. (FIG. 3E) In vitro filter trap aggregation assay of mutant Huntingtin (mHttQ51) incubated with 5× molar excess of indicated NAC variants. Aggregation of GST-mHttQ51 was initiated by cleavage of the GST tag using the TEV protease. SDS-insoluble aggregates were detected with an S-tag antibody.

(FIG. 4A) In vitro chaperone refolding assays using guanidine-HCl (GdmCl)-denatured luciferase as substrate. Luciferase (0.02 μM) was preincubated with indicated NAC variants in a 1:1 molar ratio for 15 min at room temperature and refolding was initiated by adding an Hsp70/Hsp40 chaperone system (3.2 μM/0.8 μM). Luciferase reactivation was analyzed by luminescence recording over two hours at RT using luciferin as a substrate. Statistical significance was calculated by one-way ANOVA and Tukey post hoc test. a.u.=arbitrary units. *$p<0.05$. See also FIG. 11A-C. (FIG. 4B) Fluorescence microscope images of C. elegans worms expressing a destabilized variant of firefly luciferase fused to EGFP (FlucDM-EGFP) and indicated NAC variants (FLAG-tagged α and βNAC) in muscle cells. Images were taken before heat-shock (HS, 1 h at 33° C.), directly after HS, and after 24 h recovery at 20° C. Scalebar=20 μm. ev=empty vector. See also FIG. 11D. (FIG. 4C) Kinetic aggregation assays of Aβ40 (32 μM, blue) incubated with an equimolar concentration of WT-NAC (red) or ΔNαβ-NAC (yellow) measured using ThioflavinT fluorescence. a.u.=arbitrary units. See also FIG. 12C. (FIG. 4D) Negative stain transmission electron micrographs of the reaction endpoint (at 20 h) for each sample shown in (FIG. 4C). Scale bar=5 μm.

FIGS. 5A-5E show functional characterization of the N-terminal βNAC chaperone domain. (FIG. 5A) (i) Peptide sequences of N-termini of βNAC from C. elegans (SEQ ID NO:1) and humans (SEQ ID NO:2). Positively charged residues are highlighted in red. Both peptides exhibit a considerably high isoelectric point (pI). (ii) N-terminal peptide sequence of human αNAC (SEQ ID NO:4) exhibiting in contrast to βNAC peptides a low pI. Negatively charged residues are highlighted in blue. (FIG. 5B) In vitro filter trap aggregation assay of mutant Huntingtin (mHttQ51) incubated with 5× or 10× molar excess of βNAC peptides shown in (A) or full-length NAC protein. (FIG. 5C) (i) Chemical reaction scheme showing acylation of primary amines by Sulfo-NHS-acetate used to neutralize the positive charge in lysine residues of βNAC peptides shown in (FIG. 5A). (ii) In vitro filter trap aggregation assay of mutant Huntingtin (mHttQ51) incubated with 5× molar excess of peptides shown in (FIG. 5A) with and without Sulfo-NHS-acetate labeling. Labeling efficiency of peptides is shown in FIG. 13B, C. (FIG. 5D) In vitro filter trap aggregation assay of mutant Huntingtin (mHttQ51) incubated with 5× molar excess of full-length NAC protein (NAC), full N-terminal ρNAC peptide (Full N-term), or the N- and C-half of the peptide as indicated in the schematic below (SEQ ID NO:2). (FIG. 5E) In vitro filter trap aggregation assay of mutant Huntingtin (mHttQ51) incubated with 5× or 10× molar excess of human α- or βNAC peptides shown in (FIG. 5A). See also FIG. 13C.

FIGS. 6A-6D show that NAC suppresses toxicity of PolyQ proteins. (FIG. 6A) Viability of mouse striatal neurons either homozygous for wild-type Huntingtin (Q7/7) or heterozygous for mutant Huntingtin (Q7/111). Viability was measured using the Cell Titer Glo assay after 3-day treatment with siRNAs targeting both NAC subunits. Scrambled (Scrm) siRNA sequences were used as control. Data are represented as mean±SEM. Statistical significance was determined by Two-way ANOVA. Data is representative of at least 5 independent biological replicates. a.u.=arbitrary units. (FIG. 6B) Quantification of α/βNAC knockdown by qPCR in the mouse striatal cell lines Q7/7 and Q7/111. Actin was used as a housekeeping gene control. Knockdown of α/βNAC was compared to the scrambled control condition. (FIG. 6C) (I) Homozygous wild-type (Q7/7) and heterozygous mutant (Q7/111) Huntingtin cells were treated with NAC siRNA or a scrambled control (Scrm) for three days. Fluorescence microscope images show cells stained with Proteostat fluorescent dye to assess protein aggregation. Cells treated with the proteasome inhibitor MG132 (5 µM, 6 h) were used as positive aggregation control. Scale bar=15 µm. Hoechst was used to label nuclei of cells. (ii) Diagram shows the ratio of Proteostat fluorescence to Hoechst fluorescence in cells shown as in (i). Data are represented as mean±SEM and represents the average over 3 independent biological replicates. (FIG. 6D) Diagram shows the percentage of non-paralyzed PolyQ35::YFP *C. elegans* worms overexpressing either wild-type NAC (WT-NAC), ribosome-binding deficient NAC (RRK/AAA) or NAC lacking the N-terminal region of βNAC (ΔNβ-NAC) between day 6 and 10 of adulthood. Data are represented as mean±SEM. Statistical significance was calculated by Student's t test. *****$p<0.01/0.001$ vs. WT-NAC. EV=empty vector.

(FIG. 7A) Quantification of PolyQ35::YFP signal on SDD-AGE blots as shown in FIG. 1B. Data are represented as mean±SEM. Statistical significance was calculated by Student's t test. ev=empty vector. (FIG. 7B) In vitro filter trap aggregation assay of mutant Huntingtin (mHttQ51) incubated with 1×, 5× or 10× molar excess of human NAC. Aggregation of GST-mHttQ51 was initiated by cleavage of the GST tag using the TEV protease. SDS-insoluble aggregates were detected with an S-tag antibody. (FIG. 7C) Same assay as in (FIG. 7A) but with either human or *C. elegans* NAC added. (FIG. 7D) (i) Schematic of in vitro filter trap aggregation assay of mHttQ51. The experiment was conducted similarly to (FIG. 7A), with the exception of a 6-hour time delay between initiation of aggregation and addition of NAC or Ovalbumin control. (ii) SDS-insoluble aggregates of mHttQ51 after addition of 5× molar excess of NAC or ovalbumin (Ova) control. (iii) Quantification of SDS-insoluble aggregates shown in (ii).

(FIG. 8A) Filter trap aggregation assay of AtxQ78 incubated with an equimolar concentration of either human or *C. elegans* NAC at 37° C. for the indicated time. SDS-insoluble aggregates were detected with an anti-His antibody. (FIG. 8B) Schematic showing the domain architecture of Ataxin-3. All lysine residues carrying optimal functional groups for chemical crosslinking with amine-reactive crosslinkers are highlighted in red. Josephine domain, green. PolyQ78 stretch, blue. UIM=ubiquitin interacting motif. (FIG. 8C) Coomassie-stained Tris-Tricine gel showing crosslinked protein complexes. NAC and AtxQ78 were crosslinked either with 20× or 50× molar excess of BS3 for 1 hour. NAC and AtxQ78 alone were used as controls. New bands labeled with 1 (NAC-AtxQ78 monomer) and 2 (NAC-AtxQ78 dimer) were excised from the gel and subjected to an in-gel digest for the LC-MS analysis shown in FIG. 2C.

(FIG. 9A) Sucrose cushion centrifugation of ribosomes in PolyQ35::YFP *C. elegans* worms overexpressing either 3×FLAG-tagged WT- or RRK/AAA-NAC in muscle cells (myo-3 promoter). Analysis was performed on day 2 of adulthood. Indicated proteins in the supernatant (Soluble) and ribosomal pellet (Pellet) fractions were analyzed by immunoblotting. uL24 served as a ribosomal marker. (FIG. 9B) Immunoblot analysis of total levels of endogenous NAC (ubiquitous expression) and overexpressed 3×FLAG-tagged NAC variants in body wall muscles in animals investigated in FIGS. 3C, 3D. FLAG immunoblot shows only exogenously overexpressed NAC in muscle cells, while the αβNAC immunoblot shows endogenous and exogenous NAC variants, as indicated. Tubulin served as a loading control.

(FIG. 11A) In vitro luciferase refolding assays using guanidine-HCl (GdmCl)-denatured substrate. Luciferase (0.02 µM) was incubated with an equimolar concentration of human NAC in the presence and absence of an Hsp70/Hsp40 system (3.2 µM/0.8 µM). Luciferase reactivation was analyzed by luminescence recording over two hours at RT using luciferin as a substrate. a.u.=arbitrary units. (FIG. 11B) Similar assay as in (A) but luciferase was first preincubated with NAC or GFP control in a 1:1 molar ratio for 15 min at room temperature before adding the Hsp70/Hsp40 chaperone system. (FIG. 11C) Experiment was conducted similarly to (B) but with NAC from both human and *C. elegans*. (FIG. 11D) Immunoblot analysis of wild-type NAC and ΔNβ-NAC (FLAG-tagged α- and βNAC) overexpressed in FlucDM-EGFP strain. Tubulin served as loading control.

(FIG. 12A) Coomassie-stained gel showing isolated NAC-Aβ40 complexes crosslinked with BS$^3$. NAC and Aβ40 (both 18 µM) were incubated at 37° C. for two hours and crosslinked using 20× molar excess of BS3 for 30 min. Crosslinked samples were gel-filtrated and NAC-Aβ40 complexes immunoprecipitated using Aβ40 antibody (6E10). Proteins were eluted under non-reducing conditions to avoid antibody splitting into light and heavy chains. (FIG. 12B) Crosslinked NAC-Aβ40 complexes from gel were excised and subjected to an in-gel digest and LC-MS analysis. Schematic shows identified intermolecular crosslinks. See also Table 2. (FIG. 12C) Aβ40 aggregation (18 µM) was examined in the presence of molar equivalent *C. elegans* NAC constructs (18 µM) with 10 µM thioflavin T (ThT). Samples were incubated quiescently at 37° C. for 20 h. Each color indicates replicate assays prepared in the same plate. Aggregation results were baseline subtracted from NAC constructs alone (without Aβ40) or buffer, which did not show aggregation.

FIGS. 13A-13C show suppression of PolyQ aggregation by the βNAC N-terminus. (FIG. 13A) In vitro filter trap aggregation assay of PolyQ51 incubated with 5× molar excess of either *C. elegans* NAC, human NAC or the human N-terminal βNAC peptide. Aggregation of GST-PolyQ51 was initiated by cleavage of the GST tag using the TEV protease. SDS-insoluble aggregates were detected with an S-tag antibody. (FIG. 13B) Quantification of sulfo-NHS-acetate labeling of lysine residues in βNAC N-terminal peptides using the TNBS assay to assess amounts of primary amines. (i) Standard curve of lysine amino acid with 335 nm absorbance levels. (ii) Quantification of primary amine availability with differently treated peptides. (FIG. 13C) In vitro filter trap aggregation assay of mutant Huntingtin (mHttQ51) incubated with 5× or 10× molar excess of human α- or βNAC N-terminal peptides as indicated. SDS-insoluble aggregates were detected with an S-tag antibody.

(FIG. 15A) Filter trap assay was used to gauge HttQ51 aggregation with and without presence of chaperones. (FIG. 15B) Quantification of aggregation signal from (FIG. 15A). For all experiments Htt is present at 3 µM and the chaperone domains at a 5× molar excess.

(FIG. 16A) Filter trap assay was used to gauge HttQ51 aggregation with a range of titrations of ApiCCT1-bNAC from 15 µM to 0.03 µM. (FIG. 16B) Quantification of aggregation signal from (FIG. 16A). For all experiments Htt is present at 3 µM and the chaperone domains at the indicated molar excess.

DETAILED DESCRIPTION OF EMBODIMENTS

Figure 1A:
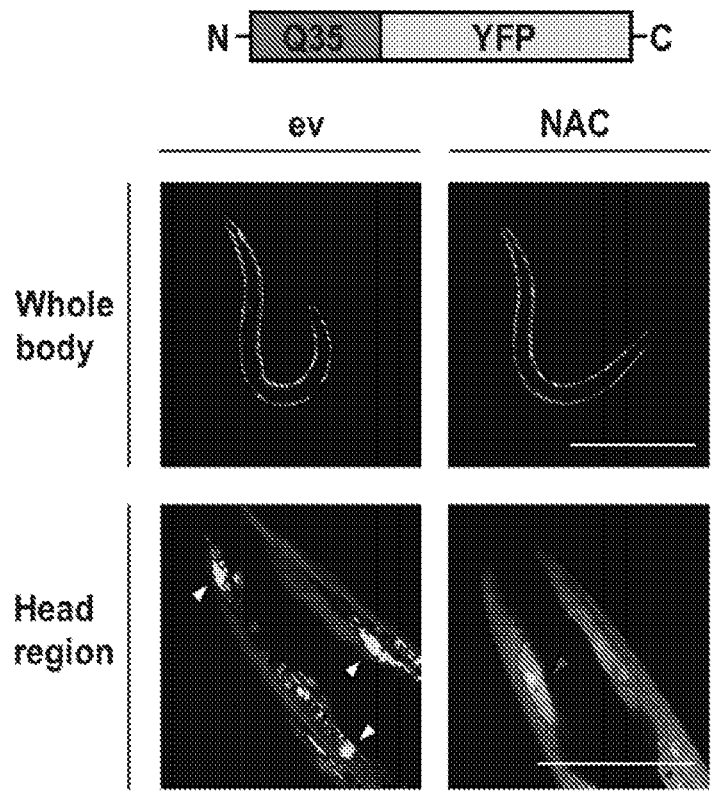
FIGS. 1A-1F show NAC suppresses aggregation of diverse PolyQ proteins.

Compositions and methods for treating aggregation-associated diseases are disclosed. In particular, compositions comprising the nascent polypeptide-associated complex (NAC) as well as peptide fragments thereof and fusion proteins containing NAC and CCT1 peptides can be used to suppress pathological aggregation of polyQ and amyloid proteins and are useful for treatment of diseases associated with polyQ aggregation, such as Huntington's disease and Spinocerebellar ataxia-3, diseases associated with amyloid beta aggregation, such as Alzheimer's disease, and synucleinopathies associated with alpha-synuclein aggregation, such as Parkinson's disease.

Before the present treatment methods are described, it is to be understood that this invention is not limited to a particular method or composition described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supersedes any disclosure of an incorporated publication to the extent there is a contradiction.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

It must be noted that as used herein and in the appended claims, the singular forms "a", "an", and "the" include plural referents unless the context clearly dictates otherwise. Thus, for example, reference to "a protein" includes a plurality of such proteins and reference to "the protein" includes reference to one or more proteins and equivalents thereof, e.g. polypeptides and peptides, known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

The term "about", particularly in reference to a given quantity, is meant to encompass deviations of plus or minus ten percent.

The terms "treatment", "treating", "treat" and the like are used herein to generally refer to obtaining a desired pharmacologic and/or physiologic effect. The effect can be prophylactic in terms of completely or partially preventing a disease or symptom(s) thereof and/or may be therapeutic in terms of a partial or complete stabilization or cure for a disease and/or adverse effect attributable to the disease. The term "treatment" encompasses any treatment of a disease in a mammal, particularly a human, and includes: (a) preventing the disease and/or symptom(s) from occurring in a subject who may be predisposed to the disease or symptom but has not yet been diagnosed as having it; (b) inhibiting the disease and/or symptom(s), i.e., arresting their development; or (c) relieving the disease symptom(s), i.e., causing regression of the disease and/or symptom(s). Those in need of treatment include those already inflicted (e.g., those with an aggregation-associated disease) as well as those in which prevention is desired (e.g., those with increased susceptibility to an aggregation-associated disease, those with a genetic predisposition to developing an aggregation-associated disease, those suspected of having an aggregation-associated disease, etc.).

A therapeutic treatment is one in which the subject is inflicted prior to administration and a prophylactic treatment is one in which the subject is not inflicted prior to administration. In some embodiments, the subject has an increased likelihood of becoming inflicted or is suspected of being inflicted prior to treatment. In some embodiments, the subject is suspected of having an increased likelihood of becoming inflicted.

"Pharmaceutically acceptable excipient or carrier" refers to an excipient that may optionally be included in the compositions of the invention and that causes no significant adverse toxicological effects to the patient.

"Pharmaceutically acceptable salt" includes, but is not limited to, amino acid salts, salts prepared with inorganic acids, such as chloride, sulfate, phosphate, diphosphate, bromide, and nitrate salts, or salts prepared from the corresponding inorganic acid form of any of the preceding, e.g., hydrochloride, etc., or salts prepared with an organic acid, such as malate, maleate, fumarate, tartrate, succinate, ethylsuccinate, citrate, acetate, lactate, methanesulfonate, benzoate, ascorbate, para-toluenesulfonate, palmoate, salicylate and stearate, as well as estolate, gluceptate and lactobionate salts. Similarly, salts containing pharmaceutically acceptable cations include, but are not limited to, sodium, potassium, calcium, aluminum, lithium, and ammonium (including substituted ammonium).

The term "survival" as used herein means the time from the start of treatment to the time of death.

Aggregation-associated diseases that can be treated by the methods described herein include, but are not limited to, polyQ aggregation-associated diseases such as Huntington's disease, dentatorubropallidoluysian atrophy (DRPLA), spinal and bulbar muscular atrophy (SBMA) also known as Kennedy's disease, and spinocerebellar ataxia (SCA) including, but not limited to, SCA Type 1 (SCA1), SCA Type 2 (SCA2), SCA Type 3 (SCA3) or Machado-Joseph disease, SCA Type 6 (SCA6), SCA Type 7 (SCA7), and SCA Type 17 (SCA17); and amyloid beta aggregation-associated diseases such as Alzheimer's disease.

By "therapeutically effective dose or amount" of a NAC protein (i.e., comprising alpha and/or beta subunits of NAC), a NAC peptide (i.e., comprising at least a portion of an N-terminal domain of a beta subunit of NAC) or a CCT1-NAC fusion protein (i.e., comprising a peptide comprising an apical domain of CCT1 connected to a peptide comprising at least a portion of an N-terminal domain of a beta subunit of NAC), as described herein, is intended an amount that, when administered, as described herein, brings about a positive therapeutic response, such as improved neurological recovery from an aggregation-associated disease such as a disease associated with polyQ aggregation, a disease associated with amyloid beta aggregation, or a disease associated with alpha-synuclein aggregation (i.e., synucleinopathy). Improved neurological recovery may include restored neuronal function, improved cognition, improved memory, or increased survival. In the case of a polyQ aggregation-associated disease, a therapeutically effective dose or amount of a NAC peptide or CCT1-NAC fusion protein may reduce polyQ protein aggregation and reduce formation of insoluble polyQ protein aggregates in the nuclei of neurons. In the case of an amyloid beta aggregation-associated disease (e.g., Alzheimer's disease), a therapeutically effective dose or amount" of a NAC protein may reduce amyloid beta aggregation and reduce formation of amyloid plaques in the brain Additionally, a therapeutically effective dose or amount may retard loss of cerebellar Purkinje neurons and loss of brain cells. In the case of an alpha-synuclein aggregation-associated disease or synucleinopathy (e.g., Parkinson's disease), a therapeutically effective dose or amount" of a NAC protein may reduce aggregation of alpha-synuclein. Additionally, a therapeutically effective dose or amount may reduce accumulation of aggregates of alpha-synuclein in neurons, nerve fibers, and/or glial cells and reduce formation of Lewy bodies.

The terms "recipient", "individual", "subject", "host", and "patient", are used interchangeably herein and refer to any mammalian subject for whom diagnosis, treatment, or therapy is desired, particularly humans. "Mammal" for purposes of treatment refers to any animal classified as a mammal, including humans, domestic and farm animals, and zoo, sports, or pet animals, such as dogs, horses, cats, cows, sheep, goats, pigs, etc. Preferably, the mammal is human.

The terms "peptide," "oligopeptide" and "polypeptide" refer to any compound comprising naturally occurring or synthetic amino acid polymers or amino acid-like molecules including but not limited to compounds comprising amino and/or imino molecules. No particular size is implied by use of the terms "peptide," "oligopeptide" or "polypeptide" and these terms are used interchangeably. Included within the definition are, for example, polypeptides containing one or more analogs of an amino acid (including, for example, unnatural amino acids, etc.), polypeptides with substituted linkages, as well as other modifications known in the art, both naturally occurring and non-naturally occurring (e.g., synthetic). Thus, synthetic oligopeptides, dimers, multimers (e.g., tandem repeats, linearly-linked peptides), cyclized, branched molecules and the like, are included within the definition. The terms also include molecules comprising one or more peptoids (e.g., N-substituted glycine residues) and other synthetic amino acids or peptides. (See, e.g., U.S. Pat. Nos. 5,831,005; 5,877,278; and U.S. Pat. No. 5,977,301; Nguyen et al. (2000) *Chem Biol.* 7(7):463-473; and Simon et al. (1992) *Proc. Natl. Acad. Sci. USA* 89(20):9367-9371 for descriptions of peptoids). Nonlimiting lengths of peptides suitable for use in the present invention includes peptides of 3 to 5 residues in length, 6 to 10 residues in length (or any integer therebetween), 11 to 20 residues in length (or any integer therebetween), 21 to 75 residues in length (or any integer therebetween), 75 to 100 (or any integer therebetween), or polypeptides of greater than 100 residues in length. Typically, polypeptides useful in this invention can have a maximum length suitable for the intended application. Preferably, the polypeptide is between about 3 and 100 residues in length. Generally, one skilled in art can easily select the maximum length in view of the teachings herein. Further, peptides and polypeptides, as described herein, for example synthetic peptides, may include additional molecules such as labels or other chemical moieties. Such moieties may further enhance interaction of the peptides or polypeptides with MARK and/or further detection of the peptides or polypeptides.

Thus, references to polypeptides or peptides also include derivatives of the amino acid sequences of the invention including one or more non-naturally occurring amino acids. A first polypeptide or peptide is "derived from" a second polypeptide or peptide if it is (i) encoded by a first polynucleotide derived from a second polynucleotide encoding the second polypeptide or peptide, or (ii) displays sequence identity to the second polypeptide or peptide as described herein. Sequence (or percent) identity can be determined as described below. Preferably, derivatives exhibit at least about 50% percent identity, more preferably at least about 80%, and even more preferably between about 85% and 99% (or any value therebetween) to the sequence from which they were derived. Such derivatives can include postexpression modifications of the polypeptide or peptide, for example, glycosylation, acetylation, phosphorylation, and the like.

Amino acid derivatives can also include modifications to the native sequence, such as deletions, additions and substitutions (generally conservative in nature), so long as the polypeptide or peptide maintains the desired activity (e.g., suppress polyQ or amyloid beta aggregation). These modifications may be deliberate, as through site-directed mutagenesis, or may be accidental, such as through mutations of hosts that produce the proteins or errors due to PCR amplification. Furthermore, modifications may be made that have one or more of the following effects: increasing ability to suppress polyQ or amyloid beta aggregation, and facilitating purification, delivery, or cell processing. Peptides, proteins, and fusion proteins described herein can be made recombinantly, synthetically, or in tissue culture.

The term "nascent polypeptide-associated complex (NAC)" as used herein encompasses all forms of NAC and also includes biologically active fragments, variants, analogs, and derivatives thereof that retain biological activity (e.g., suppress polyQ and/or amyloid beta aggregation).

A NAC polynucleotide, nucleic acid, oligonucleotide, protein, polypeptide, or peptide refers to a molecule derived from any source. The molecule need not be physically derived from an organism, but may be synthetically or recombinantly produced. A number of NAC nucleic acid and protein sequences are known. Representative NAC sequences are presented in SEQ ID NOS:1-4 and additional representative sequences, including sequences of the NAC alpha and beta subunits are listed in the National Center for Biotechnology Information (NCBI) database. See, for example, NCBI entries: Accession Nos. NP_001032726, NP_001198, NP_663430, NP_001164011, XP_010910325, XP_010908813, XP_010908812, XP_002305248, XP_024454545, XP_006372461, XP_010673263, NP_001352825, NP_001307123, NP_001307122, NP_001106673, NP_001106672, NP_005585, NP_954984, NP_001263232, XP_025001050, XP_025007073, NP_001014916, XP_024847421, XP_024847420, XP_005206635, XP_005206632, XP_024203530, XP_024203526, XP_024203523, XP_024203522, XP_020947463, XP_020947462, XP_020929967, NM_001320194, NM_001320193, NM_005594, NM_199290, XM_006719420, XM_006719413, NM_001037637, NM_001207, NM_001113199, NM_013608, NM_001282976, NM_145455, NM_001170540, NM_001276303, XM_025145282, XM_025142885, XR_003071630, and XM_025142884; all of which sequences (as entered by the date of filing of this application) are herein incorporated by reference. Any of these sequences or a variant thereof comprising a sequence having at least about 80-100% sequence identity thereto, including any percent identity within this range, such as 81, 82, 83, 84, 85, 86, 87, 88, 89, 90, 91, 92, 93, 94, 95, 96, 97, 98, or 99% sequence identity thereto, can be used to construct a NAC peptide or CTT1-NAC fusion protein, as described herein.

The term "chaperonin containing TCP1 subunit 1 (CCT1)" as used herein encompasses all forms of the CCT1 subunit of the TRiC/CCT chaperonin complex, and also includes biologically active fragments, variants, analogs, and derivatives thereof that retain biological activity (e.g., suppress polyQ aggregation).

A CCT1 polynucleotide, nucleic acid, oligonucleotide, protein, polypeptide, or peptide refers to a molecule derived from any source. The molecule need not be physically derived from an organism, but may be synthetically or recombinantly produced. A number of CCT1 nucleic acid and protein sequences are known. Representative CCT1 sequences are presented in SEQ ID NO:5 (isoform b), SEQ ID NO:6 (isoform a), and SEQ ID NO:7 (apical domain) and additional representative sequences, including sequences of the CCT1 apical domain are listed in the National Center for Biotechnology Information (NCBI) database. See, for example, NCBI entries: Accession Nos. NP_110379, NP_001008897, NP_038714, NP_001277641, NP_001033175, NP_036802, NP_732748, NP_524450, NM_001008897, NM_030752, NM_001290712, NM_013686, NM_079726, and NM_170016; all of which sequences (as entered by the date of filing of this application) are herein incorporated by reference. Any of these sequences or a variant thereof comprising a sequence having at least about 80-100% sequence identity thereto, including any percent identity within this range, such as 81, 82, 83, 84, 85, 86, 87, 88, 89, 90, 91, 92, 93, 94, 95, 96, 97, 98, or 99% sequence identity thereto, can be used to construct a CTT1-NAC fusion protein, as described herein.

The terms "fusion protein," "fusion polypeptide," or "fusion peptide" as used herein refer to a fusion comprising an apical domain of CCT1 in combination with at least a portion of an N-terminal domain of a beta subunit of NAC as part of a single continuous chain of amino acids, which chain does not occur in nature. The CCT1 peptide and the NAC peptide may be connected directly to each other by peptide bonds or may be separated by intervening amino acid sequences (i.e., linker). The fusion proteins may also contain sequences exogenous to the CCT1 peptide and the NAC peptide. For example, the fusion may include targeting or localization sequences, or tag sequences. Additionally, the fusion protein may further comprise a cell-penetrating peptide to facilitate entry into a cell.

By "fragment" is intended a molecule consisting of only a part of the intact full-length sequence and structure. The fragment can include a C-terminal deletion an N-terminal deletion, and/or an internal deletion of the polypeptide. Active fragments of a particular protein or polypeptide will generally include at least about 5-14 contiguous amino acid residues of the full length molecule, but may include at least about 15-25 contiguous amino acid residues of the full length molecule, and can include at least about 20-50 or more contiguous amino acid residues of the full length molecule, or any integer between 5 amino acids and the full length sequence, provided that the fragment in question retains biological activity (e.g., the ability to suppress polyQ or amyloid beta aggregation).

"Substantially purified" generally refers to isolation of a substance (compound, polynucleotide, protein, polypeptide, peptide composition) such that the substance comprises the majority percent of the sample in which it resides. Typically in a sample, a substantially purified component comprises 50%, preferably 80%-85%, more preferably 90-95% of the sample. Techniques for purifying polynucleotides and polypeptides of interest are well-known in the art and include, for example, ion-exchange chromatography, affinity chromatography and sedimentation according to density.

By "isolated" is meant, when referring to a protein, polypeptide, or peptide, that the indicated molecule is separate and discrete from the whole organism with which the molecule is found in nature or is present in the substantial absence of other biological macro molecules of the same type. The term "isolated" with respect to a polynucleotide is a nucleic acid molecule devoid, in whole or part, of sequences normally associated with it in nature; or a sequence, as it exists in nature, but having heterologous sequences in association therewith; or a molecule disassociated from the chromosome.

The term "derived from" is used herein to identify the original source of a molecule but is not meant to limit the method by which the molecule is made which can be, for example, by chemical synthesis or recombinant means.

The terms "variant," "analog" and "mutein" refer to biologically active derivatives of the reference molecule that retain desired activity, such the ability to suppress polyQ and/or amyloid beta aggregation for use in the treatment of an aggregation-associated disease as described herein. In general, the terms "variant" and "analog" refer to compounds having a native polypeptide sequence and structure with one or more amino acid additions, substitutions (generally conservative in nature) and/or deletions, relative to the native molecule, so long as the modifications do not destroy biological activity, and which are "substantially homologous" to the reference molecule as defined below. In general, the amino acid sequences of such analogs will have a high degree of sequence homology to the reference sequence, e.g., amino acid sequence homology of more than 50%, generally more than 60%-70%, even more particularly 80%-85% or more, such as at least 90%-95% or more, when the two sequences are aligned. Often, the analogs will include the same number of amino acids but will include substitutions, as explained herein. The term "mutein" further includes polypeptides having one or more amino acid-like molecules including but not limited to compounds comprising only amino and/or imino molecules, polypeptides containing one or more analogs of an amino acid (including, for example, unnatural amino acids, etc.), polypeptides with substituted linkages, as well as other modifications known in the art, both naturally occurring and non-naturally occurring (e.g., synthetic), cyclized, branched molecules and the like. The term also includes molecules comprising one or more N-substituted glycine residues (a "peptoid") and other synthetic amino acids or peptides. (See, e.g., U.S. Pat. Nos. 5,831,005; 5,877,278; and U.S. Pat. No. 5,977,301; Nguyen et al., *Chem Biol.* (2000) 7:463-473; and Simon et al., *Proc. Natl. Acad. Sci. USA* (1992) 89:9367-9371 for descriptions of peptoids). Preferably, the analog or mutein has at least the same biological activity as the native molecule. Methods for making polypeptide analogs and muteins are known in the art and are described further below.

As explained above, analogs generally include substitutions that are conservative in nature, i.e., those substitutions that take place within a family of amino acids that are related in their side chains. Specifically, amino acids are generally divided into four families: (1) acidic—aspartate and glutamate; (2) basic—lysine, arginine, histidine; (3) non-polar—alanine, valine, leucine, isoleucine, proline, phenylalanine, methionine, tryptophan; and (4) uncharged polar—glycine, asparagine, glutamine, cysteine, serine threonine, tyrosine. Phenylalanine, tryptophan, and tyrosine are sometimes classified as aromatic amino acids. For example, it is reasonably predictable that an isolated replacement of leucine with isoleucine or valine, an aspartate with a glutamate, a threonine with a serine, or a similar conservative replacement of an amino acid with a structurally related amino acid, will not have a major effect on the biological activity. For example, the polypeptide of interest may include up to about 5-10 conservative or non-conservative amino acid substitutions, or even up to about 15-25 conservative or non-conservative amino acid substitutions, or any integer between 5-25, so long as the desired function of the molecule remains intact. One of skill in the art may readily determine regions of the molecule of interest that can tolerate change by reference to Hopp/Woods and Kyte-Doolittle plots, well known in the art.

By "derivative" is intended any suitable modification of the native polypeptide of interest, of a fragment of the native polypeptide, or of their respective analogs, such as glycosylation, phosphorylation, polymer conjugation (such as with polyethylene glycol), or other addition of foreign moieties, as long as the desired biological activity of the native polypeptide is retained. Methods for making polypeptide fragments, analogs, and derivatives are generally available in the art.

"Homology" refers to the percent identity between two polynucleotide or two polypeptide molecules. Two nucleic acid, or two polypeptide sequences are "substantially homologous" to each other when the sequences exhibit at least about 50% sequence identity, preferably at least about 75% sequence identity, more preferably at least about 80% 85% sequence identity, more preferably at least about 90% sequence identity, and most preferably at least about 95% 98% sequence identity over a defined length of the molecules. As used herein, substantially homologous also refers to sequences showing complete identity to the specified sequence.

In general, "identity" refers to an exact nucleotide to nucleotide or amino acid to amino acid correspondence of two polynucleotides or polypeptide sequences, respectively. Percent identity can be determined by a direct comparison of the sequence information between two molecules by aligning the sequences, counting the exact number of matches between the two aligned sequences, dividing by the length of the shorter sequence, and multiplying the result by 100. Readily available computer programs can be used to aid in the analysis, such as ALIGN, Dayhoff, M. O. in *Atlas of Protein Sequence and Structure* M. O. Dayhoff ed., 5 Suppl. 3:353 358, National biomedical Research Foundation, Washington, DC, which adapts the local homology algorithm of Smith and Waterman *Advances in Appl. Math.* 2:482 489, 1981 for peptide analysis. Programs for determining nucleotide sequence identity are available in the Wisconsin Sequence Analysis Package, Version 8 (available from Genetics Computer Group, Madison, WI) for example, the BESTFIT, FASTA and GAP programs, which also rely on the Smith and Waterman algorithm. These programs are readily utilized with the default parameters recommended by the manufacturer and described in the Wisconsin Sequence Analysis Package referred to above. For example, percent identity of a particular nucleotide sequence to a reference sequence can be determined using the homology algorithm of Smith and Waterman with a default scoring table and a gap penalty of six nucleotide positions.

Another method of establishing percent identity in the context of the present invention is to use the MPSRCH package of programs copyrighted by the University of Edinburgh, developed by John F. Collins and Shane S. Sturrok, and distributed by IntelliGenetics, Inc. (Mountain View, CA). From this suite of packages, the Smith Waterman algorithm can be employed where default parameters are used for the scoring table (for example, gap open penalty of 12, gap extension penalty of one, and a gap of six). From the data generated the "Match" value reflects "sequence identity." Other suitable programs for calculating the percent identity or similarity between sequences are generally known in the art, for example, another alignment program is BLAST, used with default parameters. For example, BLASTN and BLASTP can be used using the following default parameters: genetic code=standard; filter=none;

strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+Swiss protein+Spupdate+PIR. Details of these programs are readily available.

Alternatively, homology can be determined by hybridization of polynucleotides under conditions which form stable duplexes between homologous regions, followed by digestion with single stranded specific nuclease(s), and size determination of the digested fragments. DNA sequences that are substantially homologous can be identified in a Southern hybridization experiment under, for example, stringent conditions, as defined for that particular system. Defining appropriate hybridization conditions is within the skill of the art. See, e.g., Sambrook et al., supra; DNA Cloning, supra; Nucleic Acid Hybridization, supra.

"Recombinant" as used herein to describe a nucleic acid molecule means a polynucleotide of genomic, cDNA, viral, semisynthetic, or synthetic origin which, by virtue of its origin or manipulation, is not associated with all or a portion of the polynucleotide with which it is associated in nature. The term "recombinant" as used with respect to a protein or polypeptide means a polypeptide produced by expression of a recombinant polynucleotide. In general, the gene of interest is cloned and then expressed in transformed organisms, as described further below. The host organism expresses the foreign gene to produce the protein under expression conditions.

The term "transformation" refers to the insertion of an exogenous polynucleotide into a host cell, irrespective of the method used for the insertion. For example, direct uptake, transduction or f-mating are included. The exogenous polynucleotide may be maintained as a non-integrated vector, for example, a plasmid, or alternatively, may be integrated into the host genome.

"Recombinant host cells," "host cells," "cells", "cell lines," "cell cultures," and other such terms denoting microorganisms or higher eukaryotic cell lines cultured as unicellular entities refer to cells which can be, or have been, used as recipients for recombinant vector or other transferred DNA, and include the original progeny of the original cell which has been transfected.

A "coding sequence" or a sequence which "encodes" a selected polypeptide, is a nucleic acid molecule which is transcribed (in the case of DNA) and translated (in the case of mRNA) into a polypeptide in vivo when placed under the control of appropriate regulatory sequences (or "control elements"). The boundaries of the coding sequence can be determined by a start codon at the 5' (amino) terminus and a translation stop codon at the 3' (carboxy) terminus. A coding sequence can include, but is not limited to, cDNA from viral, prokaryotic or eukaryotic mRNA, genomic DNA sequences from viral or prokaryotic DNA, and even synthetic DNA sequences. A transcription termination sequence may be located 3' to the coding sequence.

Typical "control elements," include, but are not limited to, transcription promoters, transcription enhancer elements, transcription termination signals, polyadenylation sequences (located 3' to the translation stop codon), sequences for optimization of initiation of translation (located 5' to the coding sequence), and translation termination sequences.

"Operably linked" refers to an arrangement of elements wherein the components so described are configured so as to perform their usual function. Thus, a given promoter operably linked to a coding sequence is capable of effecting the expression of the coding sequence when the proper enzymes are present. The promoter need not be contiguous with the coding sequence, so long as it functions to direct the expression thereof. Thus, for example, intervening untranslated yet transcribed sequences can be present between the promoter sequence and the coding sequence and the promoter sequence can still be considered "operably linked" to the coding sequence.

"Encoded by" refers to a nucleic acid sequence which codes for a polypeptide sequence, wherein the polypeptide sequence or a portion thereof contains an amino acid sequence of at least 3 to 5 amino acids, more preferably at least 8 to 10 amino acids, and even more preferably at least 15 to 20 amino acids from a polypeptide encoded by the nucleic acid sequence.

"Expression cassette" or "expression construct" refers to an assembly which is capable of directing the expression of the sequence(s) or gene(s) of interest. An expression cassette generally includes control elements, as described above, such as a promoter which is operably linked to (so as to direct transcription of) the sequence(s) or gene(s) of interest, and often includes a polyadenylation sequence as well. Within certain embodiments of the invention, the expression cassette described herein may be contained within a plasmid construct. In addition to the components of the expression cassette, the plasmid construct may also include, one or more selectable markers, a signal which allows the plasmid construct to exist as single stranded DNA (e.g., a M13 origin of replication), at least one multiple cloning site, and a "mammalian" origin of replication (e.g., a SV40 or adenovirus origin of replication).

"Purified polynucleotide" refers to a polynucleotide of interest or fragment thereof which is essentially free, e.g., contains less than about 50%, preferably less than about 70%, and more preferably less than about at least 90%, of the protein with which the polynucleotide is naturally associated. Techniques for purifying polynucleotides of interest are well-known in the art and include, for example, disruption of the cell containing the polynucleotide with a chaotropic agent and separation of the polynucleotide(s) and proteins by ion-exchange chromatography, affinity chromatography and sedimentation according to density.

The term "transfection" is used to refer to the uptake of foreign DNA by a cell. A cell has been "transfected" when exogenous DNA has been introduced inside the cell membrane. A number of transfection techniques are generally known in the art. See, e.g., Graham et al. (1973) *Virology*, 52:456, Sambrook et al. (2001) *Molecular Cloning, a laboratory manual*, 3rd edition, Cold Spring Harbor Laboratories, New York, Davis et al. (1995) *Basic Methods in Molecular Biology*, 2nd edition, McGraw-Hill, and Chu et al. (1981) *Gene* 13:197. Such techniques can be used to introduce one or more exogenous DNA moieties into suitable host cells. The term refers to both stable and transient uptake of the genetic material, and includes uptake of peptide- or antibody-linked DNAs.

A "vector" is capable of transferring nucleic acid sequences to target cells (e.g., viral vectors, non-viral vectors, particulate carriers, and liposomes). Typically, "vector construct," "expression vector," and "gene transfer vector," mean any nucleic acid construct capable of directing the expression of a nucleic acid of interest and which can transfer nucleic acid sequences to target cells. Thus, the term includes cloning and expression vehicles, as well as viral vectors.

The terms "variant," "analog" and "mutein" refer to biologically active derivatives of the reference molecule that retain desired activity, such as the ability to inhibit MARK and reduce tau hyperphosphorylation. In general, the terms "variant" and "analog" refer to compounds having a native polypeptide sequence and structure with one or more amino acid additions, substitutions (generally conservative in nature) and/or deletions, relative to the native molecule, so long as the modifications do not destroy biological activity, and which are "substantially homologous" to the reference molecule as defined below. In general, the amino acid sequences of such analogs will have a high degree of sequence homology to the reference sequence, e.g., amino acid sequence homology of more than 50%, generally more than 60%-70%, even more particularly 80%-85% or more, such as at least 90%-95% or more, when the two sequences are aligned. Often, the analogs will include the same number of amino acids but will include substitutions, as explained herein. The term "mutein" further includes polypeptides having one or more amino acid-like molecules including but not limited to compounds comprising only amino and/or imino molecules, polypeptides containing one or more analogs of an amino acid (including, for example, unnatural amino acids, etc.), polypeptides with substituted linkages, as well as other modifications known in the art, both naturally occurring and non-naturally occurring (e.g., synthetic), cyclized, branched molecules and the like. The term also includes molecules comprising one or more N-substituted glycine residues (a "peptoid") and other synthetic amino acids or peptides. (See, e.g., U.S. Pat. Nos. 5,831,005; 5,877,278; and U.S. Pat. No. 5,977,301; Nguyen et al., *Chem. Biol.* (2000) 7:463-473; and Simon et al., *Proc. Natl. Acad. Sci. USA* (1992) 89:9367-9371 for descriptions of peptoids). Methods for making polypeptide analogs and muteins are known in the art and are described further below.

As explained above, analogs generally include substitutions that are conservative in nature, i.e., those substitutions that take place within a family of amino acids that are related in their side chains. Specifically, amino acids are generally divided into four families: (1) acidic—aspartate and glutamate; (2) basic—lysine, arginine, histidine; (3) non-polar—alanine, valine, leucine, isoleucine, proline, phenylalanine, methionine, tryptophan; and (4) uncharged polar—glycine, asparagine, glutamine, cysteine, serine threonine, and tyrosine. Phenylalanine, tryptophan, and tyrosine are sometimes classified as aromatic amino acids. For example, it is reasonably predictable that an isolated replacement of leucine with isoleucine or valine, an aspartate with a glutamate, a threonine with a serine, or a similar conservative replacement of an amino acid with a structurally related amino acid, will not have a major effect on the biological activity. For example, the polypeptide of interest may include up to about 5-10 conservative or non-conservative amino acid substitutions, or even up to about 15-25 conservative or non-conservative amino acid substitutions, or any integer between 5-25, so long as the desired function of the molecule remains intact. One of skill in the art may readily determine regions of the molecule of interest that can tolerate change by reference to Hopp/Woods and Kyte-Doolittle plots, well known in the art.

"Gene transfer" or "gene delivery" refers to methods or systems for reliably inserting DNA or RNA of interest into a host cell. Such methods can result in transient expression of non-integrated transferred DNA, extrachromosomal replication and expression of transferred replicons (e.g., episomes), or integration of transferred genetic material into the genomic DNA of host cells. Gene delivery expression vectors include, but are not limited to, vectors derived from bacterial plasmid vectors, viral vectors, non-viral vectors, alphaviruses, pox viruses and vaccinia viruses.

A polynucleotide "derived from" a designated sequence refers to a polynucleotide sequence which comprises a contiguous sequence of approximately at least about 6 nucleotides, preferably at least about 8 nucleotides, more preferably at least about 10-12 nucleotides, and even more preferably at least about 15-20 nucleotides corresponding, i.e., identical or complementary to, a region of the designated nucleotide sequence. The derived polynucleotide will not necessarily be derived physically from the nucleotide sequence of interest, but may be generated in any manner, including, but not limited to, chemical synthesis, replication, reverse transcription or transcription, which is based on the information provided by the sequence of bases in the region (s) from which the polynucleotide is derived. As such, it may represent either a sense or an antisense orientation of the original polynucleotide.

Suppressing PolyQ Aggregation with NAC Peptides and CTT1-NAC Fusion Proteins

PolyQ aggregation-associated diseases are caused by pathological expansion of CAG repeats in the coding regions of certain genes. A number of neurological diseases are associated with pathological accumulation of polyQ protein aggregates in specific regions of the brain and spinal cord. The precise regions affected by polyQ aggregation depend on the particular disease and the genes compromised by the expanded CAG repeats.

PolyQ protein aggregation can be suppressed by a NAC peptide comprising at least a portion of an N-terminal domain of a beta subunit of NAC. The peptide will generally include at least the C-terminal portion of the N-terminal domain corresponding to amino acid residues 23 to 38 numbered relative to the reference sequence of SEQ ID NO:1. In some embodiments, the peptide comprises or consists of the entire N-terminal domain of the NAC beta subunit. In certain embodiments, the peptide comprises or consists of an amino acid sequence selected from the group consisting of SEQ ID NOS:1-3, or sequences displaying at least about 80-100% sequence identity thereto, including any percent identity within this range, such as 81, 82, 83, 84, 85, 86, 87, 88, 89, 90, 91, 92, 93, 94, 95, 96, 97, 98, 99% sequence identity thereto, wherein the peptide is capable of suppressing aggregation of a protein comprising a polyQ sequence.

Fusion proteins comprising a NAC peptide (i.e., comprising at least a portion of an N-terminal domain of a beta subunit of NAC) connected to a peptide comprising an apical domain of CCT1 have enhanced ability to suppress aggregation of polyQ-expanded Huntingtin, which forms the toxic aggregates associated with Huntington's disease (see Example 2). Without being bound by a particular theory, the specific mechanism by which the apical domain of CCT1 suppresses aggregation may involve sequestering the hydrophobic surface of the N-terminal 17 amino acids (N17) of the Huntingtin exon1 and preventing Huntingtin self-oligomerization into toxic aggregation species. The N17 region is adjacent to the polyQ residues. Thus, the fusion of ApiCCT1 to a NAC peptide improves targeting to the N17 and polyQ domains of the Huntingtin exon1, and the cooperative roles of the NAC and CCT1 domains in suppressing aggregation synergistically enhance the efficacy of the fusion protein.

In the fusion protein, the CCT1 peptide and the NAC peptide may be connected directly to each other by peptide bonds or may be separated by intervening amino acid sequences (i.e., linker). The fusion protein may also contain sequences exogenous to the CCT1 peptide and the NAC peptide. For example, the fusion may include targeting or localization sequences, or tag sequences. Additionally, the fusion protein may further comprise a cell-penetrating peptide to facilitate entry into a cell.

In certain embodiments, the fusion protein can be represented by the formula $NH_2$-A-apiCTT1-L-βNAC—B—COOH, wherein: apiCTT1 is an amino acid sequence of a peptide comprising an apical domain of CCT1; L is an optional linker amino acid sequence; βNAC is an amino acid sequence of a peptide comprising at least a portion of an N-terminal domain of a beta subunit of NAC; A is an optional N-terminal amino acid sequence; and B is an optional C-terminal amino acid sequence.

Linker amino acid sequence(s)—L—will typically be short, e.g., 20 or fewer amino acids (i.e., 20, 19, 18, 17, 16, 15, 14, 13, 12, 11, 10, 9, 8, 7, 6, 5, 4, 3, 2, or 1). Examples include short peptide sequences which facilitate cloning, poly-glycine linkers ($Gly_n$ where n=2, 3, 4, 5, 6, 7, 8, 9, 10 or more), histidine tags ($His_n$ where n=3, 4, 5, 6, 7, 8, 9, 10 or more), linkers composed of glycine and serine residues, GSAT, SEG, and Z-EGFR linkers. Linkers may include restriction sites, which aid cloning and manipulation. Other suitable linker amino acid sequences will be apparent to those skilled in the art. (See e.g., Argos (1990) *J. Mol. Biol.* 211(4):943-958; Crasto et al. (2000) *Protein Eng.* 13:309-312; George et al. (2002) *Protein Eng.* 15:871-879; Arai et al. (2001) *Protein Eng.* 14:529-532; and the Registry of Standard Biological Parts (partsregistry.org/Protein_domains/Linker).

—A— is an optional N-terminal amino acid sequence. This will typically be short, e.g., 40 or fewer amino acids (i.e., 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, or 1). Examples include leader sequences to direct protein localization, or short peptide sequences or tag sequences, which facilitate cloning or purification (e.g., a histidine tag $His_n$ where n=3, 4, 5, 6, 7, 8, 9, 10 or more). Other suitable N-terminal amino acid sequences will be apparent to those skilled in the art.

—B— is an optional C-terminal amino acid sequence. This will typically be short, e.g., 40 or fewer amino acids (i.e., 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, or 1). Examples include sequences to direct protein localization, short peptide sequences or tag sequences, which facilitate cloning or purification (e.g., $His_n$ where n=3, 4, 5, 6, 7, 8, 9, 10 or more), or sequences which enhance protein stability. Other suitable C-terminal amino acid sequences will be apparent to those skilled in the art.

In certain embodiments, tag sequences are located at the N-terminus or C-terminus of the fusion protein. Exemplary tags that can be used in the practice of the invention include a His-tag, a Strep-tag, a TAP-tag, an S-tag, an SBP-tag, an Arg-tag, a calmodulin-binding peptide tag, a cellulose-binding domain tag, a DsbA tag, a c-myc tag, a glutathione S-transferase tag, a FLAG tag, a HAT-tag, a maltose-binding protein tag, a NusA tag, and a thioredoxin tag.

In certain embodiments, a NAC peptide or a CTT1-NAC fusion protein is linked to an internalization sequence, a protein transduction domain, or a cell-penetrating peptide to facilitate entry into a cell. Cell penetrating peptides that can be used in the practice of the invention include, but are not limited to, HIV-Tat, penetratin, transportan, octaarginine, nonaarginine, antennapedia, TP10, Buforin II, MAP (model amphipathic peptide), K-FGF, Ku70, mellittin, pVEC, Pep-1, SynB1, Pep-7, CADY, GALA, pHLIP, KALA, R7W, and HN-1, which can readily transport molecules and small peptides across plasma membranes (see, e.g., Jones et al. (2012) *J. Control Release* 161(2):582-591; Fonseca et al. (2009) *Adv. Drug Deliv. Rev.* 61(11):953-64; Schwarze et al. (1999) *Science.* 285(5433):1569-72; Derossi et al. (1996) *J. Biol. Chem.* 271(30):18188-18193; Fuchs et al. (2004) *Biochemistry* 43(9):2438-2444; and Yuan et al. (2002) *Cancer Res.* 62(15):4186-4190; herein incorporated by reference.

NAC peptides (i.e., comprising at least a portion of an N-terminal domain of a beta subunit of NAC) and CTT1-NAC fusion proteins described herein are capable of suppressing aggregation of polyQ proteins that cause aggregation-associated diseases. Exemplary polyQ proteins whose aggregation is associated with neurological disorders include polyQ-expanded huntingtin exon1, associated with Huntington's disease; polyQ-expanded ataxin-1, associated with spinocerebellar ataxia-1; polyQ-expanded ataxin-3, associated with spinocerebellar ataxia-3; and polyQ-expanded androgen receptor associated with SBMA (Kennedy's disease). Thus, in some embodiments, a NAC peptide or CTT1-NAC fusion protein suppresses aggregation of at least one polyQ protein that causes an aggregation-associated disease. Suppression of aggregation may be complete or partial (i.e., all aggregation, some aggregation, or most aggregation is blocked by the NAC peptide or CTT1-NAC fusion protein), which depends, in part, on the amount of the NAC peptide or CTT1-NAC fusion protein that is administered.

Suppressing Amyloid Beta Aggregation with NAC

Amyloid beta (Aβ or Abeta) peptides such as Aβ 36-43 are components of amyloid plaques associated with Alzheimer's disease. Aggregation of such Aβ peptides can be suppressed by a NAC protein. In one embodiment, aggregation of one or more amyloid peptides selected from the group consisting of Aβ36, Aβ37, Aβ38, Aβ39, Aβ40, Aβ41, Aβ42, and Aβ43 is suppressed by administering a NAC protein to a subject who has Alzheimer's disease.

Suppressing Alpha-Synuclein Aggregation with NAC

Synucleinopathies are neurodegenerative diseases associated with pathological accumulation of aggregates of alpha-synuclein in neurons, nerve fibers, or glial cells. Synucleinopathies include, but are not limited to, Parkinson's disease, dementia with Lewy bodies, multiple system atrophy, and various neuroaxonal dystrophies. Certain mutations cause alpha-synuclein to form amyloid-like fibrils that contribute to pathogenesis of Parkinson's disease. In particular, the five mutations A53T, A30P, E46K, H50Q, and G51D in alpha-synuclein are linked to Parkinson's disease. Aggregation of alpha-synuclein can be suppressed by a NAC protein. In one embodiment, aggregation of alpha-synuclein is suppressed by administering a NAC protein to a subject who has a synucleinopathy.

Production of Peptides, Proteins, and Fusion Proteins

NAC proteins (i.e., comprising alpha and/or beta subunits of NAC), NAC peptides (i.e., comprising at least a portion of an N-terminal domain of a beta subunit of NAC) and CCT1-NAC fusion proteins (i.e., comprising a peptide comprising an apical domain of CCT1 connected to a peptide comprising at least a portion of an N-terminal domain of a beta subunit of NAC) can be prepared in any suitable manner (e.g., recombinant expression, purification from cell culture, chemical synthesis, etc.) and in various forms (e.g. native, fusions, labeled, lipidated, amidated, acetylated, PEGylated, etc.). The NAC proteins, NAC peptides, and CCT1-NAC fusion proteins may include naturally occurring polypeptides, recombinantly produced polypeptides, synthetically produced polypeptides, or polypeptides produced by a combination of these methods. Means for preparing proteins, peptides, and fusion proteins are well understood in the art. Proteins, peptides, and fusion proteins are preferably prepared in substantially pure form (i.e. substantially free from other host cell or non-host cell proteins).

NAC nucleic acid and protein sequences may be derived from any source. A number of NAC nucleic acid and protein sequences are known. Representative NAC sequences are presented in SEQ ID NOS:1-4 and additional representative sequences, including sequences of the NAC alpha and beta subunits are listed in the National Center for Biotechnology Information (NCBI) database. See, for example, NCBI entries: Accession Nos. NP_001032726, NP_001198, NP_663430, NP_001164011, XP_010910325, XP_010908813, XP_010908812, XP_002305248, XP_024454545, XP_006372461, XP_010673263, NP_001352825, NP_001307123, NP_001307122, NP_001106673, NP_001106672, NP_005585, NP_954984, NP_001263232, XP_025001050, XP_025007073, NP_001014916, XP_024847421, XP_024847420, XP_005206635, XP_005206632, XP_024203530, XP_024203526, XP_024203523, XP_024203522, XP_020947463, XP_020947462, XP_020929967, NM_001320194, NM_001320193, NM_005594, NM_199290, XM_006719420, XM_006719413, NM_001037637, NM_001207, NM_001113199, NM_013608, NM_001282976, NM_145455, NM_001170540, NM_001276303, XM_025145282, XM_025142885, XR_003071630, and XM_025142884; all of which sequences (as entered by the date of filing of this application) are herein incorporated by reference. Any of these sequences or a variant thereof comprising a sequence having at least about 80-100% sequence identity thereto, including any percent identity within this range, such as 81, 82, 83, 84, 85, 86, 87, 88, 89, 90, 91, 92, 93, 94, 95, 96, 97, 98, or 99% sequence identity thereto, can be used to construct a NAC peptide or CTT1-NAC fusion protein, as described herein.

CCT1 nucleic acid and protein sequences may be derived from any source. A number of CCT1 nucleic acid and protein sequences are known. Representative CCT1 sequences are presented in SEQ ID NO:5 (isoform b), SEQ ID NO:6 (isoform a), and SEQ ID NO:7 (apical domain) and additional representative sequences, including sequences of the CCT1 apical domain are listed in the National Center for Biotechnology Information (NCBI) database. See, for example, NCBI entries: Accession Nos. NP_110379, NP_001008897, NP_038714, NP_001277641, NP_001033175, NP_036802, NP_732748, NP_524450, NM_001008897, NM_030752, NM_001290712, NM_013686, NM_079726, and NM_170016; all of which sequences (as entered by the date of filing of this application) are herein incorporated by reference. Any of these sequences or a variant thereof comprising a sequence having at least about 80-100% sequence identity thereto, including any percent identity within this range, such as 81, 82, 83, 84, 85, 86, 87, 88, 89, 90, 91, 92, 93, 94, 95, 96, 97, 98, or 99% sequence identity thereto, can be used to construct a CTT1-NAC fusion protein, as described herein.

In one embodiment, proteins, peptides, or fusion proteins are generated using recombinant techniques. One of skill in the art can readily determine nucleotide sequences that encode the desired proteins, peptides, or fusion proteins using standard methodology and the teachings herein. Oligonucleotide probes can be devised based on the known sequences and used to probe genomic or cDNA libraries. The sequences can then be further isolated using standard techniques and, e.g., restriction enzymes employed to truncate the gene at desired portions of the full-length sequence. Similarly, sequences of interest can be isolated directly from cells and tissues containing the same, using known techniques, such as phenol extraction and the sequence further manipulated to produce the desired truncations. See, e.g., Sambrook et al., supra, for a description of techniques used to obtain and isolate DNA.

The sequences encoding proteins, peptides, or fusion proteins can also be produced synthetically, for example, based on the known sequences. The nucleotide sequence can be designed with the appropriate codons for the particular amino acid sequence desired. The complete sequence is generally assembled from overlapping oligonucleotides prepared by standard methods and assembled into a complete coding sequence. See, e.g., Edge (1981) *Nature* 292:756; Nambair et al. (1984) *Science* 223:1299; Jay et al. (1984) *J. Biol Chem.* 259:6311; Stemmer et al. (1995) *Gene* 164:49-53.

Recombinant techniques are readily used to clone sequences encoding proteins, peptides, or fusion proteins that can then be mutagenized in vitro by the replacement of the appropriate base pair(s) to result in the codon for the desired amino acid. Such a change can include as little as one base pair, effecting a change in a single amino acid, or can encompass several base pair changes. Alternatively, the mutations can be effected using a mismatched primer that hybridizes to the parent nucleotide sequence (generally cDNA corresponding to the RNA sequence), at a temperature below the melting temperature of the mismatched duplex. The primer can be made specific by keeping primer length and base composition within relatively narrow limits and by keeping the mutant base centrally located. See, e.g., Innis et al, (1990) PCR Applications: Protocols for Functional Genomics; Zoller and Smith, *Methods Enzymol.* (1983) 100:468. Primer extension is effected using DNA polymerase, the product cloned and clones containing the mutated DNA, derived by segregation of the primer extended strand, selected. Selection can be accomplished using the mutant primer as a hybridization probe. The technique is also applicable for generating multiple point mutations. See, e.g., Dalbie-McFarland et al. *Proc. Natl. Acad. Sci USA* (1982) 79:6409.

Once coding sequences have been isolated and/or synthesized, they can be cloned into any suitable vector or replicon for expression. (See, also, Examples). As will be apparent from the teachings herein, a wide variety of vectors encoding modified peptides can be generated by creating expression constructs which operably link, in various combinations, polynucleotides encoding peptides having deletions or mutations therein.

Numerous cloning vectors are known to those of skill in the art, and the selection of an appropriate cloning vector is a matter of choice. Examples of recombinant DNA vectors for cloning and host cells which they can transform include the bacteriophage λ (*E. coli*), pBR322 (*E. coli*), pACYC177 (*E. coli*), pKT230 (gram-negative bacteria), pGV1106 (gram-negative bacteria), pLAFR1 (gram-negative bacteria), pME290 (non-*E. coli* gram-negative bacteria), pHV14

(*E. coli* and *Bacillus subtilis*), pBD9 (*Bacillus*), pIJ61 (*Streptomyces*), pUC6 (*Streptomyces*), YIp5 (*Saccharomyces*), YCp19 (*Saccharomyces*) and bovine papilloma virus (mammalian cells). See, generally, *DNA Cloning: Vols. I & II*, supra; Sambrook et al., supra; B. Perbal, supra.

Insect cell expression systems, such as baculovirus systems, can also be used and are known to those of skill in the art and described in, e.g., Summers and Smith, *Texas Agricultural Experiment Station Bulletin* No. 1555 (1987). Materials and methods for baculovirus/insect cell expression systems are commercially available in kit form from, inter alia, Invitrogen, San Diego CA ("MaxBac" kit).

Plant expression systems can also be used to produce the NAC proteins, NAC peptides, and CCT1-NAC fusion proteins described herein. Generally, such systems use virus-based vectors to transfect plant cells with heterologous genes. For a description of such systems, see, e.g., Porta et al., *Mol. Biotech.* (1996) 5:209-221; and Hackland et al., *Arch. Virol.* (1994) 139:1-22.

Viral systems, such as a vaccinia-based infection/transfection system, as described in Tomei et al., *J. Virol.* (1993) 67:4017-4026 and Selby et al., *J. Gen. Virol.* (1993) 74:1103-1113, will also find use with the present invention. In this system, cells are first transfected in vitro with a vaccinia virus recombinant that encodes the bacteriophage T7 RNA polymerase. This polymerase displays exquisite specificity in that it only transcribes templates bearing T7 promoters. Following infection, cells are transfected with the DNA of interest, driven by a T7 promoter. The polymerase expressed in the cytoplasm from the vaccinia virus recombinant transcribes the transfected DNA into RNA that is then translated into protein by the host translational machinery. The method provides for high level, transient, cytoplasmic production of large quantities of RNA and its translation product(s).

The gene can be placed under the control of a promoter, ribosome binding site (for bacterial expression) and, optionally, an operator (collectively referred to herein as "control" elements), so that the DNA sequence encoding the desired polypeptide is transcribed into RNA in the host cell transformed by a vector containing this expression construction. The coding sequence may or may not contain a signal peptide or leader sequence. With the present invention, both the naturally occurring signal peptides or heterologous sequences can be used. Leader sequences can be removed by the host in post-translational processing. See, e.g., U.S. Pat. Nos. 4,431,739; 4,425,437; 4,338,397. Such sequences include, but are not limited to, the TPA leader, as well as the honeybee mellitin signal sequence.

Other regulatory sequences may also be desirable which allow for regulation of expression of the protein sequences relative to the growth of the host cell. Such regulatory sequences are known to those of skill in the art, and examples include those which cause the expression of a gene to be turned on or off in response to a chemical or physical stimulus, including the presence of a regulatory compound. Other types of regulatory elements may also be present in the vector, for example, enhancer sequences.

The control sequences and other regulatory sequences may be ligated to the coding sequence prior to insertion into a vector. Alternatively, the coding sequence can be cloned directly into an expression vector that already contains the control sequences and an appropriate restriction site.

In some cases, it may be necessary to modify the coding sequence so that it may be attached to the control sequences with the appropriate orientation; i.e., to maintain the proper reading frame. Mutants or analogs may be prepared by the deletion of a portion of the sequence encoding the protein, by insertion of a sequence, and/or by substitution of one or more nucleotides within the sequence. Techniques for modifying nucleotide sequences, such as site-directed mutagenesis, are well known to those skilled in the art. See, e.g., Sambrook et al., supra; *DNA Cloning, Vols. I and II*, supra; *Nucleic Acid Hybridization*, supra.

The expression vector is then used to transform an appropriate host cell. A number of mammalian cell lines are known in the art and include immortalized cell lines available from the American Type Culture Collection (ATCC), such as, but not limited to, Chinese hamster ovary (CHO) cells, HeLa cells, baby hamster kidney (BHK) cells, monkey kidney cells (COS), human hepatocellular carcinoma cells (e.g., Hep G2), Vero293 cells, as well as others. Similarly, bacterial hosts such as *E. coli, Bacillus subtilis*, and *Streptococcus* spp., will find use with the present expression constructs. Yeast hosts useful in the present invention include inter alia, *Saccharomyces cerevisiae, Candida albicans, Candida maltosa, Hansenula polymorpha, Kluyveromyces fragilis, Kluyveromyces lactis, Pichia guillerimondii, Pichia pastoris, Schizosaccharomyces pombe* and *Yarrowia lipolytica*. Insect cells for use with baculovirus expression vectors include, inter alia, *Aedes aegypti, Autographa californica, Bombyx mori, Drosophila melanogaster, Spodoptera frugiperda*, and *Trichoplusia ni*.

Depending on the expression system and host selected, the fusion proteins of the present invention are produced by growing host cells transformed by an expression vector described above under conditions whereby the protein of interest is expressed. The selection of the appropriate growth conditions is within the skill of the art.

In one embodiment, the transformed cells secrete the NAC protein, NAC peptide, or CCT1-NAC fusion protein product into the surrounding media. Certain regulatory sequences can be included in the vector to enhance secretion of the protein product, for example using a tissue plasminogen activator (TPA) leader sequence, an interferon (y or x) signal sequence or other signal peptide sequences from known secretory proteins. The secreted NAC protein, NAC peptide, or CCT1-NAC fusion protein product can then be isolated by various techniques described herein, for example, using standard purification techniques such as but not limited to, hydroxyapatite resins, column chromatography, ion-exchange chromatography, size-exclusion chromatography, electrophoresis, HPLC, immunoadsorbent techniques, affinity chromatography, immunoprecipitation, and the like.

Alternatively, the transformed cells are disrupted, using chemical, physical or mechanical means, which lyse the cells yet keep the recombinant peptides or polypeptides substantially intact. Intracellular proteins can also be obtained by removing components from the cell wall or membrane, e.g., by the use of detergents or organic solvents, such that leakage of the polypeptides occurs. Such methods are known to those of skill in the art and are described in, e.g., *Protein Purification Applications: A Practical Approach*, (Simon Roe, Ed., 2001).

For example, methods of disrupting cells for use with the present invention include but are not limited to: sonication or ultrasonication; agitation; liquid or solid extrusion; heat treatment; freeze-thaw; desiccation; explosive decompression; osmotic shock; treatment with lytic enzymes including proteases such as trypsin, neuraminidase and lysozyme; alkali treatment; and the use of detergents and solvents such as bile salts, sodium dodecylsulphate, Triton, NP40 and CHAPS. The particular technique used to disrupt the cells is largely a matter of choice and will depend on the cell type in which the polypeptide is expressed, culture conditions and any pre-treatment used.

Following disruption of the cells, cellular debris is removed, generally by centrifugation, and the intracellularly produced peptides or polypeptides are further purified, using standard purification techniques such as but not limited to, column chromatography, ion-exchange chromatography, size-exclusion chromatography, electrophoresis, HPLC, immunoadsorbent techniques, affinity chromatography, immunoprecipitation, and the like.

For example, one method for obtaining the intracellular peptides or polypeptides of the present invention involves affinity purification, such as by immunoaffinity chromatography using antibodies (e.g., previously generated antibodies), or by lectin affinity chromatography. Particularly preferred lectin resins are those that recognize mannose moieties such as but not limited to resins derived from *Galanthus nivalis* agglutinin (GNA), *Lens culinaris* agglutinin (LCA or lentil lectin), *Pisum sativum* agglutinin (PSA or pea lectin), *Narcissus pseudonarcissus* agglutinin (NPA) and *Allium ursinum* agglutinin (AUA). The choice of a suitable affinity resin is within the skill in the art. After affinity purification, the peptides or polypeptides can be further purified using conventional techniques well known in the art, such as by any of the techniques described above.

The NAC proteins, NAC peptides, and CCT1-NAC fusion proteins can be conveniently synthesized chemically, for example by any of several techniques that are known to those skilled in the peptide art. See, e.g., *Fmoc Solid Phase Peptide Synthesis: A Practical Approach* (W. C. Chan and Peter D. White eds., Oxford University Press, 1$^{St}$ edition, 2000); N. Leo Benoiton, *Chemistry of Peptide Synthesis* (CRC Press; 1$^{st}$ edition, 2005); *Peptide Synthesis and Applications* (*Methods in Molecular Biology*, John Howl ed., Humana Press, 1$^{st}$ ed., 2005); and *Pharmaceutical Formulation Development of Peptides and Proteins* (The Taylor & Francis Series in Pharmaceutical Sciences, Lars Hovgaard, Sven Frokjaer, and Marco van de Weert eds., CRC Press; 1$^{st}$ edition, 1999); herein incorporated by reference.

In general, these methods employ the sequential addition of one or more amino acids to a growing peptide chain. Normally, either the amino or carboxyl group of the first amino acid is protected by a suitable protecting group. The protected or derivatized amino acid can then be either attached to an inert solid support or utilized in solution by adding the next amino acid in the sequence having the complementary (amino or carboxyl) group suitably protected, under conditions that allow for the formation of an amide linkage. The protecting group is then removed from the newly added amino acid residue and the next amino acid (suitably protected) is then added, and so forth. After the desired amino acids have been linked in the proper sequence, any remaining protecting groups (and any solid support, if solid phase synthesis techniques are used) are removed sequentially or concurrently, to render the final peptide or polypeptide. By simple modification of this general procedure, it is possible to add more than one amino acid at a time to a growing chain, for example, by coupling (under conditions which do not racemize chiral centers) a protected tripeptide with a properly protected dipeptide to form, after deprotection, a pentapeptide. See, e.g., J. M. Stewart and J. D. Young, *Solid Phase Peptide Synthesis* (Pierce Chemical Co., Rockford, IL 1984) and G. Barany and R. B. Merrifield, *The Peptides: Analysis, Synthesis, Biology*, editors E. Gross and J. Meienhofer, Vol. 2, (Academic Press, New York, 1980), pp. 3-254, for solid phase peptide synthesis techniques; and M. Bodansky, *Principles of Peptide Synthesis*, (Springer-Verlag, Berlin 1984) and E. Gross and J. Meienhofer, Eds., *The Peptides: Analysis, Synthesis, Biology*, Vol. 1, for classical solution synthesis. These methods are typically used for relatively small polypeptides, i.e., up to about 50-100 amino acids in length, but are also applicable to larger polypeptides.

Typical protecting groups include t-butyloxycarbonyl (Boc), 9-fluorenylmethoxycarbonyl (Fmoc) benzyloxycarbonyl (Cbz); p-toluenesulfonyl (Tx); 2,4-dinitrophenyl; benzyl (Bzl); biphenylisopropyloxycarboxy-carbonyl, t-amyloxycarbonyl, isobornyloxycarbonyl, o-bromobenzyloxycarbonyl, cyclohexyl, isopropyl, acetyl, o-nitrophenylsulfonyl and the like.

Typical solid supports are cross-linked polymeric supports. These can include divinylbenzene cross-linked-styrene-based polymers, for example, divinylbenzene-hydroxymethylstyrene copolymers, divinylbenzene-chloromethylstyrene copolymers and divinylbenzene-benzhydrylaminopolystyrene copolymers.

The NAC proteins, NAC peptides, and CCT1-NAC fusion proteins can also be chemically prepared by other methods such as by the method of simultaneous multiple peptide synthesis. See, e.g., Houghten *Proc. Natl. Acad. Sci. USA* (1985) 82:5131-5135; U.S. Pat. No. 4,631,211.

Pharmaceutical Compositions

NAC proteins (i.e., comprising alpha and/or beta subunits of NAC), NAC peptides (i.e., comprising at least a portion of an N-terminal domain of a beta subunit of NAC) or CCT1-NAC fusion proteins (i.e., comprising a peptide comprising an apical domain of CCT1 connected to a peptide comprising at least a portion of an N-terminal domain of a beta subunit of NAC), as described herein, can be formulated into pharmaceutical compositions optionally comprising one or more pharmaceutically acceptable excipients. Exemplary excipients include, without limitation, carbohydrates, inorganic salts, antimicrobial agents, antioxidants, surfactants, buffers, acids, bases, and combinations thereof. Excipients suitable for injectable compositions include water, alcohols, polyols, glycerine, vegetable oils, phospholipids, and surfactants. A carbohydrate such as a sugar, a derivatized sugar such as an alditol, aldonic acid, an esterified sugar, and/or a sugar polymer may be present as an excipient. Specific carbohydrate excipients include, for example: monosaccharides, such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol, sorbitol (glucitol), pyranosyl sorbitol, myoinositol, and the like. The excipient can also include an inorganic salt or buffer such as citric acid, sodium chloride, potassium chloride, sodium sulfate, potassium nitrate, sodium phosphate monobasic, sodium phosphate dibasic, and combinations thereof.

A composition of the invention can also include an antimicrobial agent for preventing or deterring microbial growth. Nonlimiting examples of antimicrobial agents suitable for the present invention include benzalkonium chloride, benzethonium chloride, benzyl alcohol, cetylpyridinium chloride, chlorobutanol, phenol, phenylethyl alcohol, phenylmercuric nitrate, thimersol, and combinations thereof.

An antioxidant can be present in the composition as well. Antioxidants are used to prevent oxidation, thereby preventing the deterioration of the NAC proteins, NAC peptides, and CCT1-NAC fusion proteins, or other components of the preparation. Suitable antioxidants for use in the present invention include, for example, ascorbyl palmitate, butylated hydroxyanisole, butylated hydroxytoluene, hypophosphorous acid, monothioglycerol, propyl gallate, sodium bisulfite, sodium formaldehyde sulfoxylate, sodium metabisulfite, and combinations thereof.

A surfactant can be present as an excipient. Exemplary surfactants include: polysorbates, such as "Tween 20" and "Tween 80," and pluronics such as F68 and F88 (BASF, Mount Olive, New Jersey); sorbitan esters; lipids, such as phospholipids such as lecithin and other phosphatidylcholines, phosphatidylethanolamines (although preferably not in liposomal form), fatty acids and fatty esters; steroids, such as cholesterol; chelating agents, such as EDTA; and zinc and other such suitable cations.

Acids or bases can be present as an excipient in the composition. Nonlimiting examples of acids that can be used include those acids selected from the group consisting of hydrochloric acid, acetic acid, phosphoric acid, citric acid, malic acid, lactic acid, formic acid, trichloroacetic acid, nitric acid, perchloric acid, phosphoric acid, sulfuric acid, fumaric acid, and combinations thereof. Examples of suitable bases include, without limitation, bases selected from the group consisting of sodium hydroxide, sodium acetate, ammonium hydroxide, potassium hydroxide, ammonium acetate, potassium acetate, sodium phosphate, potassium phosphate, sodium citrate, sodium formate, sodium sulfate, potassium sulfate, potassium fumerate, and combinations thereof.

The amount of the NAC protein, NAC peptide, or CCT1-NAC fusion protein (e.g., when contained in a drug delivery system) in the composition will vary depending on a number of factors, but will optimally be a therapeutically effective dose when the composition is in a unit dosage form or container (e.g., a vial). A therapeutically effective dose can be determined experimentally by repeated administration of increasing amounts of the composition in order to determine which amount produces a clinically desired endpoint.

The amount of any individual excipient in the composition will vary depending on the nature and function of the excipient and particular needs of the composition. Typically, the optimal amount of any individual excipient is determined through routine experimentation, i.e., by preparing compositions containing varying amounts of the excipient (ranging from low to high), examining the stability and other parameters, and then determining the range at which optimal performance is attained with no significant adverse effects. Generally, however, the excipient(s) will be present in the composition in an amount of about 1% to about 99% by weight, preferably from about 5% to about 98% by weight, more preferably from about 15 to about 95% by weight of the excipient, with concentrations less than 30% by weight most preferred. These foregoing pharmaceutical excipients along with other excipients are described in "Remington: The Science & Practice of Pharmacy", 19th ed., Williams & Williams, (1995), the *"Physician's Desk Reference"*, 52nd ed., Medical Economics, Montvale, NJ (1998), and Kibbe, A. H., *Handbook of Pharmaceutical Excipients,* 3rd Edition, American Pharmaceutical Association, Washington, D.C., 2000.

The compositions encompass all types of formulations and in particular those that are suited for injection, e.g., powders or lyophilates that can be reconstituted with a solvent prior to use, as well as ready for injection solutions or suspensions, dry insoluble compositions for combination with a vehicle prior to use, and emulsions and liquid concentrates for dilution prior to administration. Examples of suitable diluents for reconstituting solid compositions prior to injection include bacteriostatic water for injection, dextrose 5% in water, phosphate buffered saline, Ringer's solution, saline, sterile water, deionized water, and combinations thereof. With respect to liquid pharmaceutical compositions, solutions and suspensions are envisioned. Additional preferred compositions include those for oral, ocular, or localized delivery.

The pharmaceutical preparations herein can also be housed in a syringe, an implantation device, or the like, depending upon the intended mode of delivery and use. Preferably, the compositions comprising one or more NAC proteins, NAC peptides, and/or CCT1-NAC fusion proteins described herein are in unit dosage form, meaning an amount of a conjugate or composition appropriate for a single dose, in a premeasured or pre-packaged form.

The compositions herein may optionally include one or more additional agents, such as other drugs for treating aggregation-associated diseases, or other medications used to treat a subject for a condition or disease. Compounded preparations may include a NAC protein (i.e., comprising alpha and/or beta subunits of NAC), a NAC peptide (i.e., comprising at least a portion of an N-terminal domain of a beta subunit of NAC) or a CCT1-NAC fusion protein (i.e., comprising a peptide comprising an apical domain of CCT1 connected to a peptide comprising at least a portion of an N-terminal domain of a beta subunit of NAC) and one or more drugs for treating an aggregation-associated disease, such as tetrabenazine, amantadine, neuroleptics (e.g., butyrophenones, diphenylbutylpiperidines, phenothiazines, thioxanthenes, benzamides, tricyclics, and benzisoxazoles/benzisothiazoles), benzodiazepines (e.g., alprazolam, flunitrazepam, chlordiazepoxide, clonazepam, diazepam, lorazepam, midazolam, oxazepam, and prazepam), cholinesterase inhibitors (e.g., Razadyne (galantamine), Exelon (rivastigmine), Aricept (donepezil), and Cognex (tacrine)), N-methyl D-aspartate (NMDA) antagonists (e.g., Namenda (memantine), remacemide), selective serotonin reuptake inhibitors (e.g., citalopram, escitalopram, fluoxetine, fluvoxamine, paroxetine, and sertraline), anticonvulsants (e.g., paraldehyde, stiripentol, barbiturates such as phenobarbital, methylphenobarbital, and barbexaclone, carboxamides such as carbamazepine, oxcarbazepine, and eslicarbazepine acetate, fatty acids such as valproates, vigabatrin, progabide, and tiagabine, fructose derivatives such as topiramate, gamma-aminobutyric acid (GABA) analogs such as gabapentin, pregabalin, vigabatrin, and progabide, and hydantoins such as ethotoin, phenytoin, mephenytoin, and fosphenytoin), or other medications. Alternatively, such agents can be contained in a separate composition from the composition comprising a NAC protein, NAC peptide, or CCT1-NAC fusion protein and co-administered concurrently, before, or after the composition comprising the NAC protein, NAC peptide, or CCT1-NAC fusion protein.

Administration

At least one therapeutically effective cycle of treatment with a NAC protein (i.e., comprising alpha and/or beta subunits of NAC), a NAC peptide (i.e., comprising at least a portion of an N-terminal domain of a beta subunit of NAC) or a CCT1-NAC fusion protein (i.e., comprising a peptide comprising an apical domain of CCT1 connected to a peptide comprising at least a portion of an N-terminal domain of a beta subunit of NAC) will be administered to a subject for treatment of a aggregation-associated disease. Aggregation-associated diseases include, but are not limited to, polyQ aggregation-associated diseases such as Huntington's disease, dentatorubropallidoluysian atrophy (DRPLA), spinal and bulbar muscular atrophy (SBMA) also known as Kennedy's disease, and spinocerebellar ataxia (SCA) including, but not limited to, SCA Type 1 (SCA1), SCA Type 2 (SCA2), SCA Type 3 (SCA3) or Machado-Joseph disease, SCA Type 6 (SCA6), SCA Type 7 (SCA7), and SCA Type 17 (SCA17); amyloid beta aggregation-associated diseases such as Alzheimer's disease; and synucleinopathies including, but are not limited to, Parkinson's disease, dementia with Lewy bodies, multiple system atrophy, and various neuroaxonal dystrophies.

By "therapeutically effective dose or amount" of a NAC protein (i.e., comprising alpha and/or beta subunits of NAC), a NAC peptide (i.e., comprising at least a portion of an N-terminal domain of a beta subunit of NAC) or a CCT1-NAC fusion protein (i.e., comprising a peptide comprising an apical domain of CCT1 connected to a peptide comprising at least a portion of an N-terminal domain of a beta subunit of NAC), as described herein, is intended an amount that, when administered, as described herein, brings about a positive therapeutic response, such as improved neurological recovery from an aggregation-associated disease such as a disease associated with polyQ aggregation, a disease associated with amyloid beta aggregation, or a disease associated with alpha-synuclein (i.e., synucleinopathy). Improved neurological recovery may include restored neuronal function, improved cognition, improved memory, or increased survival. In the case of a polyQ aggregation-associated disease, a therapeutically effective dose or amount of a NAC peptide or CCT1-NAC fusion protein may reduce polyQ protein aggregation and reduce formation of insoluble polyQ protein aggregates in the nuclei of neurons. In the case of an amyloid beta aggregation-associated disease (e.g., Alzheimer's disease), a therapeutically effective dose or amount" of a NAC protein may reduce amyloid beta aggregation and reduce formation of amyloid plaques in the brain. In the case of an alpha-synuclein aggregation-associated disease or synucleinopathy (e.g., Parkinson's disease), a therapeutically effective dose or amount" of a NAC protein may reduce aggregation of alpha-synuclein. Additionally, a therapeutically effective dose or amount may reduce accumulation of aggregates of alpha-synuclein in neurons, nerve fibers, and/or glial cells and reduce formation of Lewy bodies. In the case of an alpha-synuclein aggregation-associated disease or synucleinopathy (e.g., Parkinson's disease), a therapeutically effective dose or amount" of a NAC protein may reduce aggregation of alpha-synuclein. Additionally, a therapeutically effective dose or amount may reduce accumulation of aggregates of alpha-synuclein in neurons, nerve fibers, and/or glial cells and reduce formation of Lewy bodies.

In certain embodiments, multiple therapeutically effective doses of compositions comprising one or more NAC proteins, NAC peptides, or CCT1-NAC fusion proteins, and/or one or more other therapeutic agents, such as other drugs for treating aggregation-associated diseases, or other medications will be administered. The compositions of the present invention are typically, although not necessarily, administered orally, via injection (subcutaneously, intravenously, or intramuscularly), by infusion, or locally. Additional modes of administration are also contemplated, such as intracerebroventricular, intracerebral, intraneural, intraspinal, intralesion, intraparenchymatous, pulmonary, rectal, transdermal, transmucosal, intrathecal, pericardial, intra-arterial, intraocular, intraperitoneal, and so forth. In particular embodiments, compositions are administered into the brain, spinal cord, or cerebrospinal fluid of a subject.

The preparations according to the invention are also suitable for local treatment. In a particular embodiment, a composition of the invention is used for localized delivery of NAC protein, NAC peptide, or CCT1-NAC fusion protein, for example, for the treatment of an aggregation-associated disease. For example, compositions may be administered directly into a neuron or by stereotactic injection into the brain. The particular preparation and appropriate method of administration are chosen to target the NAC protein, NAC peptide, or CCT1-NAC fusion protein to the site of aberrant protein aggregation (e.g., insoluble polyQ protein aggregates in the nuclei of neurons or amyloid beta plaques in the brain).

The pharmaceutical preparation can be in the form of a liquid solution or suspension immediately prior to administration, but may also take another form such as a syrup, cream, ointment, tablet, capsule, powder, gel, matrix, suppository, or the like. The pharmaceutical compositions comprising one or more NAC proteins, NAC peptides, and/or CCT1-NAC fusion proteins and/or other agents may be administered using the same or different routes of administration in accordance with any medically acceptable method known in the art.

In another embodiment, the pharmaceutical compositions comprising one or more NAC proteins, NAC peptides, and/or CCT1-NAC fusion proteins and/or other agents are administered prophylactically, e.g., to prevent protein aggregation (e.g., polyQ or amyloid beta aggregation). Such prophylactic uses will be of particular value for subjects who have a genetic predisposition to developing an aggregation-associated disease. In another embodiment, the pharmaceutical compositions comprising one or more NAC proteins, NAC peptides, and/or CCT1-NAC fusion proteins and/or other agents are administered therapeutically to subjects with symptoms such as dementia, loss of mental acuity, or loss of muscle coordination caused by an aggregation-associated disease.

In another embodiment, the pharmaceutical compositions comprising one or more NAC proteins, NAC peptides, and/or CCT1-NAC fusion proteins and/or other agents are in a sustained-release formulation, or a formulation that is administered using a sustained-release device. Such devices are well known in the art, and include, for example, transdermal patches, and miniature implantable pumps that can provide for drug delivery over time in a continuous, steady-state fashion at a variety of doses to achieve a sustained-release effect with a non-sustained-release pharmaceutical composition.

The invention also provides a method for administering a conjugate comprising a NAC protein, NAC peptide, or CCT1-NAC fusion protein as provided herein to a patient suffering from an aggregation-associated disease or condition that is responsive to treatment with a NAC protein, NAC peptide, or CCT1-NAC fusion protein contained in the conjugate or composition. The method comprises administering, via any of the herein described modes, a therapeutically effective amount of the conjugate or drug delivery system, preferably provided as part of a pharmaceutical composition. The method of administering may be used to treat any condition that is responsive to treatment with a NAC protein, NAC peptide, or CCT1-NAC fusion protein.

Those of ordinary skill in the art will appreciate which conditions a specific NAC protein, NAC peptide, or CCT1-NAC fusion protein can effectively treat. The actual dose to be administered will vary depending upon the age, weight, and general condition of the subject as well as the particular aggregation-associated disease being treated, the severity of the condition being treated, the judgment of the health care professional, and the particular NAC protein, NAC peptide, or CCT1-NAC fusion protein or conjugate being administered. Therapeutically effective amounts can be determined by those skilled in the art, and will be adjusted to the particular requirements of each particular case.

In certain embodiments, multiple therapeutically effective doses of a NAC protein, NAC peptide, or CCT1-NAC fusion protein will be administered according to a daily dosing regimen or intermittently. For example, a therapeutically effective dose can be administered, one day a week, two days a week, three days a week, four days a week, or five days a week, and so forth. By "intermittent" administration is intended the therapeutically effective dose can be administered, for example, every other day, every two days, every three days, once a week, every other week, and so forth. For example, in some embodiments, a composition comprising a NAC protein, NAC peptide, or CCT1-NAC fusion protein will be administered once-weekly, twice-weekly or thrice-weekly for an extended period of time, such as for 1, 2, 3, 4, 5, 6, 7, 8 . . . 10 . . . 15 . . . 24 weeks, and so forth. By "twice-weekly" or "two times per week" is intended that two therapeutically effective doses of the agent in question is administered to the subject within a 7 day period, beginning on day 1 of the first week of administration, with a minimum of 72 hours, between doses and a maximum of 96 hours between doses. By "thrice weekly" or "three times per week" is intended that three therapeutically effective doses are administered to the subject within a 7 day period, allowing for a minimum of 48 hours between doses and a maximum of 72 hours between doses. For purposes of the present disclosure, this type of dosing is referred to as "intermittent" therapy. In accordance with the methods described herein, a subject can receive intermittent therapy (i.e., once-weekly, twice-weekly or thrice-weekly administration of a therapeutically effective dose) for one or more weekly cycles until the desired therapeutic response is achieved. The agents can be administered by any acceptable route of administration as noted herein below. The amount administered will depend on the potency of the specific NAC protein, NAC peptide, or CCT1-NAC fusion protein, the particular aggregation-associated disease that is treated, the magnitude of the effect desired, and the route of administration.

A purified NAC protein, NAC peptide, or CCT1-NAC fusion protein (again, preferably provided as part of a pharmaceutical preparation) can be administered alone or in combination with one or more other therapeutic agents, such as tetrabenazine, amantadine, neuroleptics (e.g., butyrophenones, diphenylbutylpiperidines, phenothiazines, thioxanthenes, benzamides, tricyclics, and benzisoxazoles/benzisothiazoles), benzodiazepines (e.g., alprazolam, flunitrazepam, chlordiazepoxide, clonazepam, diazepam, lorazepam, midazolam, oxazepam, and prazepam), cholinesterase inhibitors (e.g., Razadyne (galantamine), Exelon (rivastigmine), Aricept (donepezil), and Cognex (tacrine)), N-methyl D-aspartate (NMDA) antagonists (e.g., Namenda (memantine), remacemide), selective serotonin reuptake inhibitors (e.g., citalopram, escitalopram, fluoxetine, fluvoxamine, paroxetine, and sertraline), anticonvulsants (e.g., paraldehyde, stiripentol, barbiturates such as phenobarbital, methylphenobarbital, and barbexaclone, carboxamides such as carbamazepine, oxcarbazepine, and eslicarbazepine acetate, fatty acids such as valproates, vigabatrin, progabide, and tiagabine, fructose derivatives such as topiramate, gamma-aminobutyric acid (GABA) analogs such as gabapentin, pregabalin, vigabatrin, and progabide, and hydantoins such as ethotoin, phenytoin, mephenytoin, and fosphenytoin), or other medications used to treat a particular condition or disease according to a variety of dosing schedules depending on the judgment of the clinician, needs of the patient, and so forth. The specific dosing schedule will be known by those of ordinary skill in the art or can be determined experimentally using routine methods. Exemplary dosing schedules include, without limitation, administration five times a day, four times a day, three times a day, twice daily, once daily, three times weekly, twice weekly, once weekly, twice monthly, once monthly, and any combination thereof. Preferred compositions are those requiring dosing no more than once a day.

A NAC protein, NAC peptide, or CCT1-NAC fusion protein can be administered prior to, concurrent with, or subsequent to other agents. If provided at the same time as other agents, one or more NAC proteins, NAC peptides, and/or CCT1-NAC fusion proteins can be provided in the same or in a different composition. Thus, one or more NAC proteins, NAC peptides, and/or CCT1-NAC fusion proteins and/or other agents can be presented to the individual by way of concurrent therapy. By "concurrent therapy" is intended administration to a subject such that the therapeutic effect of the combination of the substances is caused in the subject undergoing therapy. For example, concurrent therapy may be achieved by administering a dose of a pharmaceutical composition comprising a NAC protein, NAC peptide, or CCT1-NAC fusion protein and a dose of a pharmaceutical composition comprising at least one other agent, such as another drug for treating an aggregation-associated disease (e.g., a polyQ or amyloid beta aggregation disease), which in combination comprise a therapeutically effective dose, according to a particular dosing regimen. Similarly, one or more NAC proteins, NAC peptides, or CCT1-NAC fusion proteins and one or more other therapeutic agents can be administered in at least one therapeutic dose. Administration of the separate pharmaceutical compositions can be performed simultaneously or at different times (i.e., sequentially, in either order, on the same day, or on different days), as long as the therapeutic effect of the combination of these substances is caused in the subject undergoing therapy.

Kits

Also provided are kits for treating a patient for an aggregation-associated disease with a NAC protein, NAC peptide, and/or CCT1-NAC fusion protein as described herein. The NAC protein, NAC peptide, or CCT1-NAC fusion protein and optionally other therapeutic agents may be contained in separate compositions or in the same composition. Kits may include unit doses of the formulations comprising the NAC protein, NAC peptide, or CCT1-NAC fusion protein suitable for use in the treatment methods described herein, e.g., in tablets or injectable dose(s). In such kits, in addition to the containers containing the unit doses will be an informational package insert describing the use and attendant benefits of the treatment for an aggregation-associated disease. The kit can include, for example, a dosing regimen for the NAC protein, NAC peptide, or CCT1-NAC fusion protein.

Formulations suitable for intravenous administration are of particular interest, and in such embodiments the kit may further include a syringe or other device to accomplish such administration, which syringe or device may be pre-filled with the NAC protein, NAC peptide, or CCT1-NAC fusion protein. The instructions can be printed on a label affixed to the container or can be a package insert that accompanies the container.

In some embodiments, the kit includes a NAC peptide comprising at least a portion of an N-terminal domain of a beta subunit of NAC, wherein the peptide suppresses aggregation of a protein comprising a polyQ sequence. The NAC peptide will generally comprise at least a C-terminal portion of the N-terminal domain corresponding to amino acid residues 23 to 38 numbered relative to the reference sequence of SEQ ID NO:1. In some embodiments, the peptide comprises the entire N-terminal domain. In certain embodiments, the kit comprises a NAC peptide comprising an amino acid sequence selected from the group consisting of SEQ ID NOS:1-3, or sequences displaying at least about 80-100% sequence identity thereto, including any percent identity within this range, such as 81, 82, 83, 84, 85, 86, 87, 88, 89, 90, 91, 92, 93, 94, 95, 96, 97, 98, 99% sequence identity thereto, wherein the peptide is capable of suppressing aggregation of a protein comprising a polyQ sequence. A subject kit may include at least one container comprising a solution comprising a unit dose of the NAC peptide, and a pharmaceutically acceptable excipient; and instructions to administer a unit dose according to a desired regimen or exemplary regimen dependent upon the particular polyQ aggregation disease being treated, age, weight, and the like.

In some embodiments, the kit includes a CTT1-NAC fusion protein. The fusion protein will generally comprise at least the apical domain of CCT1 connected to a NAC peptide comprising at least a portion of an N-terminal domain of a beta subunit of NAC, as described herein, wherein the fusion protein is capable of suppressing aggregation of a protein comprising a polyQ sequence (e.g., polyQ-expanded huntingtin exon1). In certain embodiments, the kit comprises a fusion protein comprising an amino acid sequence of SEQ ID NO:8, or a sequence displaying at least about 80-100% sequence identity thereto, including any percent identity within this range, such as 81, 82, 83, 84, 85, 86, 87, 88, 89, 90, 91, 92, 93, 94, 95, 96, 97, 98, 99% sequence identity thereto, wherein the fusion protein suppresses aggregation of a protein comprising a polyQ sequence (e.g., polyQ-expanded huntingtin exon1). A subject kit may include at least one container comprising a solution comprising a unit dose of the CTT1-NAC fusion protein, and a pharmaceutically acceptable excipient; and instructions to administer a unit dose according to a desired regimen or exemplary regimen age, weight, and the like for treatment of Huntington's disease.

In some embodiments, the kit includes a NAC protein that suppresses aggregation of one or more amyloid beta peptides selected from the group consisting of Aβ36, Aβ37, Aβ38, Aβ39, Aβ40, Aβ41, Aβ42, and Aβ43. A subject kit may include at least one container comprising a solution comprising a unit dose of the NAC protein, and a pharmaceutically acceptable excipient; and instructions to administer a unit dose according to a desired regimen or exemplary regimen dependent upon the age, weight, and the like for treatment of Alzheimer's disease.

In some embodiments, the kit includes a NAC protein that suppresses aggregation of alpha-synuclein. A subject kit may include at least one container comprising a solution comprising a unit dose of the NAC protein, and a pharmaceutically acceptable excipient; and instructions to administer a unit dose according to a desired regimen or exemplary regimen dependent upon the age, weight, and the like for treatment of synucleinopathy (e.g., Parkinson's disease).

It will be apparent to one of ordinary skill in the art that various changes and modifications can be made without departing from the spirit or scope of the invention.

EXPERIMENTAL

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

All publications and patent applications cited in this specification are herein incorporated by reference as if each individual publication or patent application were specifically and individually indicated to be incorporated by reference.

The present invention has been described in terms of particular embodiments found or proposed by the present inventor to comprise preferred modes for the practice of the invention. It will be appreciated by those of skill in the art that, in light of the present disclosure, numerous modifications and changes can be made in the particular embodiments exemplified without departing from the intended scope of the invention. For example, due to codon redundancy, changes can be made in the underlying DNA sequence without affecting the protein sequence. Moreover, due to biological functional equivalency considerations, changes can be made in protein structure without affecting the biological action in kind or amount. All such modifications are intended to be included within the scope of the appended claims.

Example 1

Dual Role of Ribosome-Binding Domain of NAC as a Potent Suppressor of Protein Aggregation and Aging-Related Proteinopathies

INTRODUCTION

A multifaceted chaperone network guards the integrity of the cellular proteome. This network comprises various conserved families of molecular chaperones operating in all cellular sub-compartments to promote the folding and function of their protein substrates and counteract proteotoxicity provoked by protein misfolding and aggregation (Kim et al., 2013). A subset of molecular chaperones is specialized for de novo protein folding, including the ribosome-associated complex (RAC) in eukaryotes or Trigger factor in bacteria. These systems directly bind to translating ribosomes near the peptide exit tunnel to engage their substrates in a co-translational manner. Installed at the ribosome, they are enabled to assist protein folding at the earliest possible time when nascent chains are just reaching the cytoplasm. These chaperones thus lay the groundwork for the maintenance of protein homeostasis in the cell (Pechmann et al., 2013; Preissler and Deuerling, 2012).

A major factor in eukaryotes that quantitatively associates with translating ribosomes near the peptide exit site is the ubiquitous nascent polypeptide-associated complex (NAC)

(Wiedmann et al., 1994). It consists of two different subunits, αNAC and βNAC, that dimerize when their homologous NAC domains form a semi-β-barrel core (Liu et al., 2010; Wang et al., 2010). NAC is an abundant complex expressed at least equimolar relative to ribosomes; thus, most translating ribosomes likely associate with NAC (del Alamo et al., 2011; Raue et al., 2007). Essential for ribosome binding is a ~40 aa domain found specifically in the N-terminus of the βNAC subunit (herein N-βNAC). N-βNAC is highly conserved and exhibits a characteristic positive net charge. Deletion of either the first N-terminal 11 amino acids or mutation of a conserved positively charged central motif (RRKxxKK) abolishes ribosome binding in yeast, suggesting that this domain mediates the main ribosomal contact of NAC (Pech et al., 2010; Wegrzyn et al., 2006).

Because of its localization at the ribosomal tunnel exit, a proposed function of NAC is to act as a co-translational molecular chaperone similar to the ATP-independent Trigger factor in bacteria. However, only indirect evidence supports this assumption and mechanistic details of the proposed chaperone activity are entirely unknown (Duttler et al., 2013; Kirstein-Miles et al., 2013; Ott et al., 2015; Wang et al., 2013). Crosslinking data suggest that both NAC subunits can interact with protein clients, but the particular substrate binding site(s) of α- and βNAC and the substrate binding specificity are unknown (Martin et al., 2018; Wang et al., 1995). Further, whether NAC has a function aside from its co-translational ribosomal role is unknown.

Here, we conducted a series of in vitro and in vivo experiments to explore the potential chaperone function of NAC in greater detail. We found that NAC directly exerts chaperone activity as a holdase toward a set of structurally and physicochemically diverse model substrates. NAC effectively suppresses aggregation of disease-related polyQ-expanded proteins and Amyloid-β 40 (Aβ40) peptides, as well as denatured firefly luciferase, independent from its ribosome association. Specifically, our data reveal that the ribosome-binding domain in the N-terminus of βNAC represents a central chaperone domain of NAC. Moreover, we found that NAC enhances organismal fitness of PolyQ-expressing C. elegans animals and prevents proteostasis collapse and cell death of neurons expressing PolyQ-expanded Huntingtin. These data suggest that NAC is a chaperone that acts as a potent modifier of age-related proteinopathies.

Results

NAC Suppresses Aggregation of Diverse PolyQ Proteins

Figure 1B:
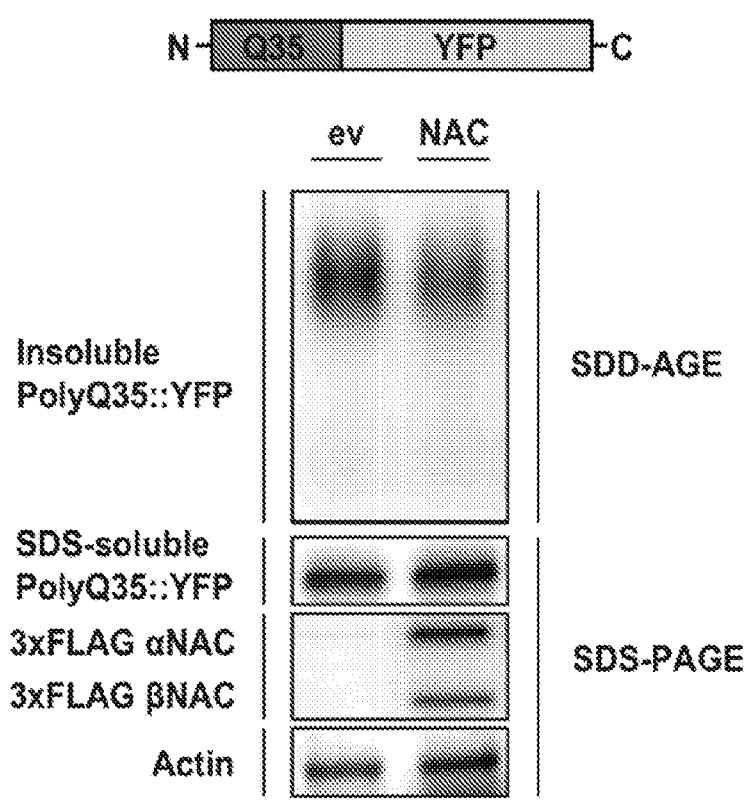
Figure 7A:
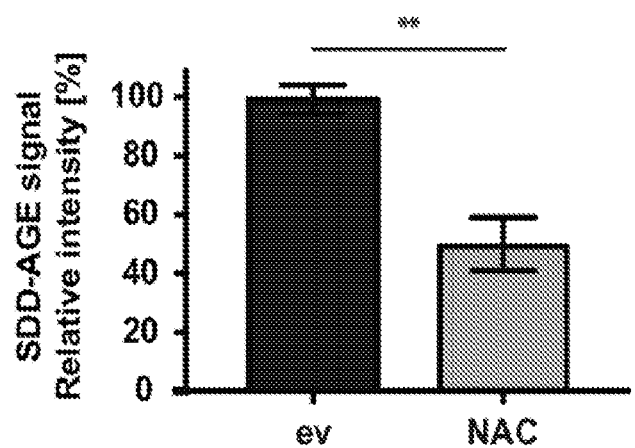
FIGS. 7A-7D show aggregation suppression of mutant Huntingtin by NAC.

NAC is a major ribosome-binding factor interacting broadly with nascent chains (del Alamo et al., 2011). However, its assumed chaperone function is poorly investigated. A previous study in C. elegans showed that depletion of NAC leads to increased aggregation of a model polyglutamine (PolyQ) protein (Kirstein-Miles et al., 2013). Although loss of NAC causes pleiotropic defects in C. elegans (Gamerdinger et al., 2015), this finding raises the possibility that NAC directly exerts a chaperone function on aggregation-prone proteins. In this case, overexpression of NAC should prevent aggregation of PolyQ proteins in vivo. Therefore, we used a C. elegans strain expressing 35 consecutive glutamine residues fused to YFP (PolyQ35::YFP) in body wall muscle cells. This PolyQ length is close to the aggregation threshold in C. elegans muscle cells, leading to progressive, age-dependent aggregation starting at day 2 of adulthood (Morley et al., 2002). We generated transgenic animals that overexpress FLAG-tagged α- and βNAC under the control of the muscle-specific myo-3 promoter. PolyQ aggregation was assessed at day 3 of adulthood by fluorescence microscopy as well as semi-denaturing detergent agarose gel electrophoresis (SDD-AGE), which detects high molecular weight oligomeric PolyQ species (Halfmann and Lindquist, 2008). The overexpression of NAC did not alter the overall morphology of C. elegans and expression levels of PolyQ35::YFP (FIG. 1A, whole body images). However, we found that overexpression of NAC effectively suppressed PolyQ35::YFP aggregation in worms. This is evident by magnification of the head regions showing diffuse PolyQ35::YFP and less punctate PolyQ35::YFP structures when NAC was overexpressed (FIG. 1A, head region images). Consistent with the fluorescence microscopy analysis, we found less insoluble high molecular weight aggregate species in NAC overexpressing worms by SDD-AGE analysis (FIG. 1B and FIG. 7A). These data indicate that NAC is a modifier of PolyQ aggregation. To directly test the potential chaperone function of NAC, we employed a peptide composed of 51 consecutive glutamines (PolyQ51) as a model substrate in a well-established in vitro aggregation assay. We initiated aggregation of PolyQ51 by cleaving a solubilizing GST tag with TEV protease and detected aggregates over time using a filter trap assay. Addition of purified human NAC strongly delayed the accumulation of PolyQ51 aggregates (FIG. 1C, D), suggesting that NAC directly acts on the polyglutamine stretch and slows the rate of aggregation.

Figure 1C:
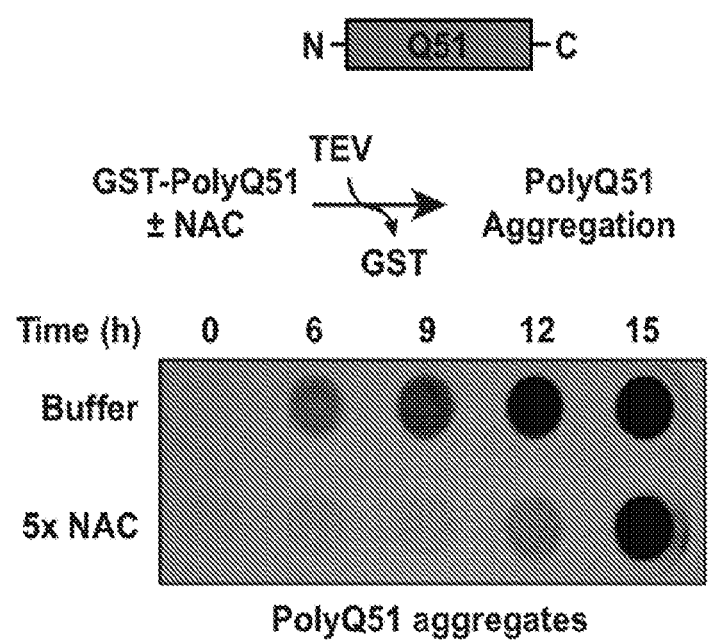
Figure 1D:
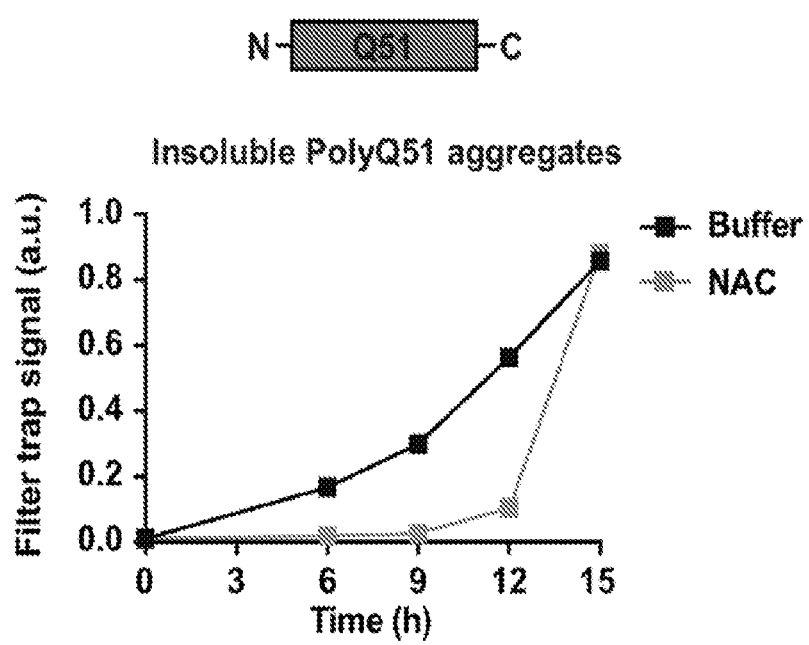
Figure 1E:
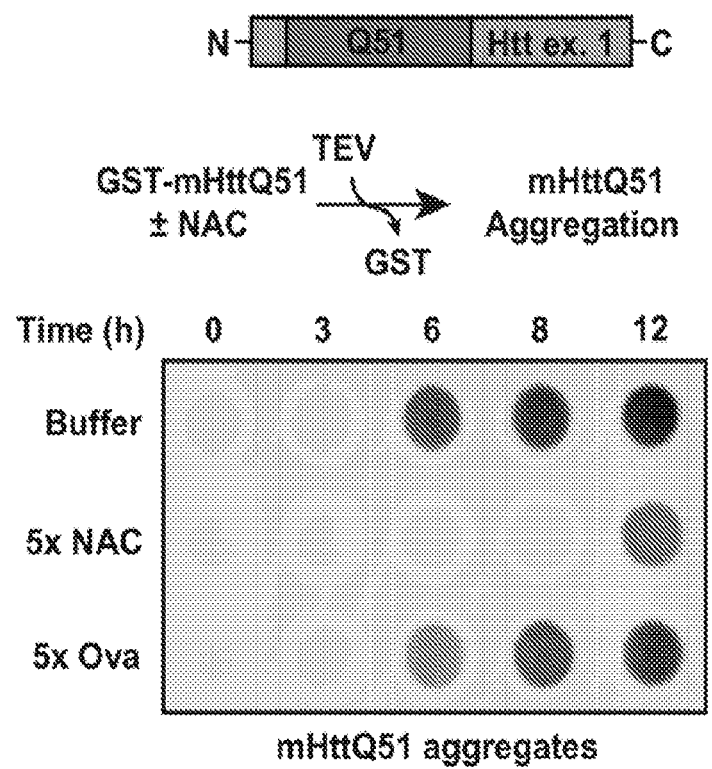
Figure 1F:
Figure 1F:
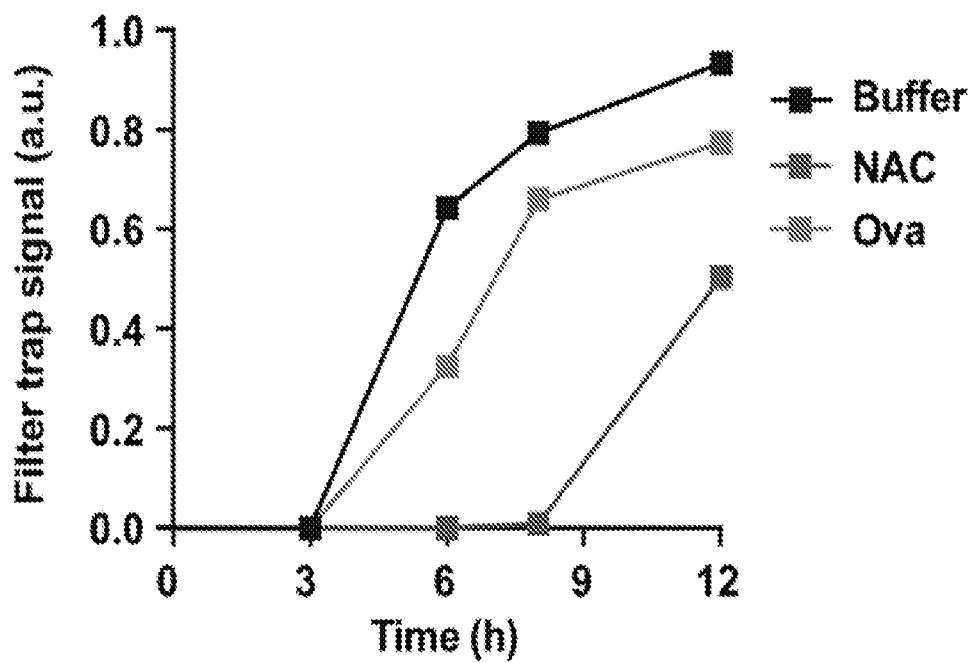
Figure 7B:
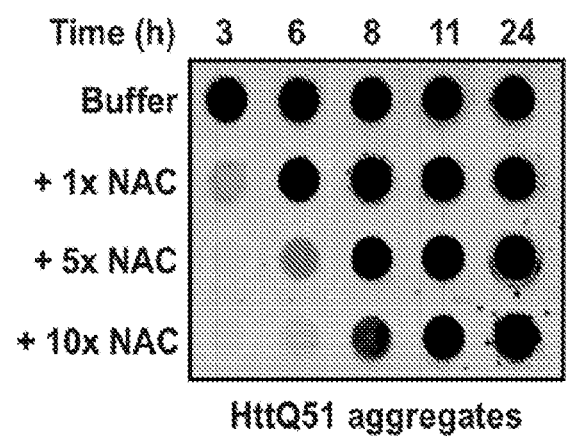
Figure 7C:
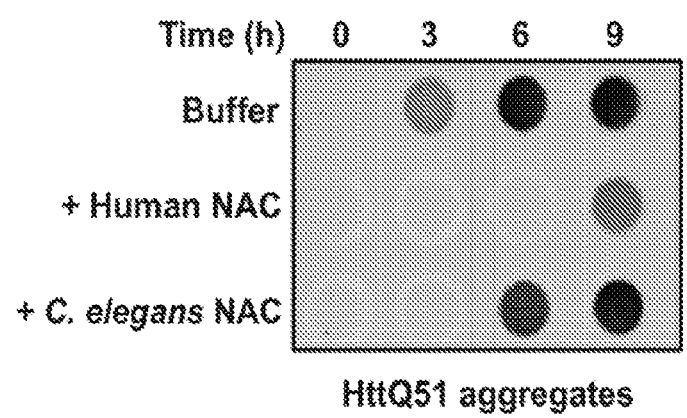

The aggregation suppression effect of NAC on the pure PolyQ substrate predicts that NAC may also inhibit aggregation of pathogenic proteins harboring an extended PolyQ tract. Thus, we investigated whether NAC prevents aggregation of mutant Huntingtin exon 1, the causative agent in the human neurodegenerative disorder Huntington's disease (HD) (Labbadia and Morimoto, 2013). Using the same in vitro filter trap aggregation assay, we found that human NAC effectively suppressed aggregation of mutant Huntingtin exon 1 containing a pathogenic stretch of 51 glutamines (mHttQ51), whereas a molar equivalent ovalbumin control showed little effect (FIG. 1E, F). Aggregation suppression of mHttQ51 by NAC was concentration dependent (FIG. 7B) and also observed, albeit to a lesser extent, with the C. elegans form of NAC (FIG. 7C). Moreover, we found that NAC did not disaggregate preformed mHttQ51 aggregates in vitro (FIG. 7D), suggesting that NAC exhibits a holdase function on early aggregation species to prevent further oligomerization, similar to the apical domain of the chaperonin TRiC (Tam et al., 2006).

Figure 2A:
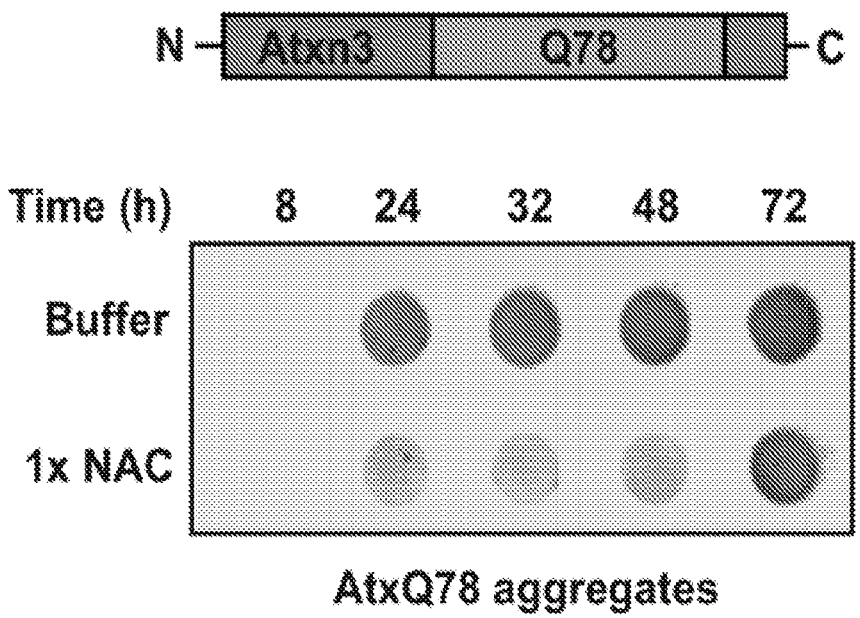
FIGS. 2A-2C show that NAC suppresses aggregation of mutant Ataxin-3.
Figure 2B:
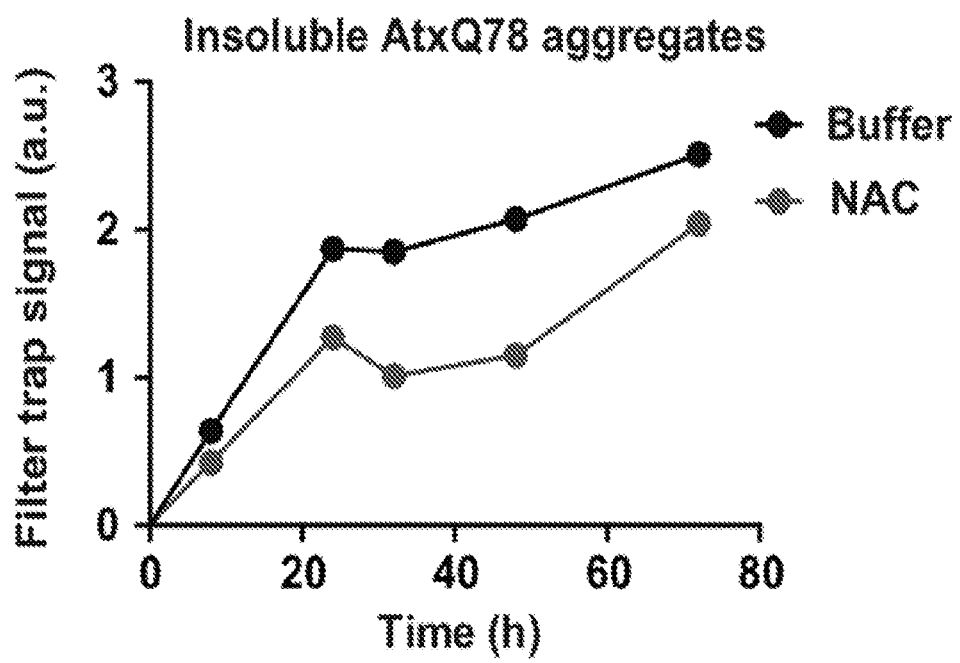
Figure 8A:
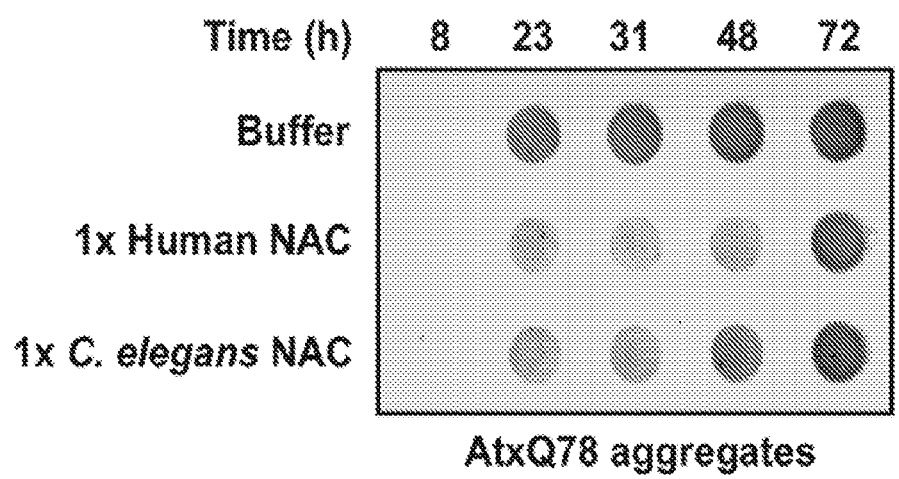
FIGS. 8A-8C show interaction of NAC with mutant Ataxin-3.

A second pathogenic PolyQ substrate tested was full-length Ataxin-3 harboring a stretch of 78 glutamines (AtxQ78), which causes Spinocerebellar ataxia-3 (SCA3) in humans (Matos et al., 2011). Importantly, this protein shares no homology with Huntingtin exon 1 aside from the mutant expansion of a PolyQ repeat and aggregates via a separate kinetic mechanism (Saunders and Bottomley, 2009; Scarff et al., 2015). AtxQ78 exhibits lower aggregation propensity compared to PolyQ51 and mHttQ51 circumventing the requirement of a solubilizing tag. To assess whether NAC also affects AtxQ78 aggregation, we incubated the AtxQ78 substrate in the presence or absence of purified human NAC at 37° C. and assessed aggregation by a filter trap assay. Similar to the effect on PolyQ51 and mHttQ51, addition of human NAC delayed the aggregation of AtxQ78 (FIG. 2A, B). The C. elegans NAC homolog also prevented AtxQ78 aggregation but was slightly less effective than the human isoform (FIG. 8A).

Figure 2C:
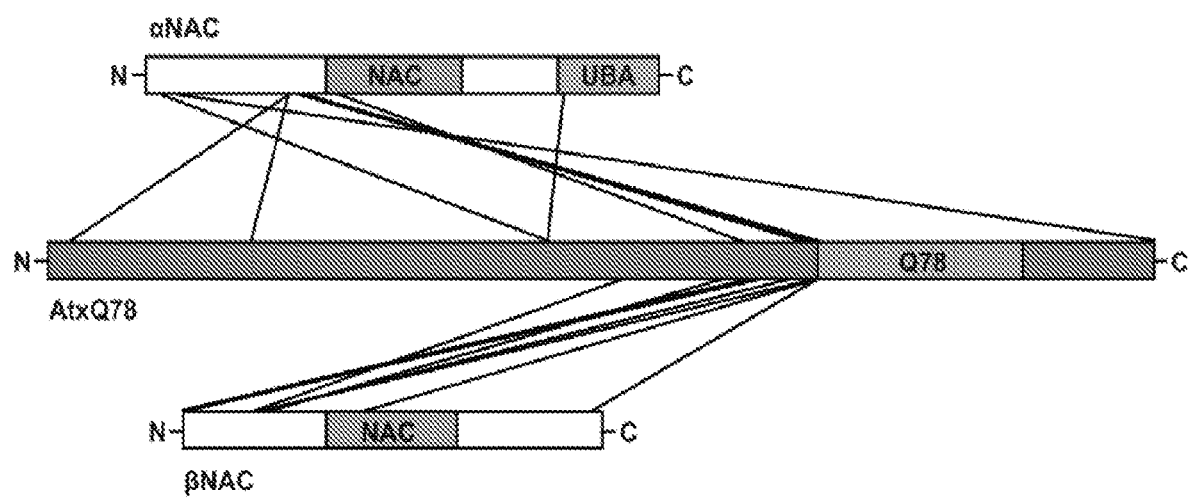
Figure 8B:
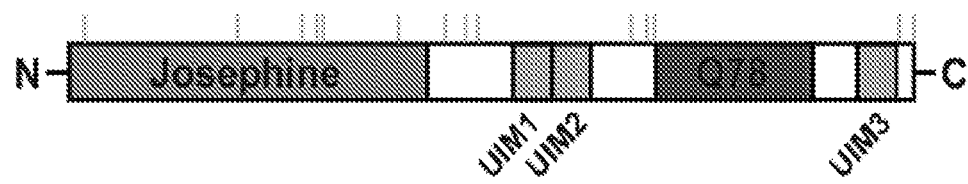
Figure 8C:
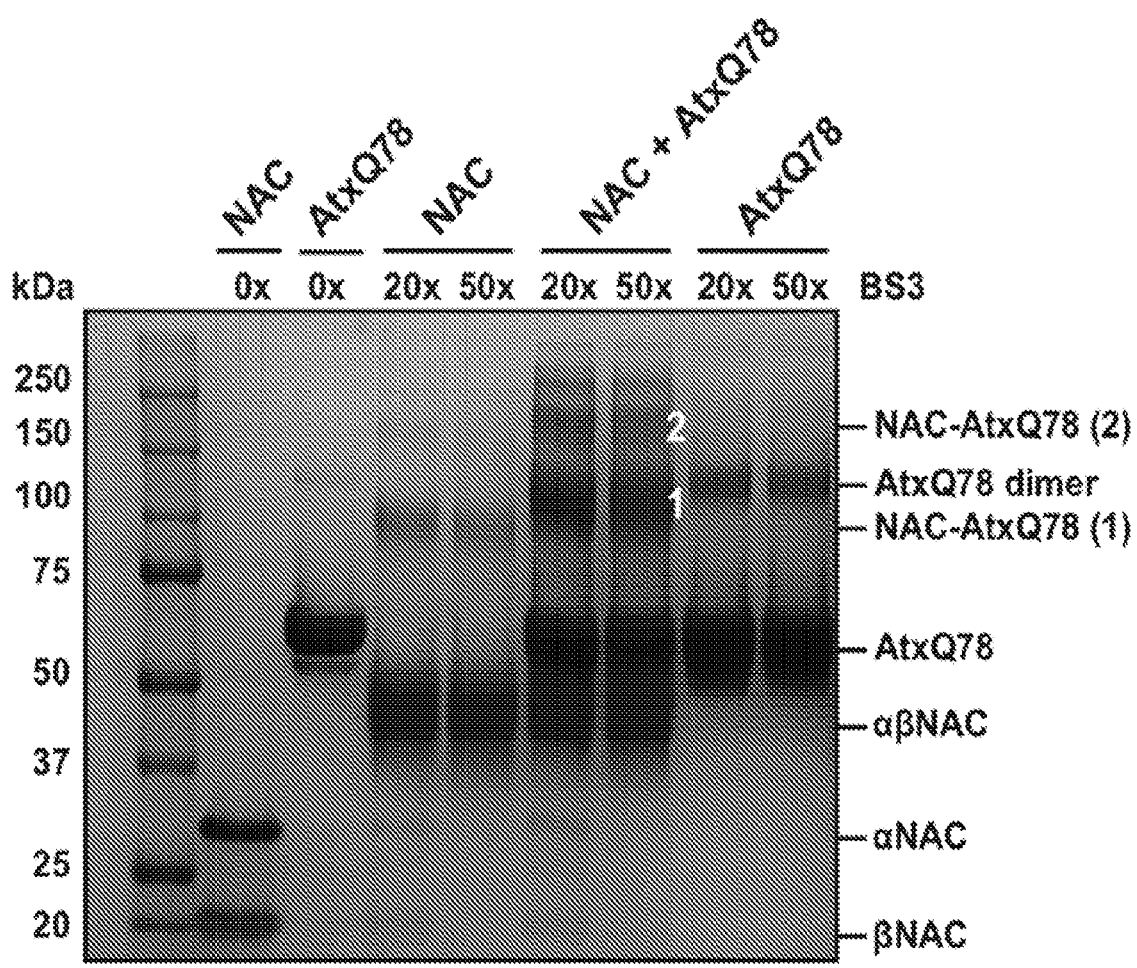

Next, we mapped the PolyQ substrate binding site in NAC using a crosslinking-MS approach. We used full-length AtxQ78 as our PolyQ model substrate for crosslinking to NAC for several reasons. First, AtxQ78 exhibits lower aggregation propensity than mHttQ51 or PolyQ51, allowing for crosslinking without concern for increasing the rate of the aggregation reaction. Second, the AtxQ78 construct does not require use of a solubilizing tag avoiding the presence of additional factors during the crosslinking reaction. Third, while NAC may directly interact with the PolyQ region, glutamine does not contain any optimal functional groups for chemical crosslinking. However, AtxQ78 has many lysine residues, including several directly up-stream of the polyglutamine region, facilitating chemical crosslinking with amine-reactive crosslinkers (FIG. 8B). Thus, crosslinks that occur within NAC to AtxQ78 regions adjacent to the polyglutamine tract may reflect the direct interaction between NAC and the PolyQ region which we observed in vitro (FIGS. 1C, 1D). We incubated AtxQ78 with human NAC and used the amine-reactive homobifunctional cross-linker $BS^3$ to trap transient chaperone interactions. Crosslinked NAC-AtxQ78 complexes visible on Coomassie-stained gels (FIG. 8C) were excised and crosslinked peptides were identified by LC-MS using StavroX (Gotze et al., 2012). Strikingly, 11 out of 18 identified intermolecular crosslinks were to the C-terminal region of AtxQ78 close to the expanded PolyQ stretch (FIG. 2C, Table 1). These data suggest that NAC acts by binding at, or close to, the PolyQ tract to suppress aggregation of AtxQ78, which agrees with the observed NAC effect on the pure PolyQ51 substrate (FIGS. 1C, 1D). Interestingly, NAC predominantly cross-linked to AtxQ78 via the N-terminal regions of αNAC and βNAC (FIG. 2C, Table 1), suggesting that a crucial PolyQ binding site is located in these domains. However, single crosslinks were also identified to the NAC domains, the UBA domain of αNAC, as well as to the C-terminal domain of βNAC.

The Ribosome-Binding Domain of NAC Exerts Chaperone Activity

Figure 3A:
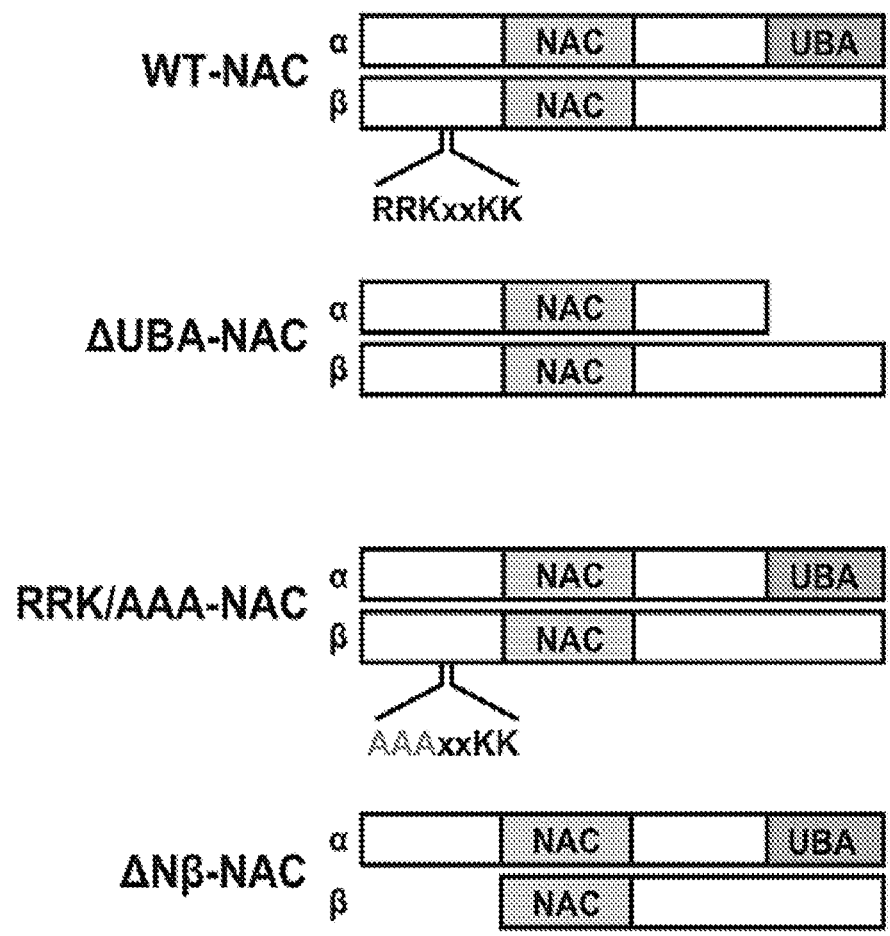
FIGS. 3A-3E show that the ribosome-binding domain of NAC exerts chaperone activity.
Figure 3B:
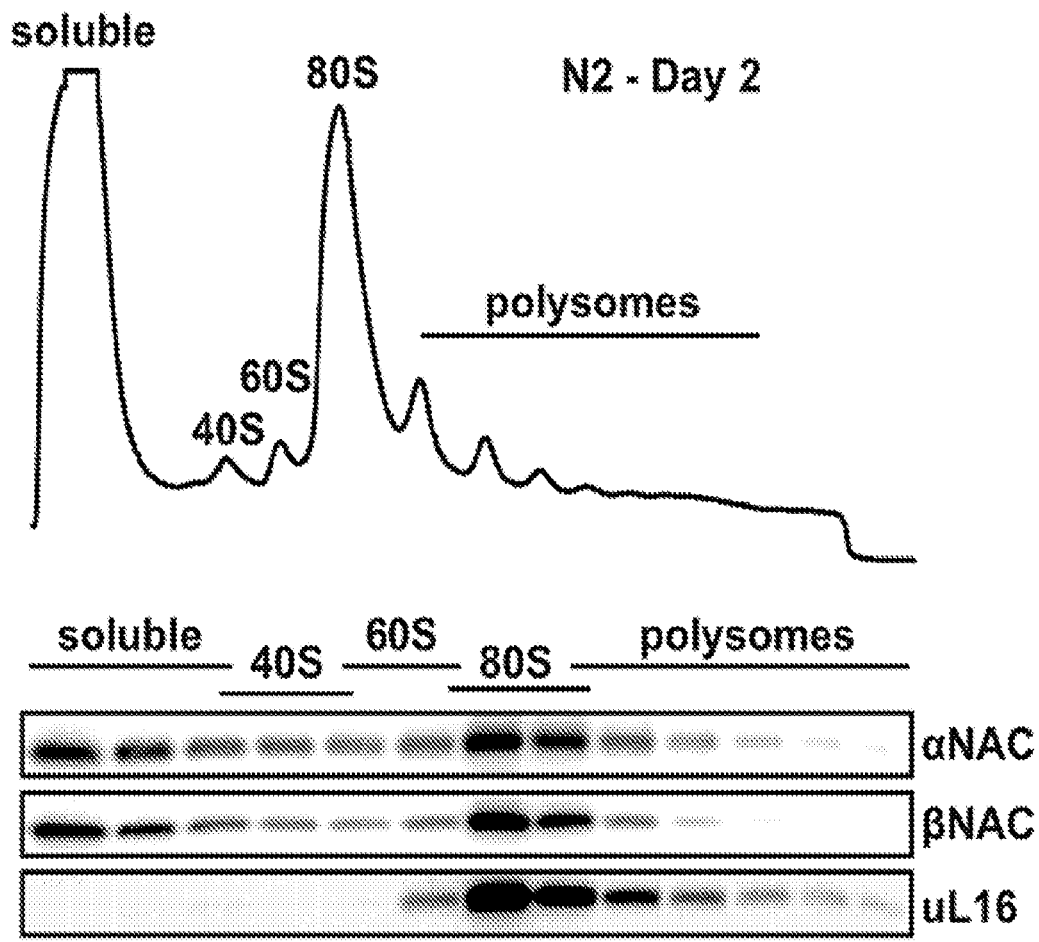
Figure 3C:
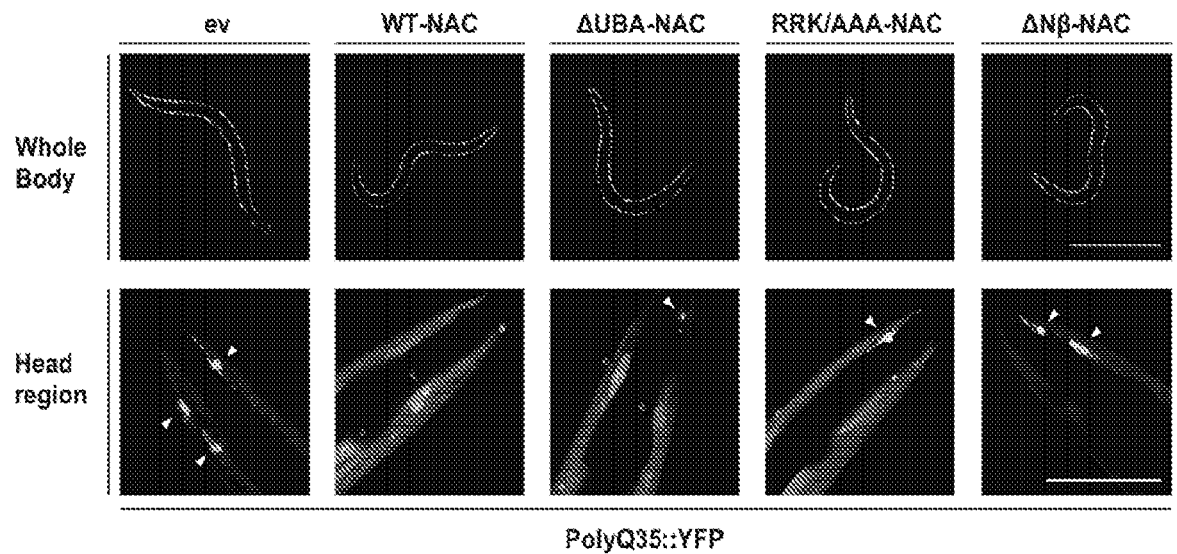
Figure 3D:
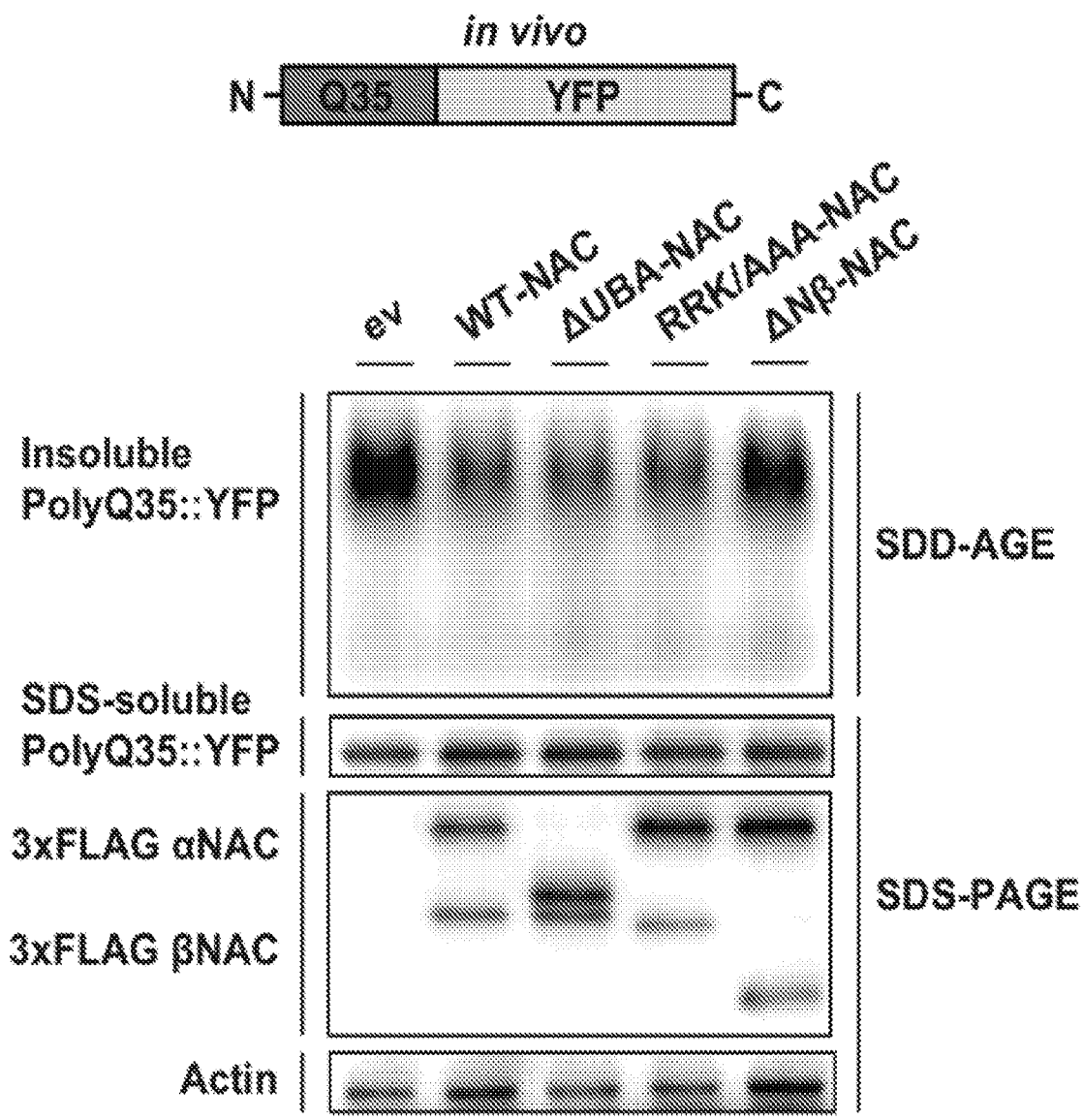
Figure 9A:
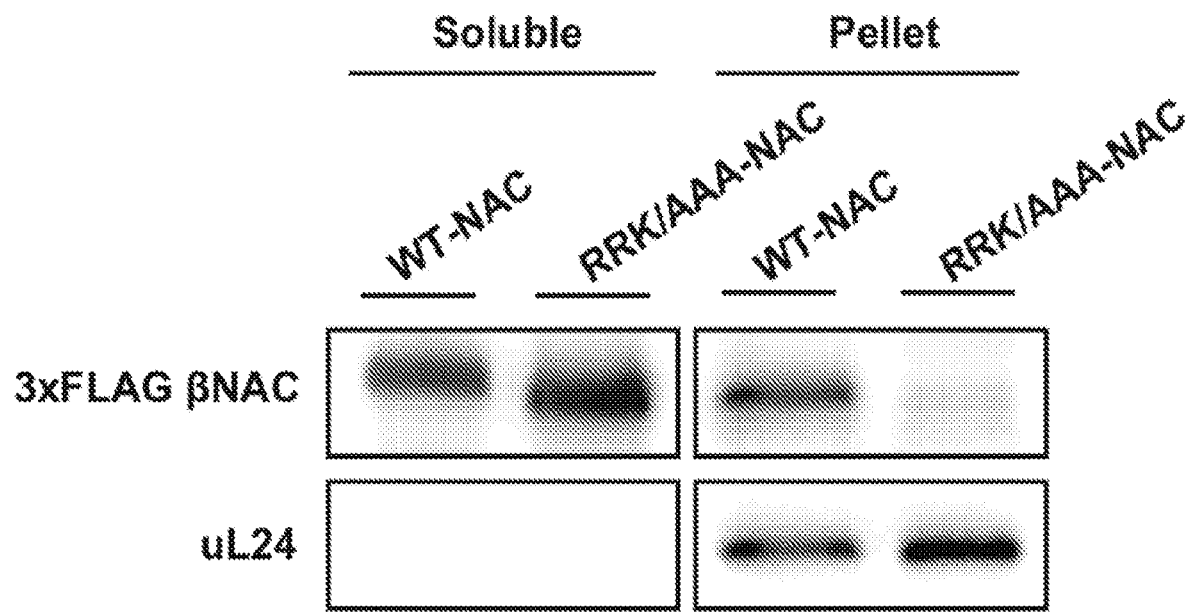
FIGS. 9A and 9B show that RRK/AAA-NAC does not bind to ribosomes in vivo.
Figure 9B:
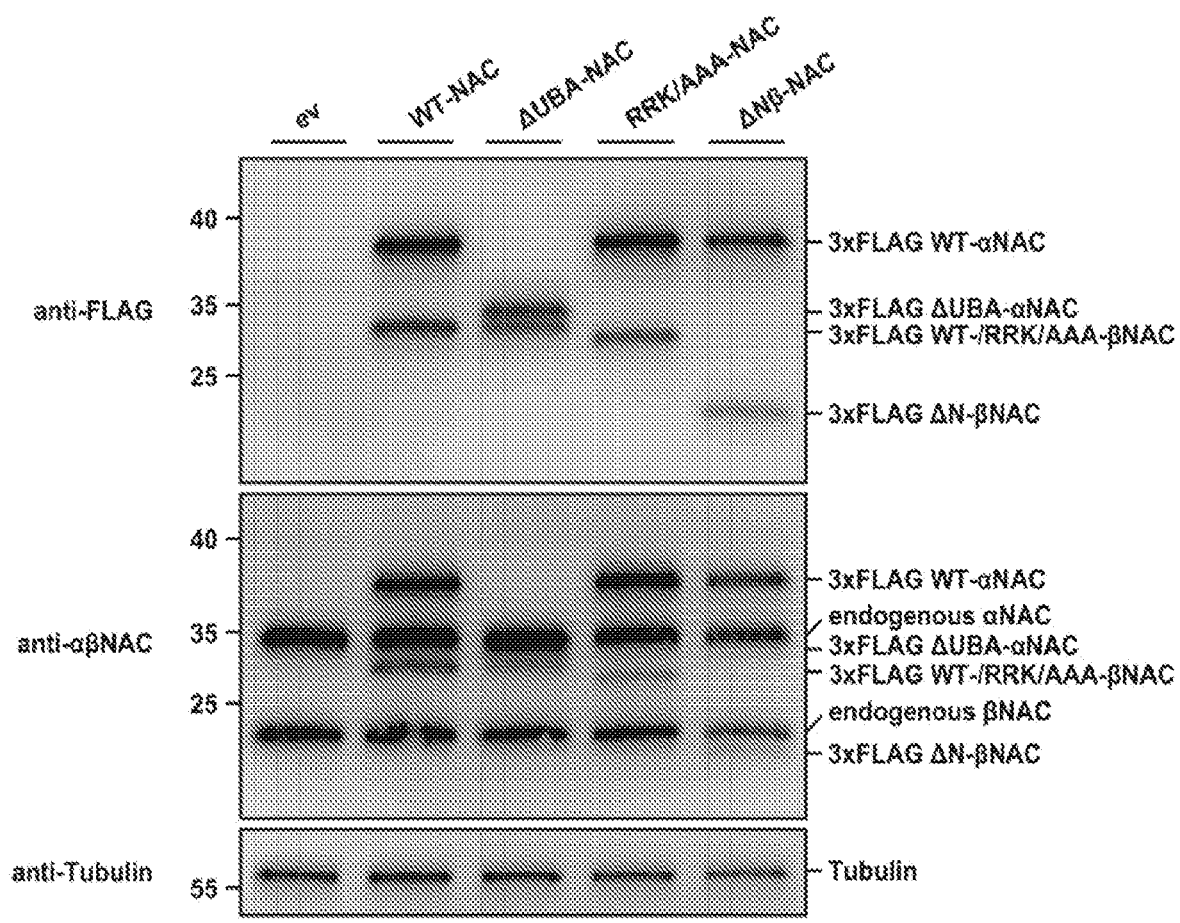
Figure 10:
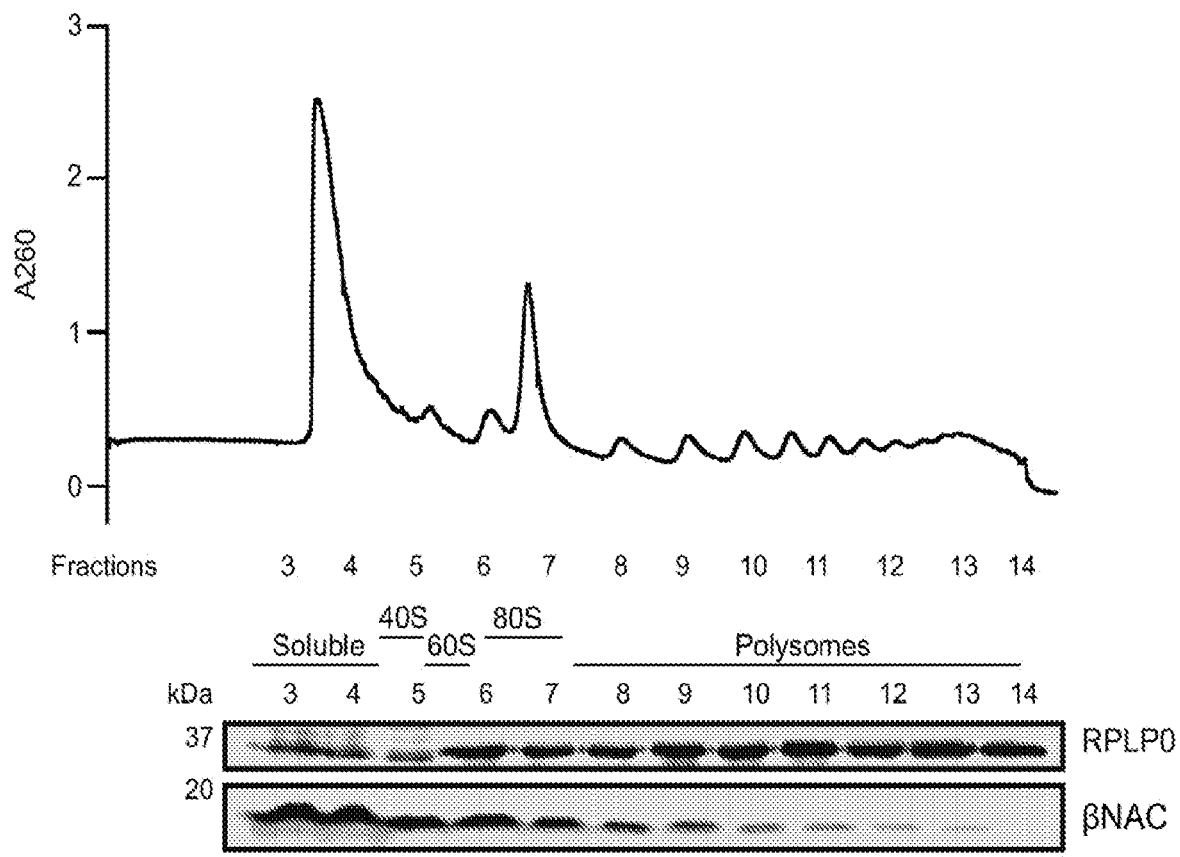
FIG. 10 shows a large fraction of NAC is non-ribosome-associated in human cells. (Top) Polysome profile of HEK293T cells. (Bottom) βNAC levels were assessed with immunoblotting. RPLP0 served as loading control.

Our data show that NAC exhibits direct chaperone activity toward diverse PolyQ substrates. Previous crosslinking data (Martin et al., 2018; Wiedmann et al., 1994) and our AtxQ78-NAC crosslinking-MS analysis indicate that NAC may interact with protein clients via both subunits. However, the specific substrate-binding site(s) of NAC critical for its chaperone function are unknown. To answer this, we took a mutational approach based on the evolutionary conserved regions of NAC including the NAC dimerization domains, the C-terminal UBA domain of αNAC, and the N-terminal ribosome-binding domain of βNAC harboring a conserved ribosome-binding motif (RRKxxKK) (FIG. 3A). We first asked which of these conserved domains may be crucial for preventing PolyQ aggregation in vivo. We generated three C. elegans strains overexpressing mutant NAC constructs under the control of the myo-3 promoter in the background of the PolyQ35::YFP strain. These included two deletion mutants lacking either the conserved αNAC UBA domain (ΔUBA-NAC) or the N-terminal βNAC domain (ΔNβ-NAC), as well as a mutation in the conserved ribosome-binding motif in the N-terminus of βNAC ($^{29}$RRK/AAA$^{31}$-NAC) (FIG. 3A), the latter of which abolished ribosome-binding of NAC in vivo (FIG. 9A). All the NAC mutants expressed in C. elegans were stable and the expression levels were comparable to that of the overexpressed wild-type NAC complex (see FLAG immunoblot in FIG. 3D, FIG. 9B). We assessed PolyQ35::YFP aggregation in these animals on day 3 of adulthood by fluorescence microscopy as well as SDD-AGE. We observed that both the ΔUBA-NAC and the RRK/AAA-NAC mutants suppressed PolyQ35::YFP aggregation similarly to WT-NAC indicated by the increased diffuse PolyQ35::YFP signal in the head region of these animals in comparison to control worms (ev) where the majority of the PolyQ35::YFP is aggregated in puncta (FIG. 3C). This correlated well with the levels of insoluble PolyQ35::YFP detected by SDD-AGE (FIG. 3D). Thus, neither the UBA domain nor ribosome-association of NAC is required to suppress PolyQ35::YFP aggregation. The latter finding suggests that NAC may serve additional chaperone functions off the ribosome in C. elegans. These data were intriguing because analysis of NAC distribution in yeast shows it is almost exclusively associated with ribosomes (Raue et al., 2007). However, polysome profiles of NAC distribution in both C. elegans and human cells showed a large fraction NAC was not associated with ribosomes (FIG. 3B and FIG. 10), suggesting that NAC may also exert a post-translational chaperone function in vivo. The finding of a large pool of non-ribosome associated NAC under steady state conditions in C. elegans and human cells (FIG. 3B and FIG. 10) together with the observed aggregation-suppression activity of a NAC variant that does not bind to ribosomes both support the idea of off-ribosomal chaperone functions for NAC in the cytosol.

Figure 3E:
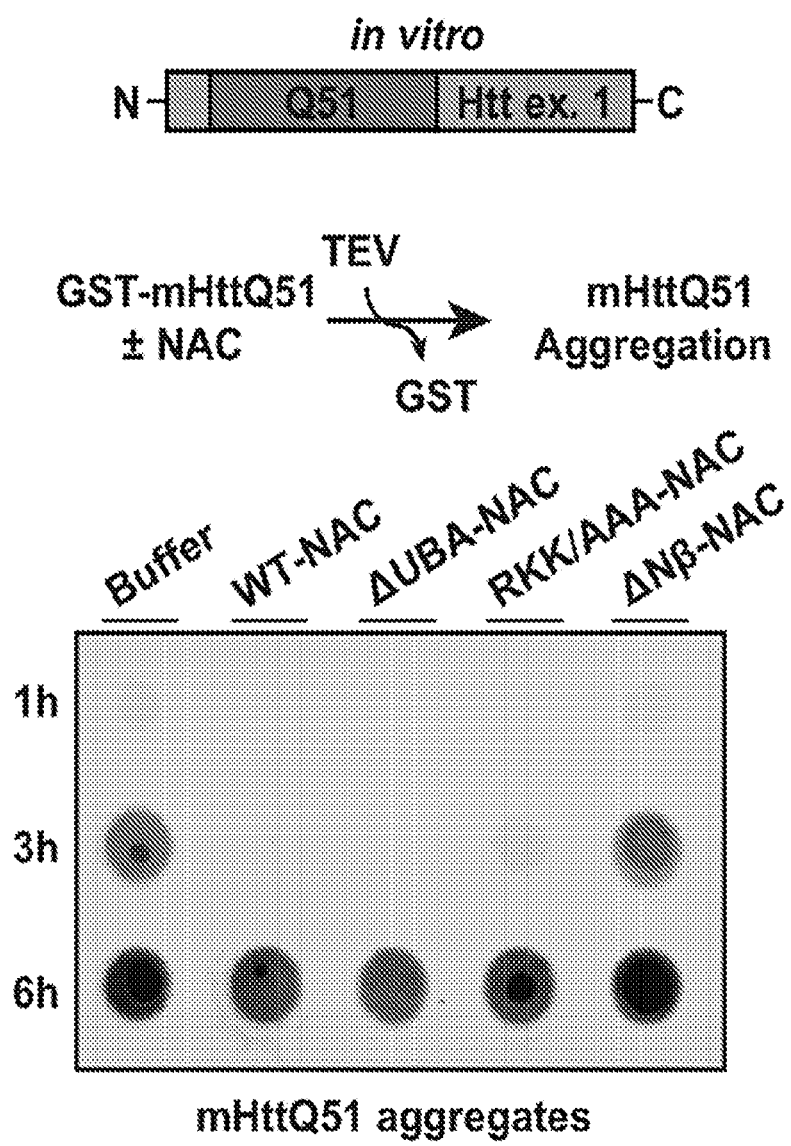

Strikingly, deletion of the N-terminal domain of βNAC abrogated the ability of NAC to suppress PolyQ35::YFP aggregation (FIGS. 3C, 3D and 9B), indicating that this region contains an essential interaction site for PolyQ tracts, which is consistent with our AtxQ78-NAC crosslinking-MS data (FIG. 2C). To directly address this possibility, we tested the ability of the different NAC mutants to suppress mHttQ51 aggregation in vitro, using purified components. Consistent with the in vivo results, addition of purified ΔUBA- or RRK/AAA-NAC delayed mHttQ51 aggregation similar to wild-type NAC, whereas ΔNβ-NAC lost the ability to suppress aggregation (FIG. 3E). In sum, the crosslinking data combined with the in vitro and in vivo PolyQ aggregation analyses strongly suggest that the N-terminal domain of @NAC contains a crucial PolyQ substrate-binding site. Importantly, our data also imply that NAC suppression of pathogenic PolyQ aggregation via this domain can occur in a ribosome-independent manner.

NAC Exerts Broad Spectrum Chaperone Activity

Figure 4A:
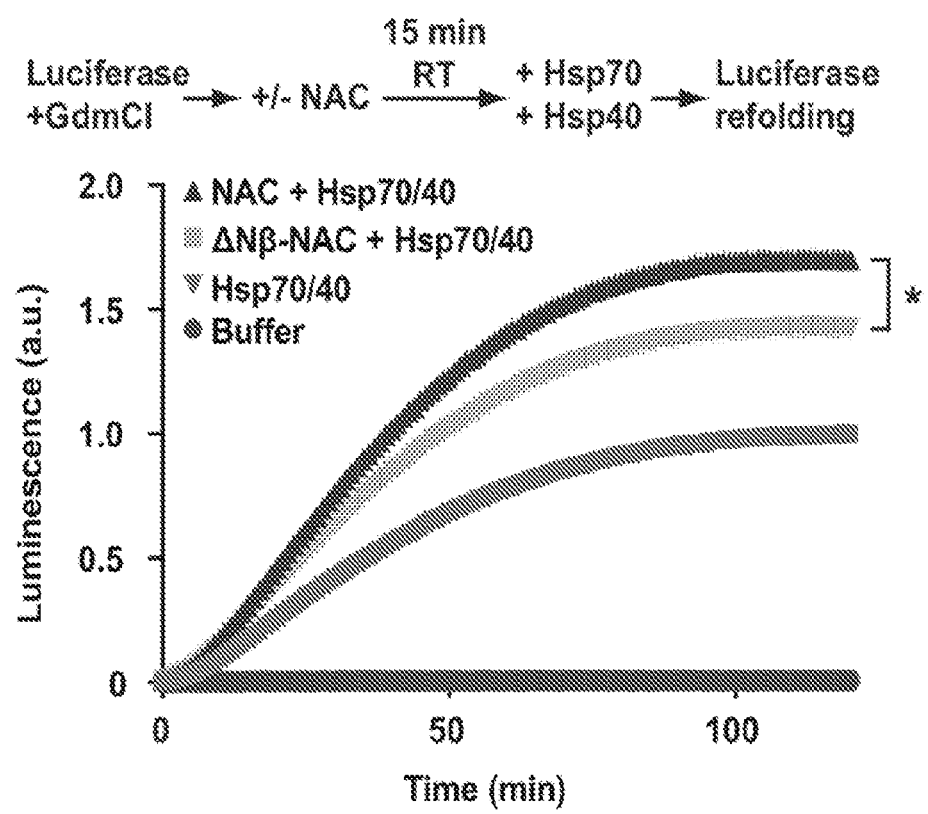
FIGS. 4A-4D show that NAC exerts broad spectrum chaperone activity.
Figure 11A:
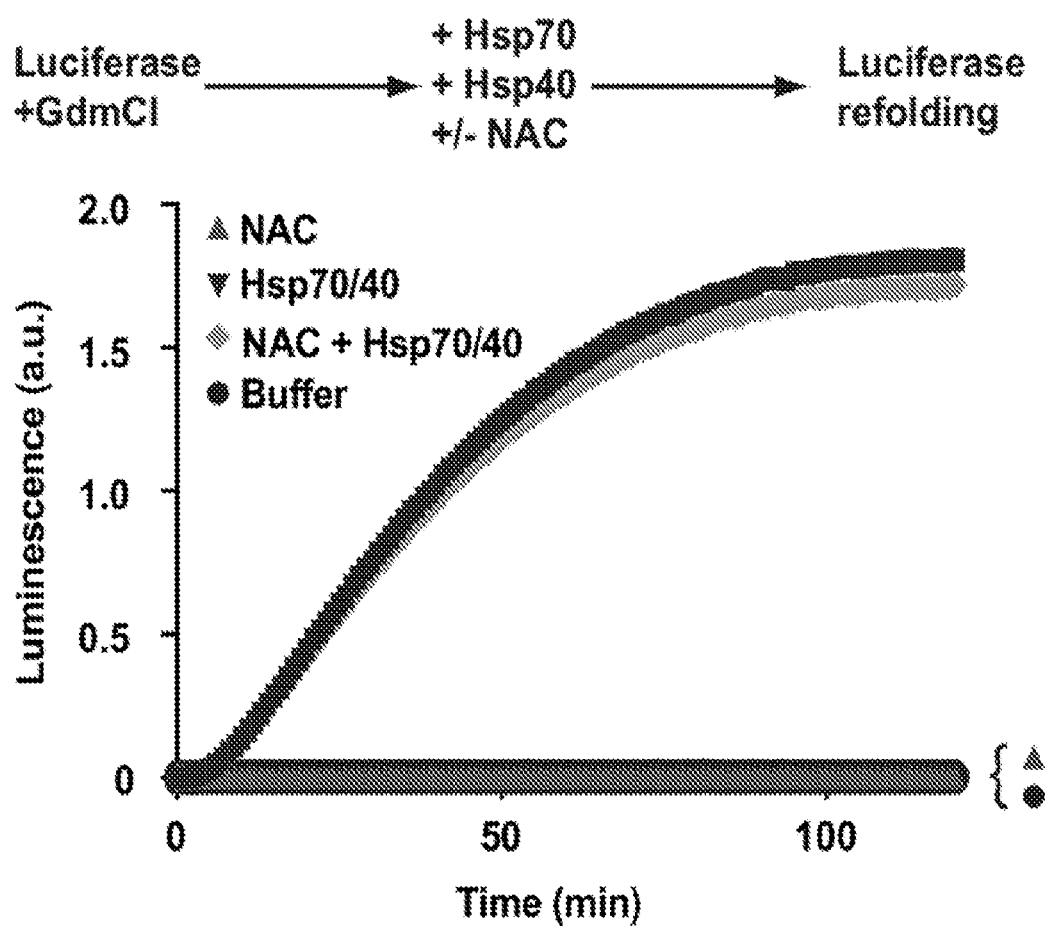
FIGS. 11A-11D show the chaperone activity of NAC on luciferase.
Figure 11B:
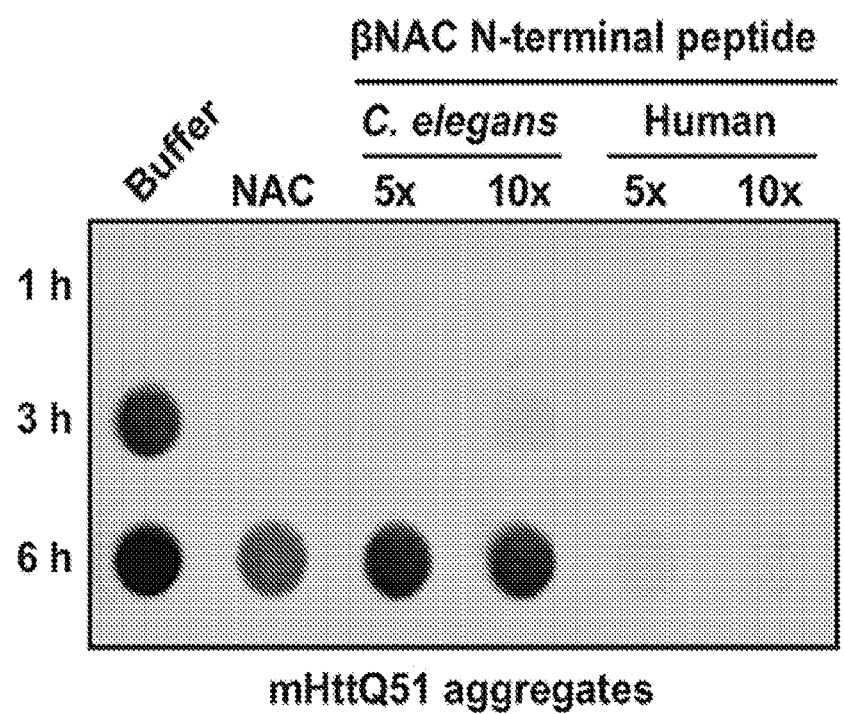
Figure 11C:
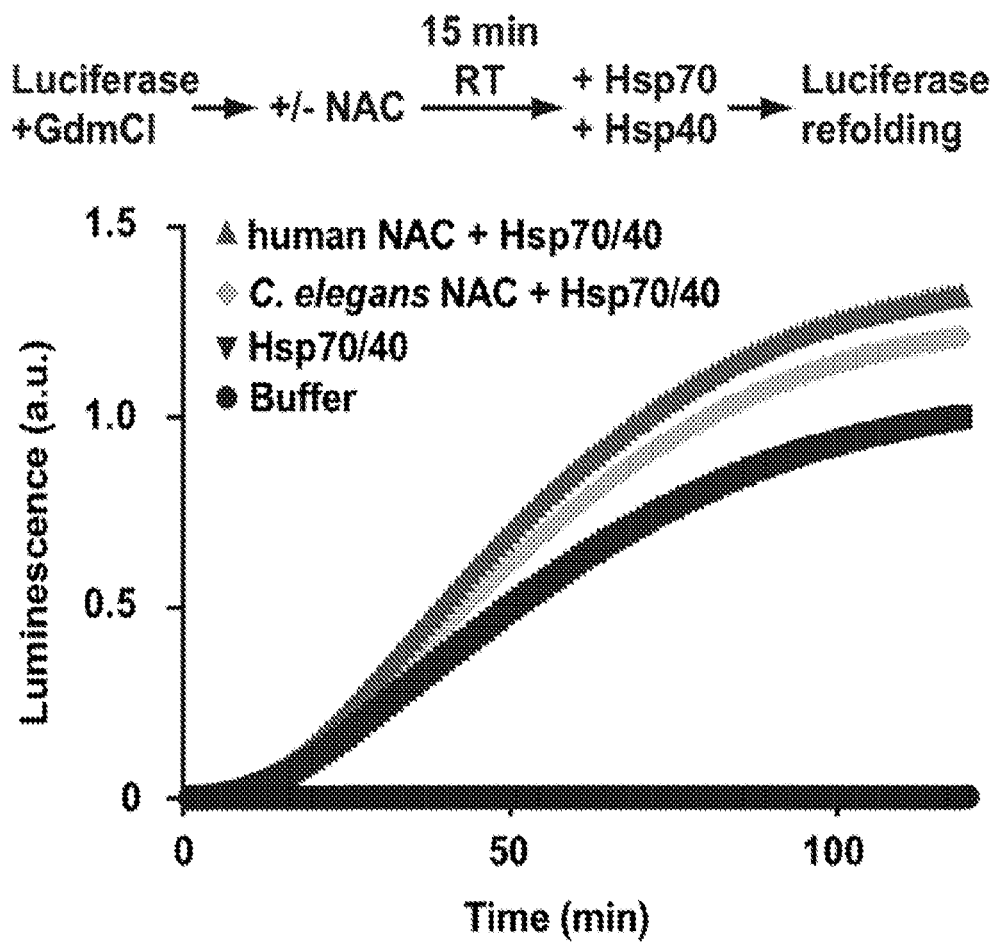

We next investigated whether the identified NAC aggregation suppression activity involving the N-terminal βNAC domain is PolyQ-specific or reflects a broad-spectrum chaperone activity. As a non-PolyQ model substrate, we used chemically denatured firefly luciferase that is known to rely on molecular chaperones to become refolded and luminesce (Schroder et al., 1993). Indeed, we found that luciferase activity after denaturation with guanidine-HCl (GdmCl) was restored after addition of an ATP-driven Hsp70/Hsp40 folding chaperone system (FIG. 11A, green curve). Interestingly, we found that purified human NAC alone had no effect on luciferase refolding (FIG. 11A, red curve) and did not enhance luciferase refolding upon addition to the Hsp70/Hsp40 system (FIG. 11A, grey curve). However, when NAC was added to chemically denatured luciferase first, subsequent refolding by the Hsp70/Hsp40 system was strongly enhanced over levels of just Hsp70/Hsp40 refolding (FIG. 4A, red versus green curve). A molar equivalent control protein of similar size, GFP, showed no enhancing effect (FIG. 11B, black curve). Similar results were obtained with C. elegans NAC (FIG. 11C, pink curve). That NAC was only effective in the initial stages of luciferase refolding was strikingly similar to the necessity of NAC to be involved in the earlier stages to suppress aggregation of mHttQ51 (FIG. 7C). Thus, NAC exerts a general holdase chaperone function and maintains unfolded luciferase or pathogenic aggregation substrates in a soluble and refolding competent state. Importantly, we found that the activity of ΔNβ-NAC was significantly reduced compared to wild-type NAC (FIG. 4A, yellow curve). Thus, the same domain crucial to prevent PolyQ aggregation is also necessary to hold luciferase in a refolding competent state. However, in contrast to the PolyQ substrates, ΔNβ-NAC still exerted residual chaperone activity toward denatured luciferase, suggesting that NAC contains additional unidentified chaperone domains that can bind luciferase, a protein with higher sequence complexity than PolyQ-expanded Htt or AtxQ78.

Figure 4B:
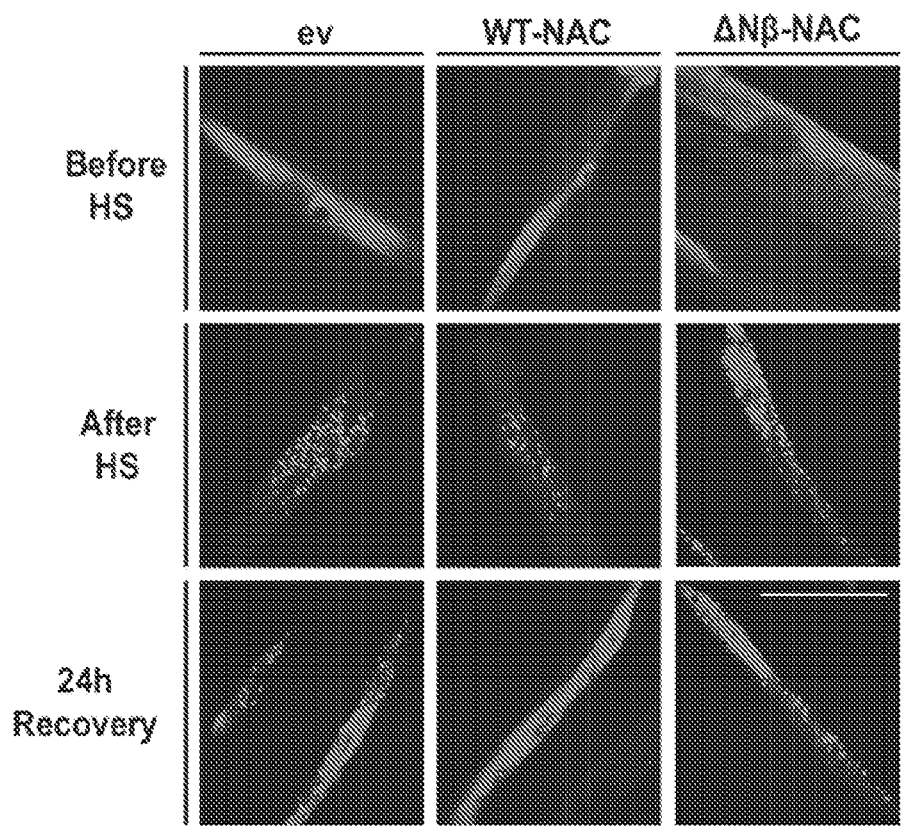
Figure 11D:
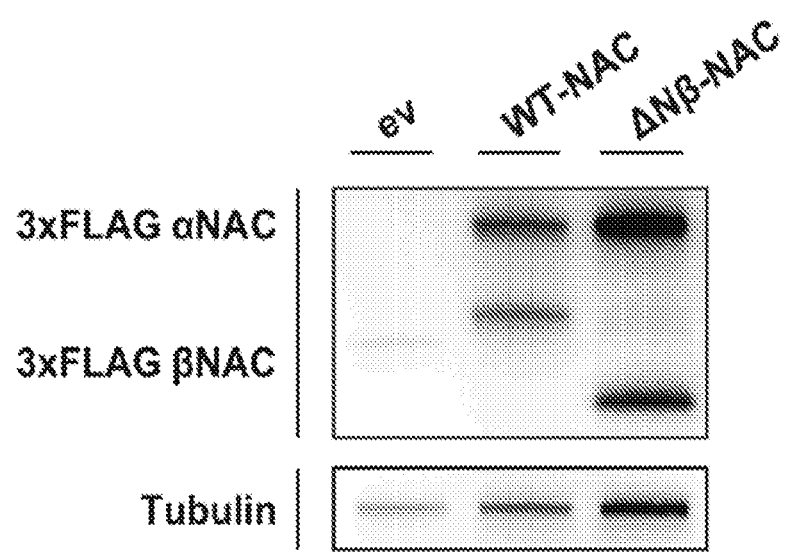

We further investigated NAC activity on luciferase refolding in vivo using a C. elegans strain expressing a structurally destabilized version of luciferase fused to EGFP (FlucDM-EGFP) in muscle cells (Gupta et al., 2011). This protein is soluble at moderate temperature but aggregates upon heat stress. After heat-shock (1 h, 33° C.) of worms, FlucDM-EGFP formed large punctate aggregates which were still evident in control animals after 24 h recovery at 20° C. (FIG. 4B, "ev"). Overexpression of wild-type NAC in these worms allowed FlucDM-EGFP aggregation to fully revert back to diffuse GFP signal within the 24 h recovery phase (FIG. 4B, "WT-NAC"), showing that NAC promotes in vivo refolding of luciferase, consistent with the in vitro findings (FIG. 4A). However, overexpression of ΔNβ-NAC was inefficient to revert heat-shock induced FlucDM-EGFP aggregates back to the diffuse, soluble form after the 24 h recovery period (FIG. 4B, "ΔNβ-NAC," and FIG. 11D). Thus, efficient luciferase refolding by NAC depends on N-βNAC, in vitro and in vivo. Overall, these data corroborate that the N-terminus of βNAC represents a central chaperone domain of NAC for luciferase as well as for PolyQ substrates.

Figure 4C:
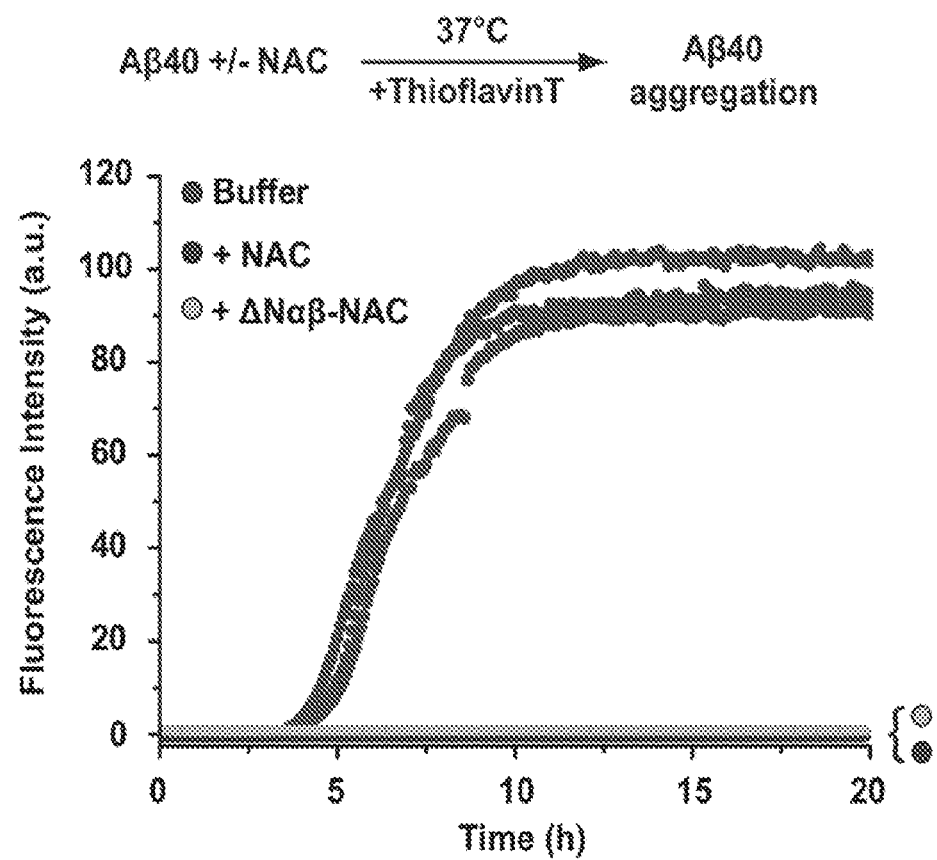
Figure 4D:
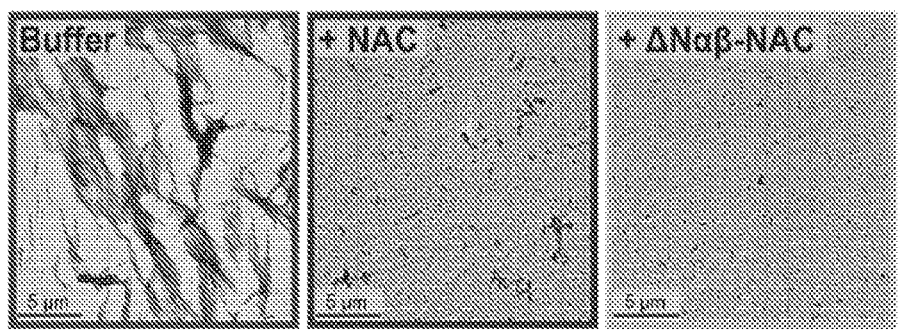
Figure 12A:
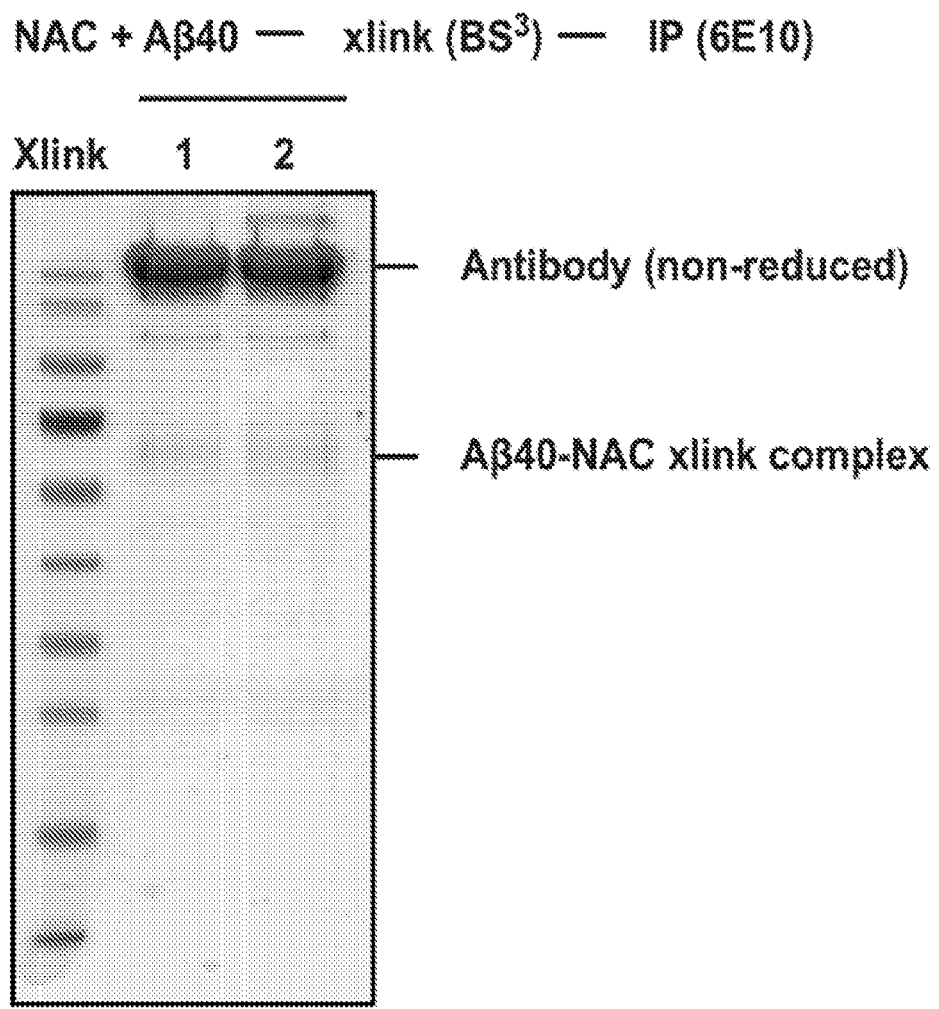
FIGS. 12A-12C show the chaperone activity of NAC on Aβ40.
Figure 12B:
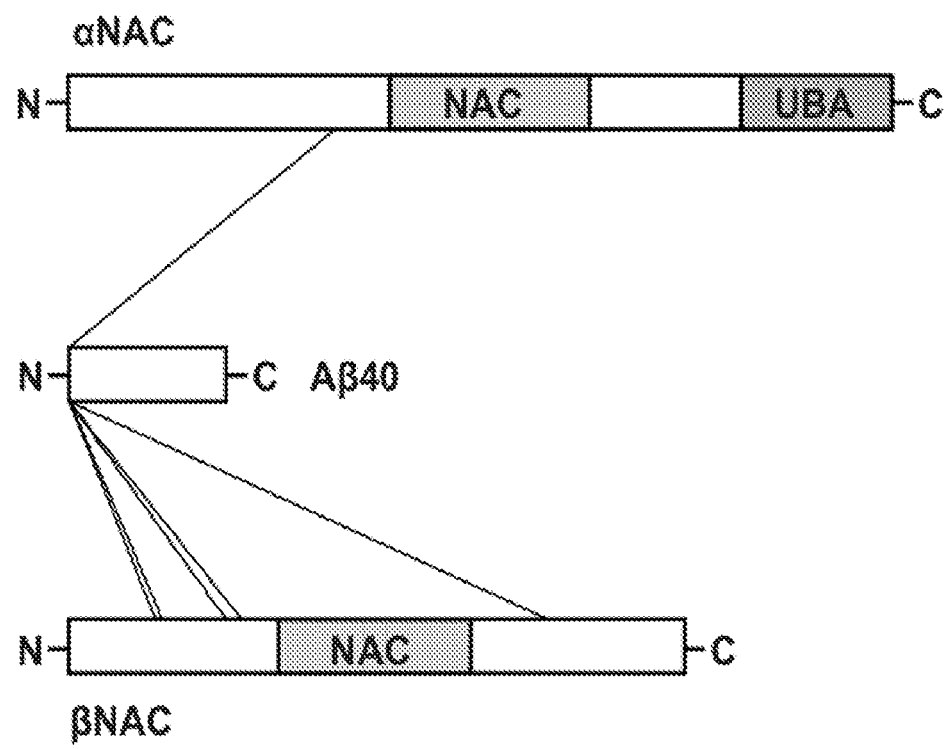
Figure 12C:
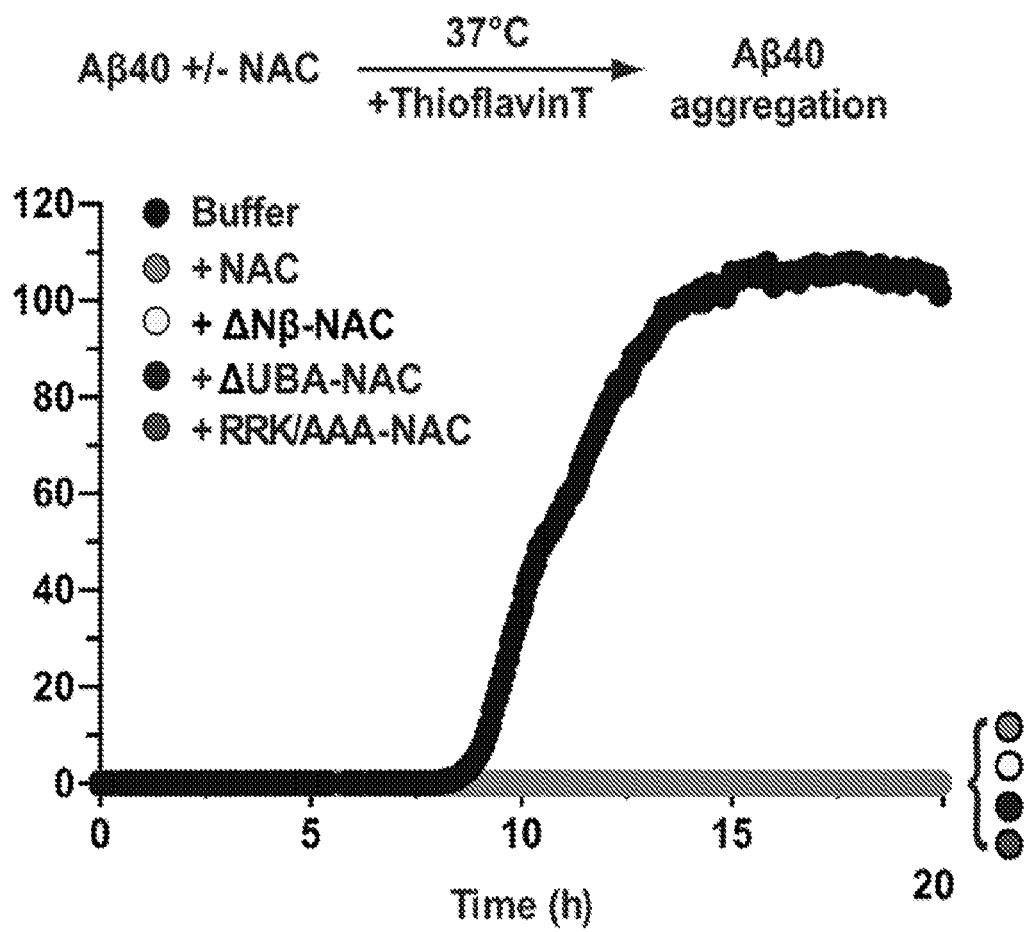

Next, we investigated whether NAC suppresses aggregation of the Alzheimer's disease related Aβ40 peptide, which mainly exhibits in contrast to PolyQ peptides a hydrophobic character. Aβ40 aggregation was recorded over time in vitro using Thioflavin T (ThT) fluorescence as a read out for amyloid fibril formation. In the absence of NAC, we observed a rapid increase of ThT fluorescence indicating Aβ40 aggregation (FIG. 4C, "Buffer"), and electron microscope analysis confirmed formation of aggregates with fibrillar structure (FIG. 4D). Remarkably, equimolar addition of purified human NAC completely suppressed Aβ40 aggregation and fibril formation (FIG. 4C, D). In addition, ΔUBA- and RRK/AAA-NAC mutants also fully suppressed Aβ40 aggregation (FIG. 12C). However, in contrast to the PolyQ substrates and luciferase, the N-terminal βNAC domain was dispensable for preventing aggregation of the highly hydrophobic Aβ40 substrate. Though crosslinking-MS analyses indicated an interaction of Aβ40 with the N-terminal domains of NAC similar to AtxQ78 (FIG. 12A, B), NAC mutants lacking the βNAC N-terminus (ΔNβ-NAC) or the N-termini of both subunits (ΔNαβ-NAC) were fully active in suppressing Aβ40 aggregation comparably to WT-NAC (FIG. 4C, D and FIG. 12C). Thus, NAC likely contains other important substrate interaction sites that may specifically bind hydrophobic segments in substrates such as Aβ40 and luciferase.

In sum these data show that NAC is able to chaperone diverse substrates with different structural and physicochemical properties corroborating a general chaperone function of NAC. Moreover, our data reveal that the N-terminal βNAC domain confers substrate-specific chaperone function.

Functional Characterization of the N-Terminal βNAC Chaperone Domain

Figure 5B:
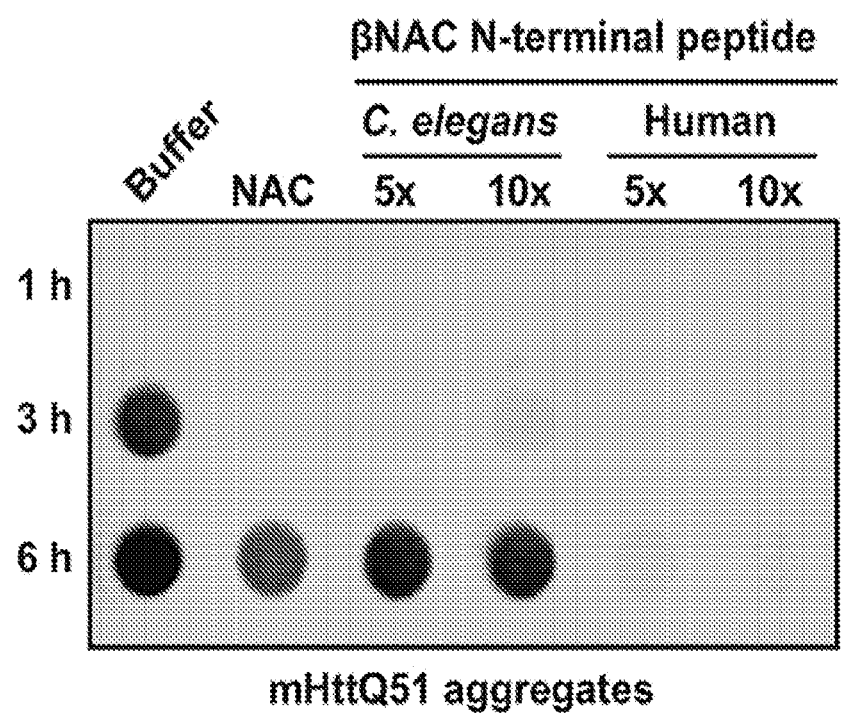
Figure 13A:
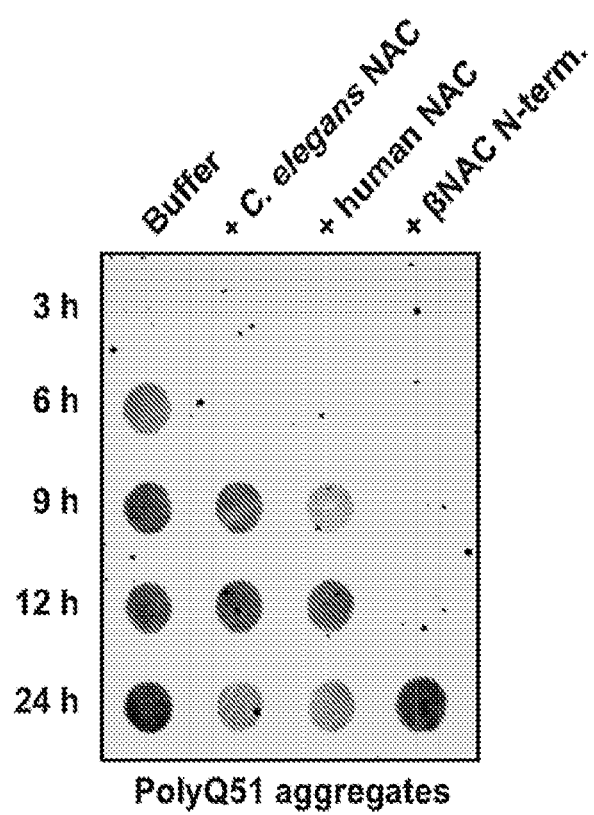
Figure 13C:
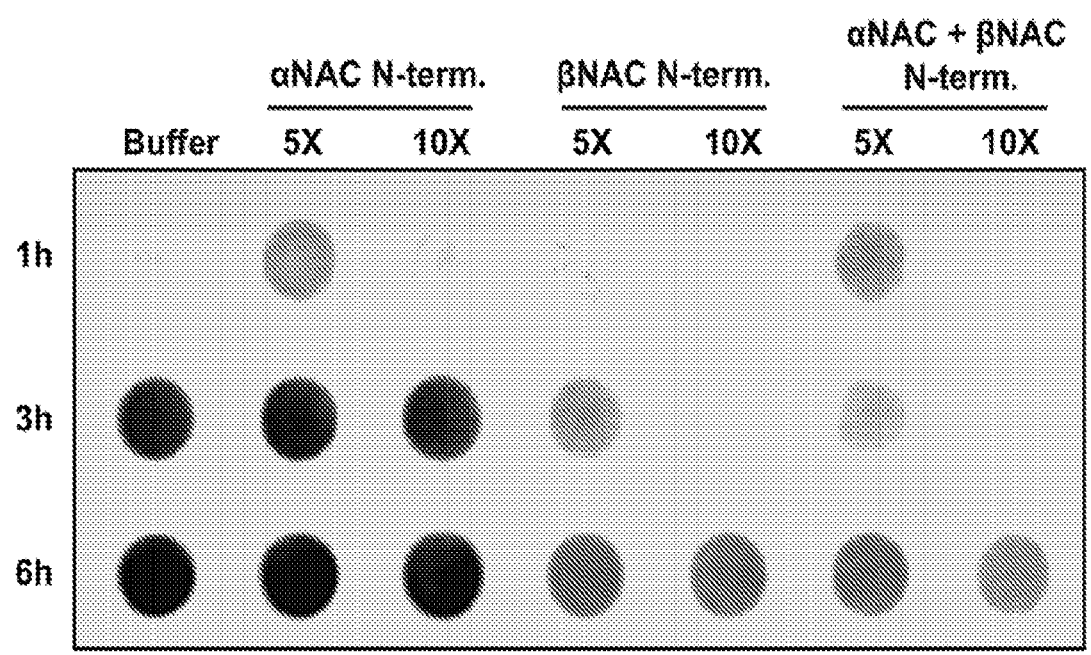

Our data show that the N-terminal domain of βNAC not only confers ribosome-binding but also has chaperone activity, preventing the aggregation of PolyQ proteins and promoting refolding of firefly luciferase. This small domain (~40 aa) is characterized by a high positive net charge in particular at its C-terminal half, which is predicted to be unstructured (FIG. 5A). To gain more insight into the chaperone activity of this domain we utilized synthetic peptides corresponding to the N-terminal region of βNAC from both human and C. elegans in in vitro aggregation assays. We observed that these N-βNAC peptides alone were sufficient to suppress aggregation of mHttQ51 (FIG. 5B). Similar aggregation suppression results were obtained when using the pure PolyQ51 substrate (FIG. 13A), indicating a direct interaction of the N-βNAC peptides with the polyglutamine stretch.

Figure 5C:
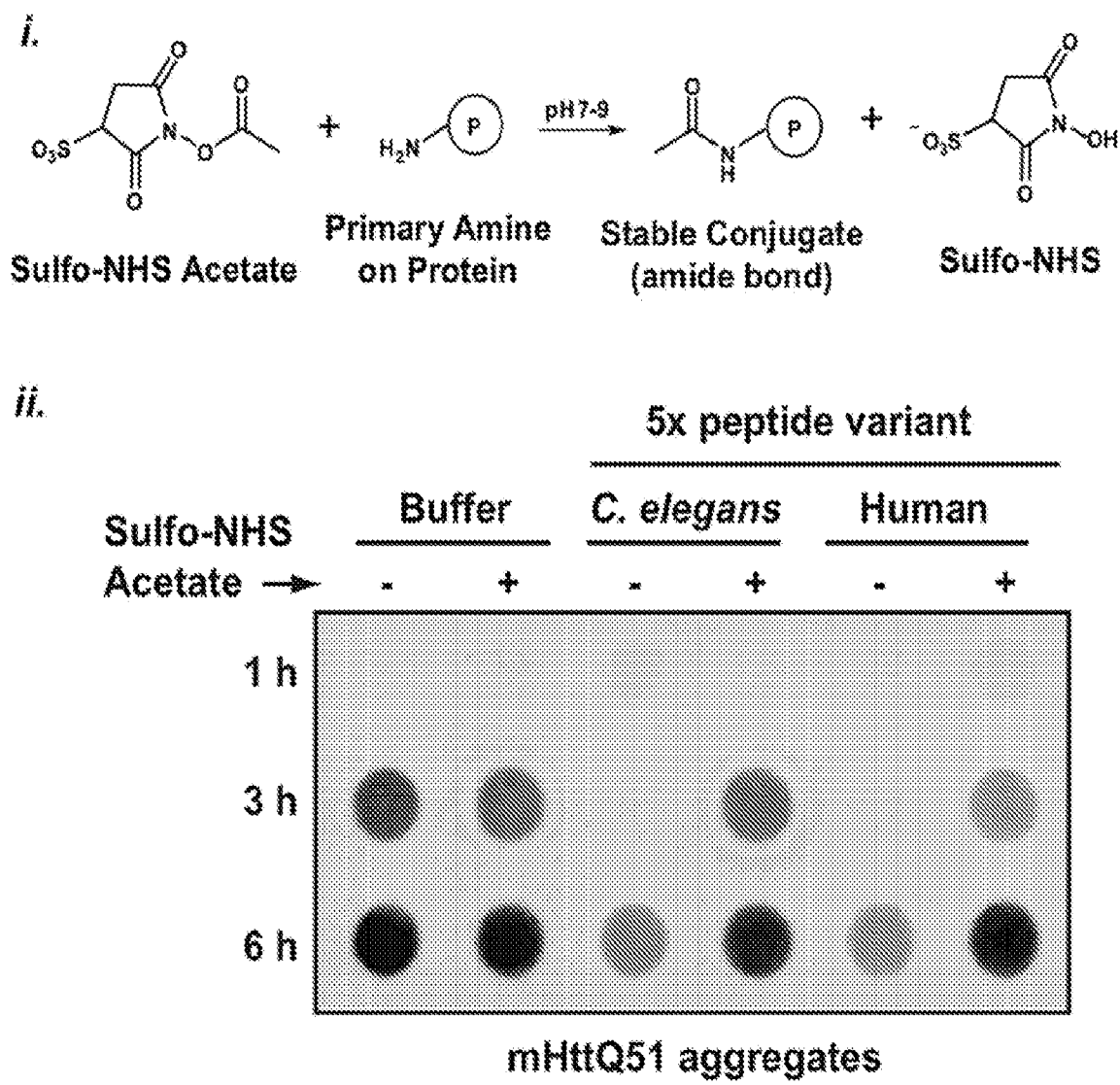
Figure 5D:
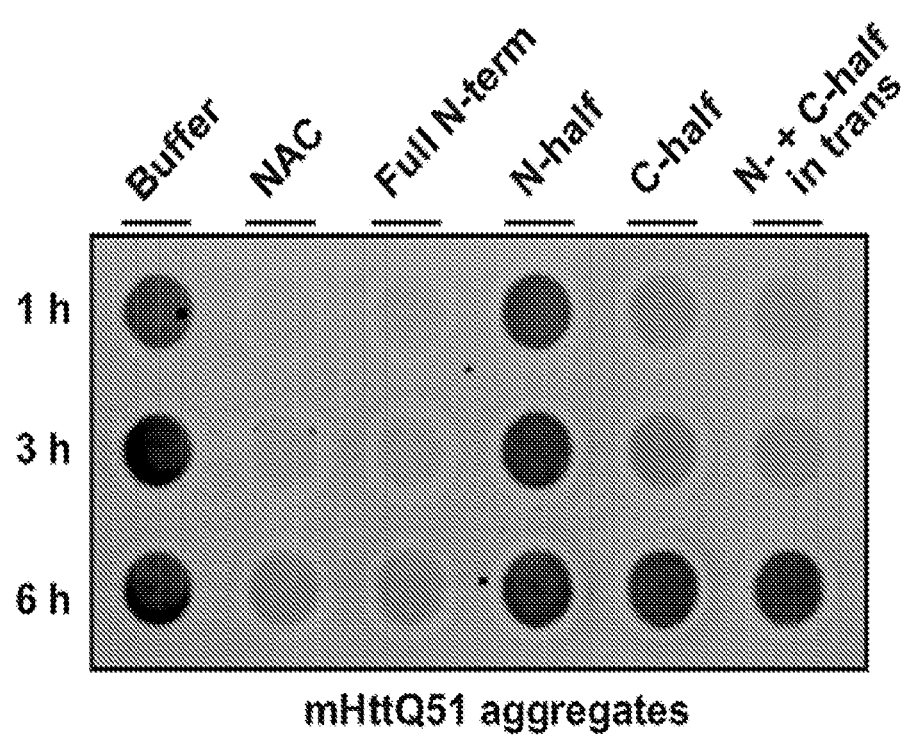

The most obvious characteristic of the N-βNAC peptides is the high positive net charge (FIG. 5A). In addition to hydrophobic contacts, electrostatic interactions mediated via highly charged regions in chaperones are emerging to play an important role in client binding (He et al., 2016; Horowitz et al., 2016; Joachimiak et al., 2014). We thus asked whether the positively charged residues contribute to the ability of these peptides to suppress PolyQ aggregation. To address this, we acylated primary amines in lysine residues of the peptides using Sulfo-NHS-acetate in order to neutralize the positive charge (FIG. 5Ci and FIG. 13B). Interestingly, we observed that upon labeling the lysine residues, the peptides significantly lost their ability to suppress mHttQ51 aggregation (FIG. 5Cii). Thus, the positively charged residues in the N-terminal βNAC domain are critical for its chaperone activity. To investigate this in more detail, we split the human peptide into two halves resulting in an N-terminal peptide containing a predicted conserved helical element with several hydrophobic residues and a C-terminal peptide encompassing most of the conserved positively charged residues (FIG. 5D). Remarkably, the C-terminal half of N-βNAC was alone able to suppress mHttQ51 aggregation, whereas the N-terminal half showed no effect (FIG. 5D). This finding corroborates that the primary PolyQ binding site is located in the positively charged stretch of the peptide. Although very potent, the C-terminal peptide was not as completely effective as the full-length peptide or the full-length NAC chaperone in suppressing mHttQ51 aggregation (FIG. 5D). This suggests that additional regions in the N-βNAC peptide contribute to the chaperone activity. Of note, mixing the N-half peptide and the C-half peptides did not increase the aggregation suppression ability over the C-half peptide alone (FIG. 5D). Thus, full function is only obtained by a cooperative activity that relies on the entire N-βNAC.

We also investigated the activity of the N-terminus of the αNAC subunit, which is also highly charged, albeit with a net negative charge (FIG. 5A). This domain is thought to be flexible, similar to the βNAC N-terminal region, and our AtxQ78-NAC crosslinking data indicated an interaction with the mutant PolyQ domain (FIG. 2C). However, we found that N-αNAC peptides either added alone or in combination with the N-βNAC peptides had no effect on mHttQ51 aggregation (FIG. 5E and S7C), even at 10× molar excess over the mHttQ51 substrate, underscoring the specificity of the aggregation suppression effect by the positively charged βNAC N-terminal domain.

NAC Suppresses Toxicity of PolyQ Proteins in Neuronal Cell Lines and Animals

Figure 6A:
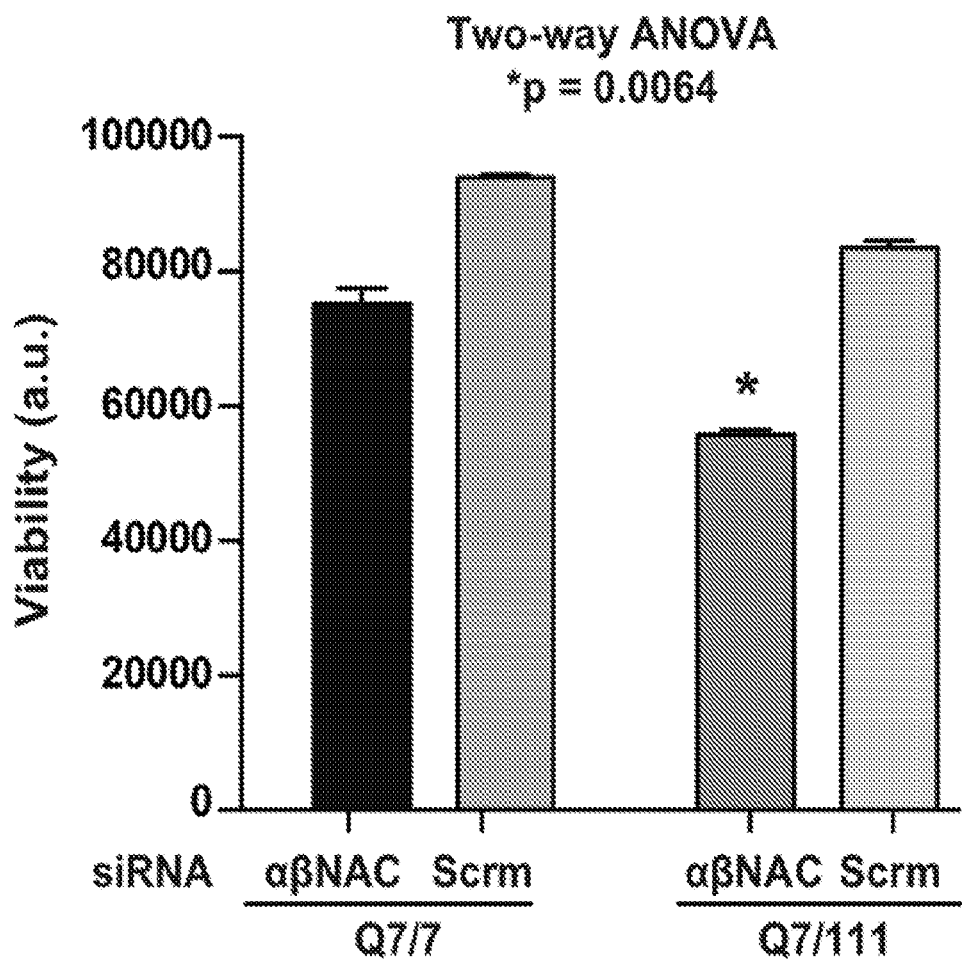
Figure 6B:
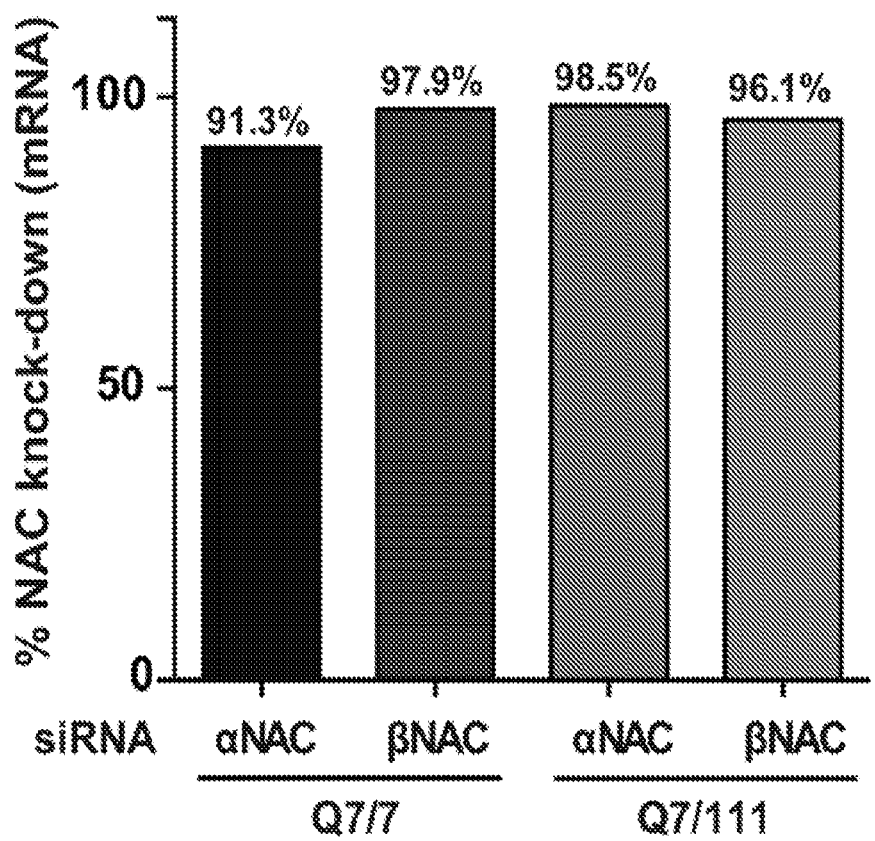
Figure 14:
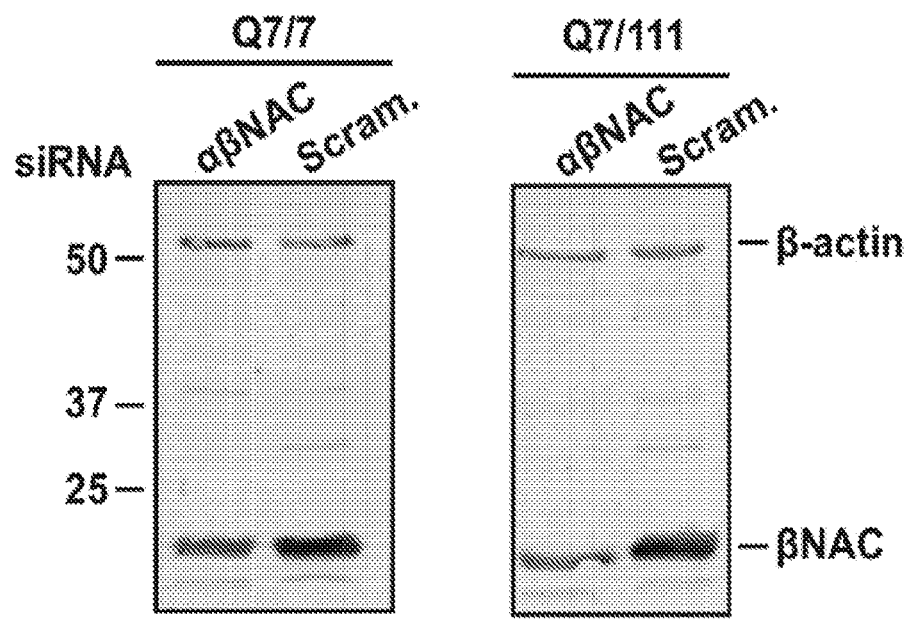
FIG. 14 shows the knockdown efficiency of NAC in Q7/7 and Q7/111 cell lines. Western blot showing βNAC knockdown in siRNA-treated cell lines used in viability assay shown in FIG. 6A. β-actin was probed simultaneously as a loading control.
Figure 15A:
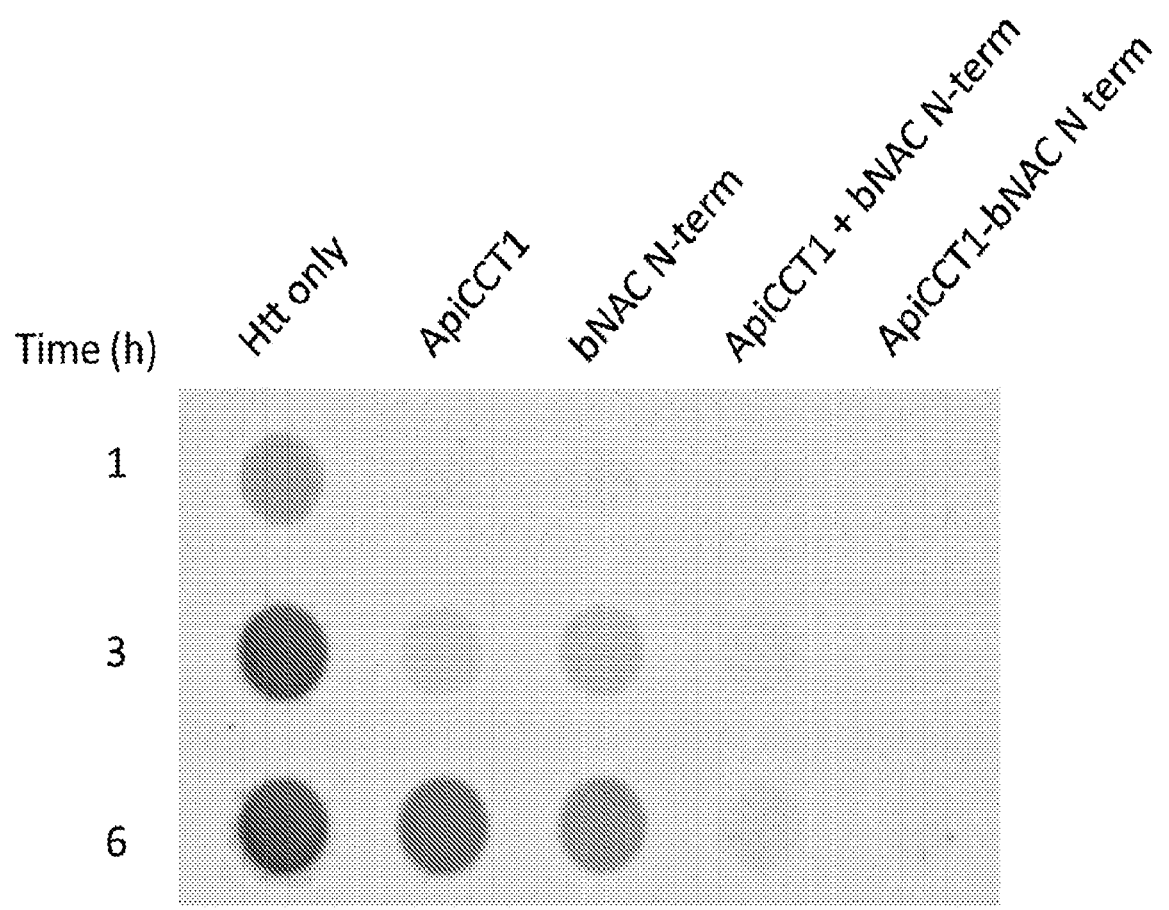
FIGS. 15A and 15B show that the combination of both ApiCCT1 and bNAC N-terminal domain suppress Htt aggregation better than individual components.
Figure 15B:
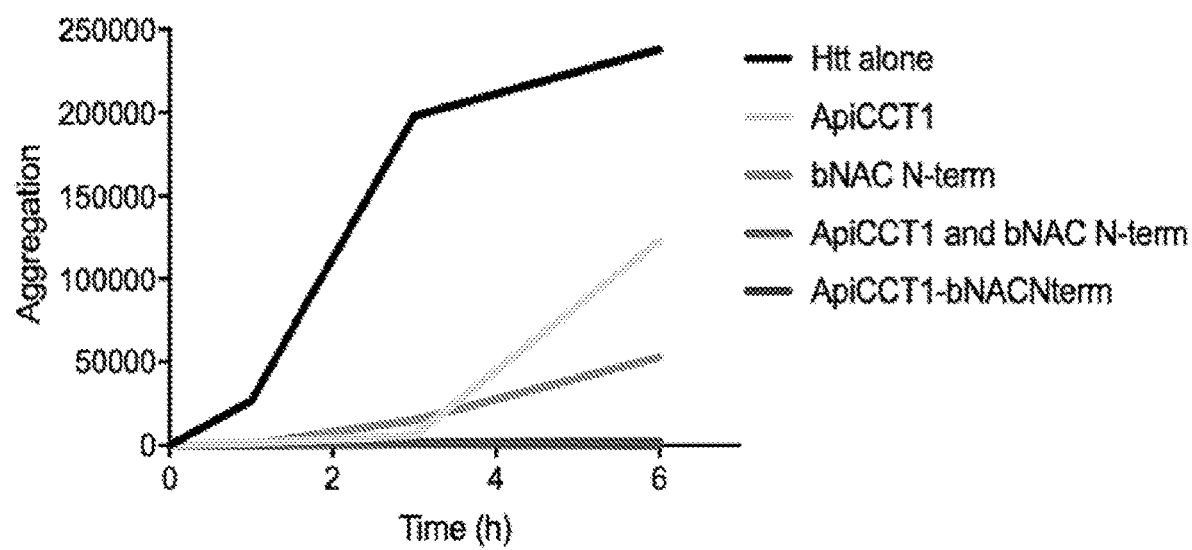
Figure 16A:
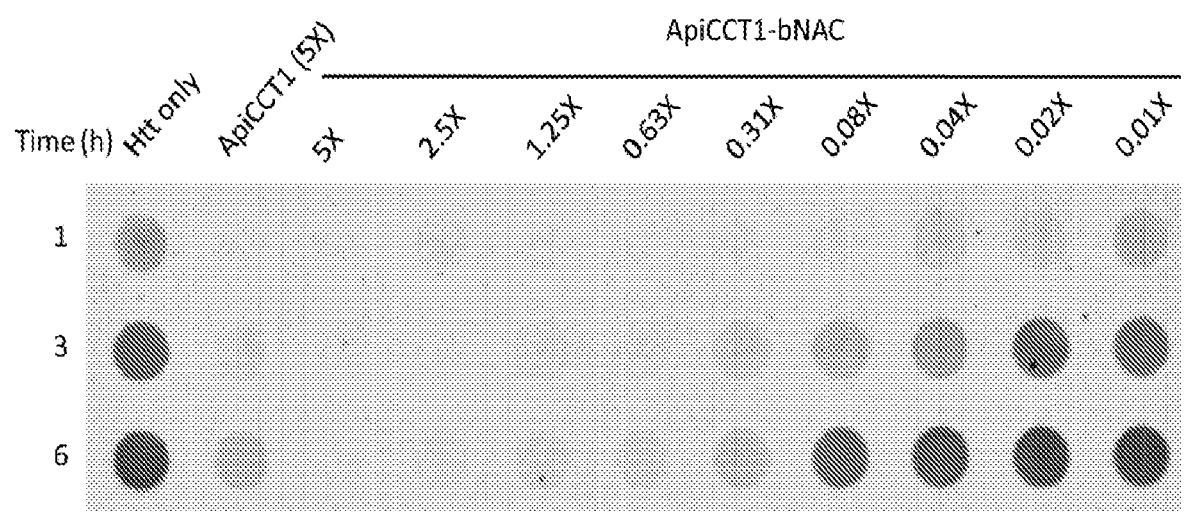
FIGS. 16A and 16B show that ApiCCT1-bNAC can suppress HttQ51 aggregation at sub-molar concentrations.
Figure 16B:
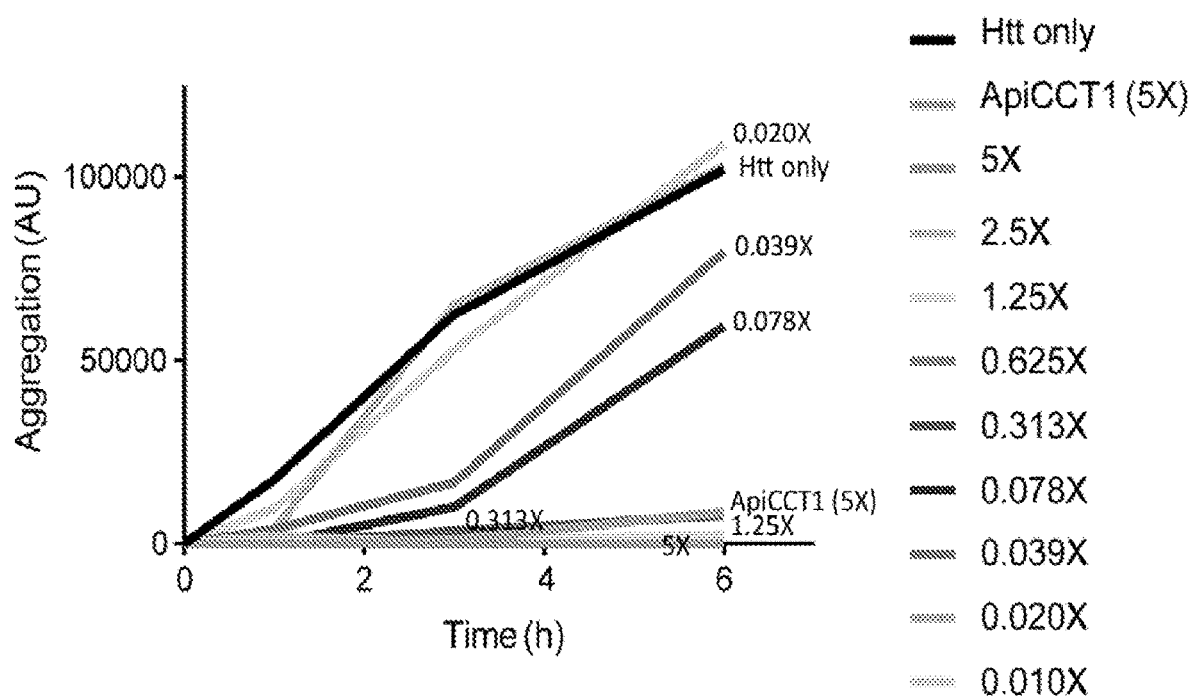
Figure 17A:
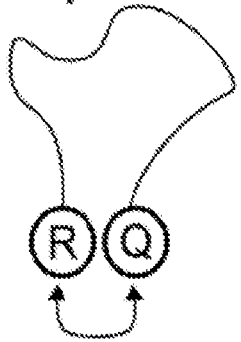
FIGS. 17A-17B show a fluorescence quenching assay as a reporter for early events in Htt aggregation. The schematic (FIG. 17A) shows loss of fluorescence in BodipyTMR-labelled HttQ44 upon oligomerization and aggregate formation (FIG. 17B). Previous work showed this quenching event reports on an early association event between Htt monomers.
Figure 17A:
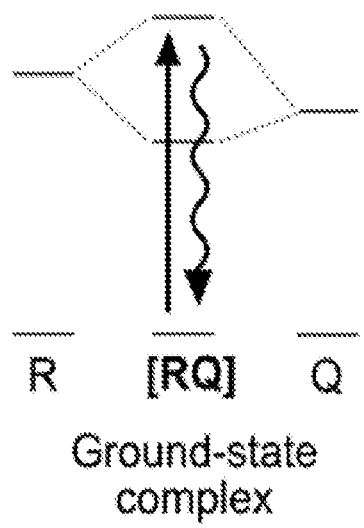
Figure 17B:
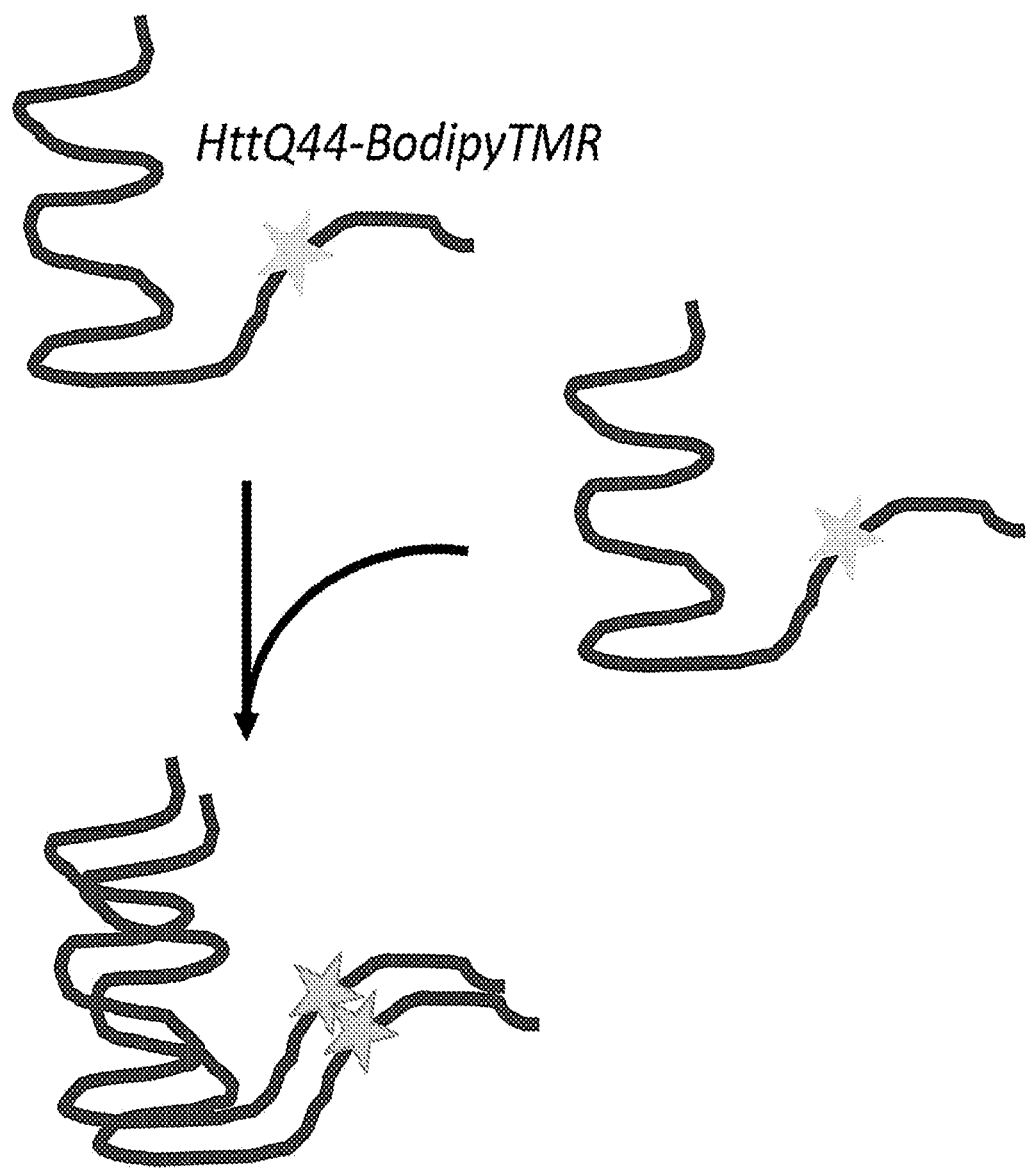
Figure 18:
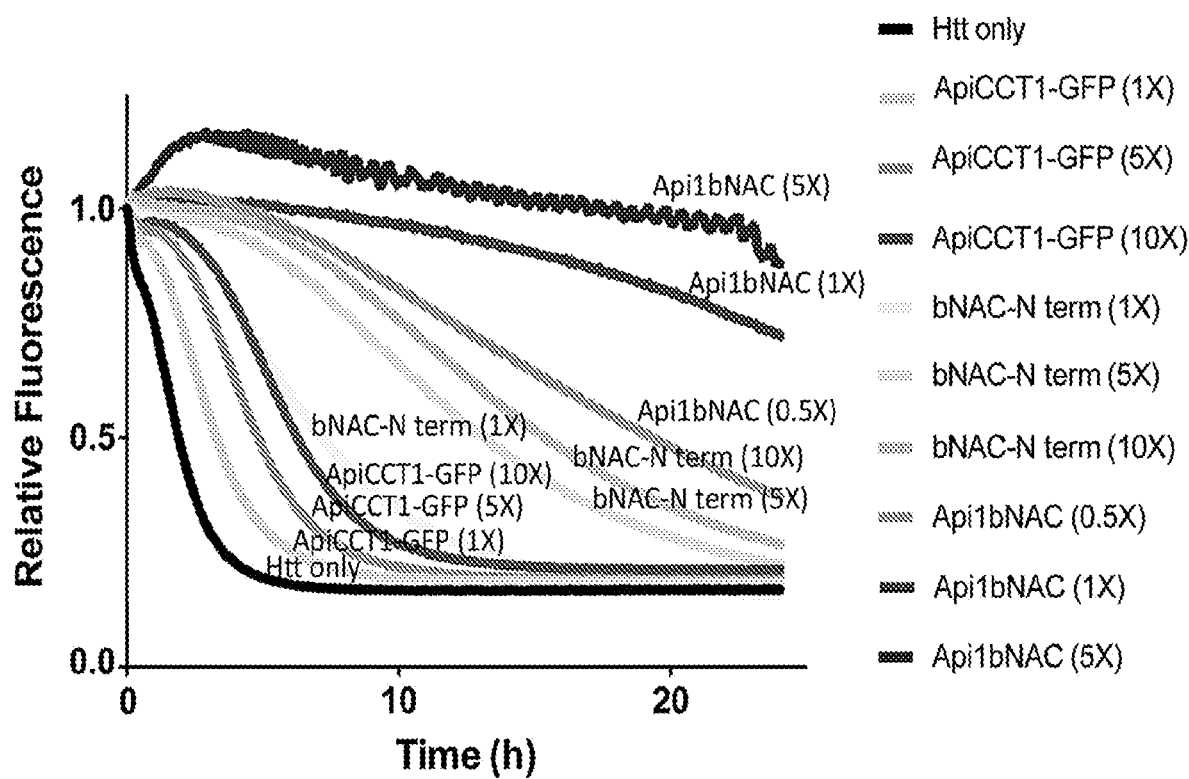
FIG. 18 shows that ApiCCT1-bNAC is better and more stably suppresses Htt aggregation overtime compared to the ApiCCT1 and bNAC N-terminal domain individually. A fluorescence quenching assay was used to monitor aggregation of HttQ44-BodipyTMR with titrations of various chaperones over a 24-hour time period.

Next, we investigated the relevance of NAC to mutant Huntingtin toxicity in neuronal cells. Here, we used a knock-in mouse striatal cell line heterozygous for a 111 glutamine residue repeat mutation in the full-length Huntingtin protein (HttQ7/111), which is a well-established cell line to model Huntington's disease pathology (Trettel et al., 2000). We compared the phenotype of this mutant Huntingtin cell line with that of a striatal mouse cell line homozygous for the wild-type Huntingtin allele (HttQ7/7). We first assessed how knockdown of NAC would affect viability of mHtt-expressing cells. We depleted both NAC subunits by siRNA, and after 72 hours measured the viability of these cells by measuring ATP levels using the Cell Titer Glo assay. While knockdown of NAC decreased viability of both cell lines, the mHtt-expressing HttQ7/111 cells were significantly more sensitive toward NAC depletion (FIG. 6A). Knock-down efficiency of αNAC and βNAC was comparable in two Htt cell lines (FIG. 6B and FIG. 14). Thus, while NAC generally promotes striatal neuron health, NAC is especially critical to maintain viability of neurons expressing mutant, aggregation-prone Huntingtin. To address whether ribosome-binding of NAC was necessary for this protective function, we tried to overexpress different NAC variants in striatal cells. However, this was not possible, so it remains unclear whether suppression of Htt toxicity in neurons by NAC results from its co- or post-translational function.

To understand the specific need for NAC in maintaining viability of mHtt-expressing striatal neurons, we asked whether NAC was especially crucial for neuronal protein homeostasis in the presence of mutant Huntingtin. Therefore, we analyzed the protein aggregation burden in both wild-type (HttQ7/7) and mutant Htt-expressing cells (HttQ7/111) upon silencing of NAC. Protein aggregation was assessed using the Proteostat dye, which recognizes aggregates from a broad range of protein substrates (Shen et al., 2011). We observed that in wild-type cells, knockdown of NAC had a negligible effect on protein aggregation, whereas protein aggregates strongly accumulated in the mHtt-expressing cells (FIG. 6C). Thus, NAC is essential to counteract the increased burden on the protein homeostasis machinery provoked by mHtt expression, demonstrating the essential, physiologically protective role NAC plays in maintaining protein homeostasis.

Figure 6D:
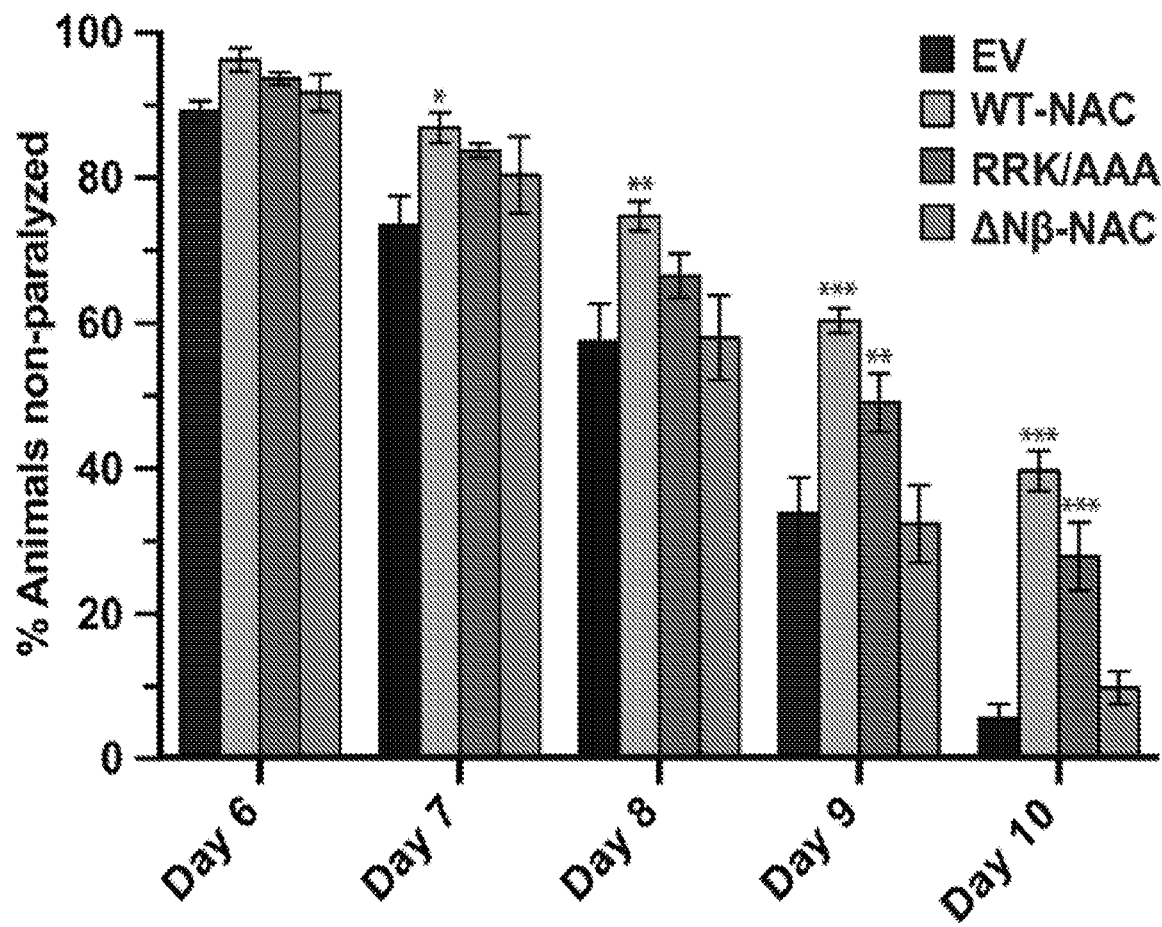

Finally, because protein aggregation has been tightly linked to age-associated organismal degeneration (Sala et al., 2017), we asked whether NAC is also essential for organismal fitness and healthy aging. We overexpressed wild-type NAC and mutant ΔNβ-NAC in *C. elegans* expressing the aggregation-prone PolyQ35::YFP and measured age-associated paralysis (Cohen et al., 2006; Morley et al., 2002). We found that overexpressing wild-type NAC significantly improves motility of PolyQ35::YFP-expressing worms during aging (FIG. 6D), suggesting that overexpression of NAC alone can improve protein homeostasis and organismal health. In addition, we found that this improvement in motility strictly depends on the presence of the N-terminus of βNAC (FIG. 6D), highlighting the importance of this domain in maintaining protein homeostasis in aging. Importantly, the protective activity of N-βNAC is mostly independent from its ribosome binding role as overexpression of the ribosome-binding deficient RRK/AAA-NAC variant still improved motility during aging albeit less effective than WT-NAC (FIG. 6D). Thus, ribosome-binding of NAC contributes but is not essential under these conditions per se for improving protein homeostasis and organismal health in aging. Overall these data show the tight linkage between cellular and organismal proteostatic health and the chaperone role of NAC as mediated by the N-terminus of the βNAC subunit.

Discussion

In this work, we establish that NAC has broad chaperone specificity which can occur also independent of its association with ribosomes. We demonstrate a novel chaperone role for NAC for a diverse set of substrates, including model chaperone substrates like misfolded luciferase and aggregation-prone proteins involved in neurodegenerative disorders, such as Huntington's disease, Spinocerebellar ataxia-3, and Alzheimer's disease. We mapped the binding interaction between NAC and mutant aggregation-prone PolyQ constructs to the N-terminus of the βNAC subunit. The N-terminal domain of the βNAC subunit was necessary and sufficient to suppress mutant PolyQ aggregation and enhances Hsp70/Hsp40-aided folding of luciferase. Interestingly, this domain was dispensable for suppression of Aβ40 aggregation, suggesting that there may be other chaperone-like domains of NAC that we have yet to discover, which are required for substrates with properties different from those of PolyQ. Moreover, we demonstrate that NAC chaperone activity is central in protection against proteostatic insults that occur in aging and age-related aggregation-prone disorders like Huntington's disease in primary neuronal cells and in *C. elegans*. We further show in *C. elegans* that the N-terminal βNAC subunit domain is crucial for this protective function. Overall, our data suggest a novel, physiological role for NAC as an essential chaperone in maintaining protein homeostasis in aging and age-related diseases.

Our data show that the same domain of NAC critical for ribosome-binding also exerts chaperone activity. Thus, the N-βNAC domain has a dual role and may serve chaperone functions on and off the ribosome. NAC may contact nascent substrates via N-βNAC to promote co-translational folding and likewise this domain binds misfolded cytosolic proteins post-translationally to prevent aggregation. Indeed, we found that in *C. elegans* as well as in human cells NAC exists in an equilibrium between a ribosome-bound and unbound state under steady state conditions with a large non-ribosomal fraction. Our data also clearly show that the chaperone function of NAC is not restricted to co-translational de novo protein synthesis as revealed by the ribosome-independent aggregation suppression effect of NAC on PolyQ proteins in vivo and in vitro. We suggest a model in which the canonical activity of NAC in co-translational protein transport and folding (del Alamo et al., 2011; Gamerdinger et al., 2015) is complemented by its off-ribosomal chaperone activity to prevent aggregation of misfolded cytosolic protein species. Whether ribosome-associated NAC also actively dissociates from the ribosome during protein stress to chaperone aggregation-prone substrates is an attractive hypothesis and remains to be further explored. Previous data had suggested an elegant mechanism for how NAC binding to misfolded protein species might be coupled to ribosome detachment under high proteotoxic stress (Kirstein-Miles et al., 2013). This stress-induced ribosome dissociation of NAC could be mediated by other chaperone co-factors activated by the presence of protein aggregation or by bulk association upon accumulation of protein aggregates.

Here, we show that NAC has the ability to remodel protein aggregation pathways through direct interaction with aggregation-prone substrates and this activity of NAC has an important role in vivo in protecting cells from proteotoxic stress. NAC knockdown in neuronal cells in the presence of pathogenic mutant Htt significantly compromises both cellular health and protein homeostasis to a similar extent as proteasome inhibition by MG132 (FIG. 6C). Without NAC to up-hold the delicate proteostatic balance, striatal cells succumb to extensive protein aggregation and complete loss of protein homeostasis, eventually leading to cellular toxicity. Thus, NAC plays a central role in sensing and maintaining the balance of protein homeostasis in mutant Htt-expressing cells. Interestingly, levels of βNAC were found to be strongly up-regulated in induced pluripotent stem cells (iPSC) derived from Huntington's disease patients, pointing to an adaptive protective cellular response (Chae et al., 2012). In addition to mutant Htt, NAC also suppresses aggregation of other amyloidogenic proteins related to diseases such as Parkinson's (α-synuclein; Martin et al., 2018) and Alzheimer's (Aβ40, this study), which suggests that NAC may play a central, protective role generally in aging and age-related diseases. In this respect, it is interesting to note that αNAC levels were found to be significantly down-regulated in brains of patients with Alzheimer's disease and Down syndrome with Alzheimer-like neuropathology (Kim et al., 2002).

Figure 7D:
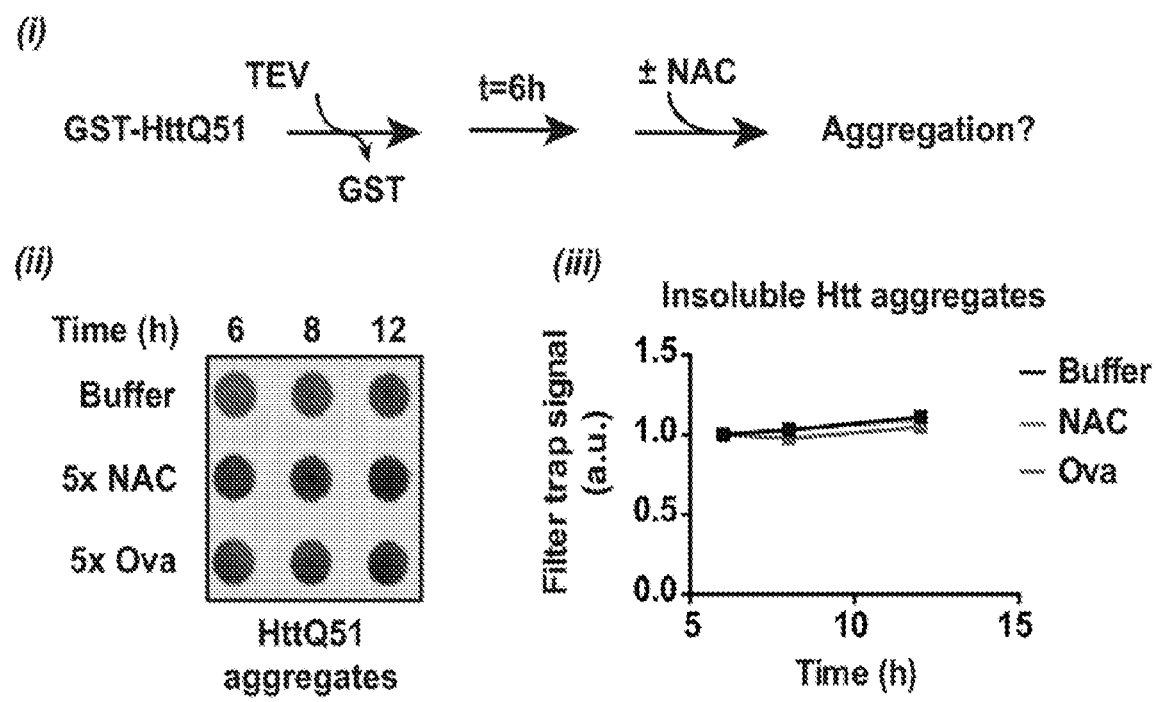

Our study shows that in metazoan cells, NAC is present in ribosome-bound and free pools, and has chaperone activity towards distinct types of substrates, including polyQ, Aβ40 and luciferase. It is likely that the chaperone functions described here also reflect NAC chaperone function at the ribosome to suppress aggregation or misfolding of nascent polypeptides. The type of misfolded or unfolded domain that NAC recognizes remains unclear. Interestingly, we find that NAC is most effective in the early stages of misfolding for aggregation-prone pathogenic proteins (FIG. 7D). This suggests that NAC may act as a holdase chaperone that recognizes a misfolded intermediate appearing early in the aggregation reaction. NAC may then prepare these early aggregation species substrates for further manipulation by other chaperones as demonstrated for luciferase in this study (FIG. 4A) or sequester aggregation-prone domains critical in the early stages of oligomerization. It is tempting to envision a similar activity for NAC when acting on nascent polypeptides. The affinity of NAC for different misfolded protein domains remains to be determined, and affinity may well depend both on the sequence and conformational properties of the client, as is observed for other ATP-independent chaperones (Saio et al., 2014; Stull et al., 2016). Our in vitro experiments demonstrate a concentration dependence of NAC suppression of PolyQ aggregation (FIG. 7B), with higher molar excess of NAC over client resulting in greater aggregation suppression. Such an observation is consistent with findings on other ATP-independent chaperones that bind their substrates weakly, such that an excess of chaperone is required to enable chaperone binding to compete effectively with aggregation. Importantly, NAC is an abundant protein in vivo and is at least stoichiometric with the ribosome (Raue et al., 2007), which would enable effective chaperoning even for weakly binding clients that are highly aggregation prone. Thus, even if only a small percentage of NAC associates with misfolded Htt substrates at any given time, rapid binding and release, combined with potential remodeling of the protein client in the bound state could also enhance folding and decrease the probability of aggregation. This would enable these proteins to remain soluble so that they can fold spontaneously, or be bound by other chaperones that complete folding or target misfolded proteins to degradation pathways (Balchin et al., 2016; Saibil, 2013).

Figure 5E:
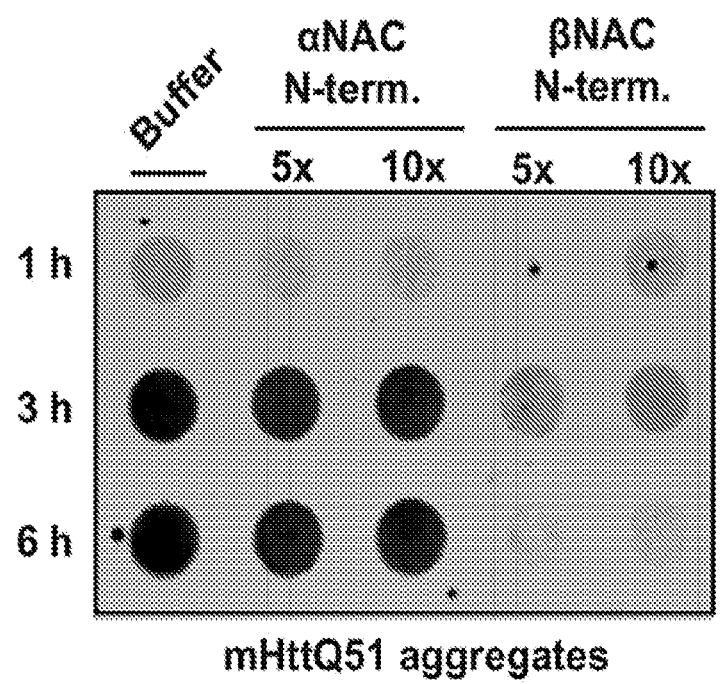

The discovery that just the N-terminus of βNAC is sufficient to potently suppress mutant PolyQ aggregation in vitro as well as necessary to delay age-associated paralysis in C. elegans, has important implications. It highlights a potential general binding mechanism of chaperones to mutant PolyQ substrates. The positively charged nature of the βNAC N-terminus is central to its ability to suppress mHtt aggregation. While the PolyQ itself is uncharged, its polarity can still take part in weak electrostatic interactions with a charged surface like the βNAC N-terminus. Indeed, hydrophilic regions have been associated with chaperone-substrate recognition patterns in addition to the more canonical hydrophobic regions. For example, the TRiC chaperonin, a potent suppressor of mHtt aggregation and toxicity, contains bipartite hydrophilic and hydrophobic substrate recognition sites (Joachimiak et al., 2014). It has been proposed that both of these domains may recognize either hydrophobic or hydrophilic regions of mHtt to mediate suppression of aggregation (Joachimiak et al., 2014; Tam et al., 2006; Tam et al., 2009). DNAJB6 suppresses aggregation of expanded PolyQ tracts through a serine/threonine-rich domain, which disrupts formation of stabilizing hydrogen bonding among the PolyQ residues (Kakkar et al., 2016). It is intriguing that there seems to be specificity with respect to charge while the N-terminal region of the αNAC subunit is also highly charged, it is net negatively charged and has little to no effect on Htt aggregation (FIG. 5E). Thus, it seems that an overall net positive charge is specific for suppression of PolyQ aggregation, but reasons why are still unclear.

Finally, the ability of the βNAC N-terminal peptide to suppress aggregation makes this an important sequence for possible therapeutic development. There is little homology between Huntingtin and Ataxin-3 besides the shared expanded PolyQ domain, suggesting that just the βNAC N-terminal peptide itself is highly potent in suppressing PolyQ-mediated amyloid aggregation. Since NAC-mediated suppression of amyloidogenic aggregation of Aβ40 is independent of the βNAC N-terminal region it is likely that additional domains or interfaces of NAC have chaperone activity against different determinants in amyloid or misfolded intermediates. Thus, NAC may act as a pleiotropic chaperone in vivo for many different misfolded substrates. How NAC is able to recognize different misfolded substrates is an intriguing question for further exploration. In sum, these data provide for the first time a mechanistic understanding of a new chaperone activity of NAC off the ribosome which highlights a novel recognition mechanism of chaperone-substrate interaction and provides a new possible avenue for a peptide-based therapeutics approach in Huntington's disease and related PolyQ disorders.

Material and Methods

Protein Purification

PolyQ51 and mHttQ51 plasmids were constructed as previously described (Tam et al., 2006). Proteins were expressed in Rosetta 2(DE3) pLysS competent cells (Agilent Technologies) in LB media supplemented with carbenicillin and chloramphenicol. Cultures were induced with 1 mM IPTG for 2.5 h at 16° C. For purification, pellets were resuspended in 50 mM sodium phosphate, pH 8.0; 150 mM NaCl; 1 mM EDTA and lysed using an Emulsiflex (Avestin). Lysate was incubated with GSH-Sepharose resin (GE Healthcare) and washed with 0.1% (v/v) Triton, 500 mM NaCl, and 5 mM Mg-ATP before eluting protein with 15 mM glutathione. Protein was concentrated, and buffer exchanged with 50 mM Tris-HCl, pH 8.0; 100 mM NaCl; 5% (v/v) glycerol. Concentrated protein was 0.2 m filtered before storage at −80° C.

Wild-type NAC and NAC mutants from both human and *C. elegans* were recombinantly expressed in Rosetta (DE3) cells as His-SUMO fusion constructs. Cultures were induced with 0.5 mM IPTG over night at 20° C. Cell pellets were resuspended in lysis buffer (20 mM sodium phosphate pH 7.5, 300 mM NaCl, 6 mM MgCl$_2$, 2 mM β-mercaptoethanol, 2 mM PMSF, 10 μg/ml DNase I, 10% (v/v) glycerol) and lysed by French Press. Proteins were captured using Ni-IDA matrix (Protino; Macherey-Nagel) and eluted with lysis buffer containing 250 mM imidazole. Elution fractions were dialyzed overnight in the presence of 8 μg Ulp-1 per mg protein for proteolytic cleavage of the His-SUMO tag. Ion exchange chromatography using Resource Q column (GE Healthcare) was used for further purification. Elution fractions containing αNAC and βNAC in a 1:1 ratio were pooled, frozen in liquid nitrogen and stored at −80° C.

His-tagged AtxQ78 was purified as described in Scarff et al. (Scarff et al., 2015) using nickel affinity chromatography and size-exclusion chromatography.

Aβ40 peptide was expressed and purified as described previously (Stewart et al., 2017; Walsh et al., 2009). In short, BL21 (DE3) cells were transformed with pETSac-mAβ40. Expression of Aβ40 was induced by the addition of IPTG to a final concentration of 1 mM. The cells were allowed to grow for an additional three hours before collection. Inclusion bodies were extracted from the cells by means of sonication followed by centrifugation. Aβ40 was purified from the inclusion body lysate by Q-Sepharose purification followed by two rounds of SEC. The purified peptides were lyophilized and stored at −20° C. The purity of the peptides was confirmed by SDS-PAGE and LC-MS.

In Vitro Aggregation Assays

Mutant Huntingtin and PolyQ51 aggregation reactions were performed at concentration 3 μM of mHttQ51, 0.044 Units/μl acTEV protease (Invitrogen, Carlsbad, CA, USA), and respective concentrations of Ovalbumin (Sigma) or purified NAC chaperone variants. Aggregation was conducted in TEV reaction buffer (Invitrogen) and incubated at 30° C. AtxQ78 was buffer exchanged into TEV reaction buffer using 7K MWCO Zeba Spin Desalting Columns (Thermo Fisher) to initiate aggregation. AtxQ78 aggregation reactions were performed at 30 μM of Ataxin-3 in reaction buffer (20 mM sodium phosphate pH 7.5, 25 mM NaCl, 6 mM MgCl$_2$, 2 mM DTT, 5% (v/v) glycerol) and incubated at 37° C. Samples at varied time-points were then taken and combined in a 1:1 ratio with a 4% (w/v) SDS, 100 mM DTT solution, boiled for 5 min at 95° C., and stored at −20° C. Samples were then filtered through a 0.22 μm cellulose acetate membrane (Whatman) and washed with 0.1% (w/v) SDS. Membrane was probed using an S-tag antibody (Abcam) for mHttQ51 and PolyQ51, and with a His-tag antibody (Abcam) for AtxQ78.

Thioflavin T Fluorescence Assay

Lyophilized Aβ40 was resuspended at 320 μM in 20 mM sodium phosphate pH 7.4, 0.2 mM EDTA, 0.01% (w/v) sodium azide and stored on ice. The NAC proteins were diluted to 100 μM in storage buffer (20 mM sodium phosphate pH 7.5, 25 mM NaCl, 6 mM MgCl$_2$, 2 mM β-mercaptoethanol, 5% (v/v) glycerol) and buffer exchanged into 20 mM sodium phosphate pH 7.4, 0.2 mM EDTA, 0.01% (w/v) sodium azide, 1× complete mini protease inhibitor, EDTA free (Roche) by means of ZebaSpin 7 kDa MWCO spin columns (Thermo Scientific). Samples were prepared that contained equimolar concentrations of Aβ40 and NAC variants. Thioflavin T was added to a final concentration of 10 μM. The samples were transferred to a 96 well half-area clear bottom microplate (Corning GmbH, Wiesbaden, Germany), with 95 μL of sample in each well. The fluorescence (excitation: 440 nm, emission: 480 nm) was measured using a BMG Omega plate reader (BMG Labtech) incubating samples at 37° C., quiescently.

Transmission Electron Microscopy

After 20 h, samples were taken from the Thioflavin T plate and fixed on carbon coated copper grids, made in house. The samples were negative stained with 2% (w/v) uranyl acetate. The samples were imaged on a JEOL 1400 TEM at the Astbury structural biology laboratory, University of Leeds.

Cell Viability Assays and Real-Time PCR siRNA knockdown was completed using the DharmaFECT reverse transfection protocol. Striatal knock-in cell lines (homozygous wild-type HttQ7/7 and heterozygous mutant HttQ7/111) were plated in 96-well plates (1.25×10^4 cells/well) in complete medium (DMEM with high glucose, 10% FBS) at 32° C. Experiments were plated to have four technical replicates per siRNA treatment for each experiment, with each independent experiment repeated at least three times. 72 hours post transfection, cells were incubated with Cell Titer Glo reagent (Promega) for at least 10 minutes before recording luminescence signal. For real-time PCR (RT-PCR), RNA was harvested from cells using the Zymo Quick-RNA kit, cDNA was synthesized using the iScript kit. RT-PCR was completed using the SYBR Green Master Mix from Biorad and fold-knockdown was calculated using the $2^{-\Delta\Delta Ct}$ method.

Fluorescence Microscopy of Cells

Cells were imaged on a Zeiss LSM 700 confocal microscope (Carl Zeiss). Cells were prepared similarly as above but plated on a poly-lysine coated coverslip in 24-well plate. Post transfection, the cells were stained with a 1:2000 Proteostat solution (Enzo Life Sciences, Farmingdale, NY, USA) for 1 hour, followed by a 0.67 μg/ml Hoechst stain for 5 minutes, prior to imaging. For proteasome inhibition, cells were treated with 5 μM MG132 for 6 hours prior to imaging.

Polysome Analysis in Human Cells

Prior to harvesting, HEK293T cells were treated with 100 μg/ml cycloheximide (CHX) for 5 minutes at 37C. Cells were then washed twice in 100 μg/ml CHX in PBS and harvested in the same buffer on ice. Pelleted cells were then resuspended in lysis buffer (10 mM HEPES pH 7.9, 1.5 mM MgCl$_2$, 10 mM KCl, 0.5 mM DTT, 1% Triton X-100, 100 µg/ml CHX) and lysed by trituration through a 26G needle for 10 passes. The sample was centrifuged at 1500×g for 5 minutes at 4° C. RNA concentration of the supernatant was then measured by Nanodrop. 200 µg (in RNA) of lysate was loaded onto a 12 ml 10-50% (w/v) linear sucrose gradient (Gradient Mate, Biocomp Instruments) prepared in gradient buffer (100 mM KCl, 20 mM HEPES pH 7.6, 5 mM MgCl$_2$, 100 µg/ml CHX, 1 U/µl RNase inhibitor) and centrifuged for 2 h at 36000 rpm in a swinging bucket rotor (SW-41, Beckmann). Gradients were then fractionated from top to bottom with a density gradient fractionator (Brandel), and A260 was monitored to detect cytosolic fractions, ribosomal subunits, monosomes, and polysomes. Data were recorded and processed with WinDaq (Dataq Instruments). For one gradient, 15 fractions with 1 ml each were collected. For subsequent western analysis, 500 µl of gradient buffer and 10 µl of Strataclear resin slurry (Agilent Technologies) was added to each fraction and incubated on rotation at 4° C. Fractions were centrifuged twice at 3000×g at 4° C. for 5 min to remove supernatant. The remaining resin was then resuspended in 20 µl 2× Laemmli Buffer, centrifuged at 3000×g for 5 min, and the residual supernatant was loaded into an SDS-PAGE gel and then transferred onto a nitrocellulose membrane. Different dilutions of primary antibodies were applied (1:400 anti-βNAC, 1:3000 anti-RPLP0).

Sulfo-NHS Peptide Labeling

NAC N-terminal peptides were ordered from Genscript. Peptides were dissolved to 1 mM in 0.1 M sodium carbonate buffer, pH 8.5. Peptide solutions were added to a 25-fold molar excess of Sulfo-NHS Acetate (Thermo Scientific, Waltham, MA, USA) to amine groups in the sample and incubated for 1 hour at room temperature. Reaction was quenched using a 1 M Tris-HCl, pH 7.5 solution. To quantify the efficiency of this labelling, a lysine standard curve was established; samples were assayed for free primary amines by adding 0.01% (w/v) TNBS in 0.1 M sodium bicarbonate, pH 8.5 solution (G Biosciences) to each sample and standard, and incubated at 37° C. for 2 hours. 10% SDS and 1 N HCl was then added to stop the reaction. Absorbance was measured at 335 nm.

Chemical Crosslinking and Mass Spectrometry

For crosslinking AtxQ78 was buffer exchanged into 10 mM sodium phosphate (pH 7.2) and added to NAC at a 1:1 ratio (20 µM NAC+20 µM AtxQ78). A 1:1 mixture of BS$^3$-d$^0$ and BS$^3$-d$^4$ was added to the proteins at 20× and 50× molar excess and the reaction allowed to proceed at room temperature for 1 hour before quenching with the addition of 50 mM Tris-Cl (pH 7.5). Samples were diluted with 2× loading buffer and separated on Tris-tricine gels followed by staining with InstantBlue (Expedeon).

Aβ40 (18 µM) was incubated with purified NAC in a 1:1 molar ratio in Aβ aggregation buffer (20 mM sodium phosphate pH 7.5, 0.2 mM EDTA, 0.01% (w/v) NaN$_3$) at 37° C. for 2 h. BS$^3$-h$^{12}$d$^{12}$ was added to the proteins at 20× molar excess and incubated for 30 min at 37° C. before quenching with 50 mM NH$_4$HCO$_3$. Crosslinked samples were gel-filtrated using a Superdex 75 column (GE Healthcare) and fractions containing crosslinked Aβ40-NAC complexes subjected to co-immunoprecipitation using Aβ antibody 6E10 (Biozol). Captured proteins were denatured with 1×SDS sample buffer under non-reducing conditions to avoid splitting of the antibody in heavy and light chains.

Gel pieces containing the crosslinked complexes were washed with 25 mM ammonium bicarbonate (pH 7.8) for 1 h with shaking. The solution was removed and the pieces destained three times with 25 mM ammonium bicarbonate in 60% acetonitrile. Gel pieces were dehydrated with 100% acetonitrile for 10 min and left to air-dry in a laminar flowhood for 1 h. Rehydration of the gel pieces was achieved by adding 0.1 mg/ml trypsin solution and incubating the samples on ice for 30 min. Excess trypsin was removed and the samples were incubated at 37° C. and 1000 rpm overnight. Peptides were extracted from the gel using 3 washes with 60% acetonitrile/5% formic acid. The extracts were pooled and concentrated using a SpeedVac before being analyzed using a nanoACQUITY LC-system coupled to a Synapt HDMS G2Si mass spectrometer. Peptides were injected onto a C18 column equilibrated with 0.1% formic acid in water and eluted using an increasing gradient of 0.1% formic acid in acetonitrile over 60 min at a flow rate of 0.3 µl/min. The Synapt HDMS G2Si was operated in positive mode using a capillary voltage of 3.0 kV, cone voltage of 40 V, backing pressure of 3.6 mbar and a trap bias of 2.0 V. The source temperature was 80° C. and the trap pressure was 8.70×10$^{-3}$ mBar. Glu-fibrinogen and Leucine Enkephalin were infused as lock mass calibrants. Data acquisition was achieved using Data Dependent Analysis (DDA) with a one second MS scan over an m/z range of 250-3000 being followed by three 1 s MS/MS scans taken from the five most intense ions in the MS spectrum over an m/z range of 50-2000. Data processing was performed using the MassLynx v4.1 suite of software supplied with the mass spectrometer and PEAKS 7/8 (Bioinformatics Solutions). Crosslinks were identified using StavroX software (Götze et al., 2012) and verified manually.

Luciferase Refolding Assay

Luciferase refolding activity was measured as previously described (Sun et al., 2012). Recombinant luciferase (2.5 µM) was chemically denatured for 45 min at room temperature in denaturing buffer (25 mM HEPES/KOH, pH 7.4, 50 mM KCl, 15 mM MgCl$_2$, 1 mM ATP, 10 mM DTT, 0.05 mg/mL BSA, 5 M GdmCl). To test for refolding activity 0.02 µM denatured luciferase was preincubated in the presence or absence of 0.02 µM NAC variants for 15 min at room temperature. Luciferase refolding was induced by addition of 3.2 µM CeHsc70 (HSP-1), 0.8 µM CeHsp40 (DNJ-13) and luminescence buffer (75 mM HEPES/KOH, pH 7.4, 50 mM KCl, 15 mM MgCl$_2$, 1 mM ATP, 2 mM DTT, 0.05 mg/mL BSA, 240 µM Coenzyme A, 0.1 mM luciferin, 10 mM PEP, 50 µg/mL pyruvate kinase). Luminescence was measured in 96-well LIA-plates (Greiner) over 2 hours at room temperature in a microplate reader (BertholdTech TriStar2S).

C. elegans Methods

Strains and Transformation

Worms were cultured according to standard techniques with E. coli OP50 as food source (Brenner, 1974). Transgenic strains were generated using standard microinjection protocols (Mello and Fire, 1995). Constructs for overexpression of NAC in body wall muscles were generated by cloning the coding sequences of icd-1 (βNAC) and icd-2 (αNAC) into a vector containing the myo-3 promoter and the unc-54 3'-untranslated region (UTR). The NAC genes were N-terminally tagged with 3×FLAG. Mutant NAC constructs were generated by standard mutagenesis protocols. AM140 (unc-54p::Q35::YFP) and FlucDM-EGFP (unc-54p::luciferase::GFP) worms were injected with 25 ng/µl of each NAC plasmid together with myo-2p::mCherry (2.5 ng/µl) and DNA ladder (100 ng/µl, GeneRuler 1 kb, Thermo Scientific). Control strains were obtained by injecting 50 ng/µl empty vector, 2.5 ng/µl myo-2p::mCherry and 100 ng/µl DNA ladder. For each transformation, at least two independent transgenic lines carrying extrachromosomal arrays were obtained showing similar results. Detailed strain information is available in Table 3.

Synchronization of C. Elegans

Synchronization of worms for microscopic studies was carried out by a timed egg-lay for 5 h. Large age-synchronized C. elegans cultures for SDD-AGE analyses were obtained by collecting embryos from gravid adult worms using a 20% alkaline hypochlorite bleaching for 5 minutes. Embryos were allowed to hatch overnight in M9 buffer to get arrested L1s. Transgenic L1 larvae were sorted based on the myo-2p::mCherry marker using a COPAS FlowPilot system (Union Biometrica). The synchronized, transgenic L1s were transferred to OP50 seeded plates and incubated at 20° C. After two days the young adult worms were transferred to new plates containing 150 µM 5-fluorodeoxyuridine (LKT Laboratories) to prevent the culture from reproducing.

Fluorescence Microscopy of Worms

Worms were immobilized on 3% agarose pads and anaesthetized using 25 mM levamisole (LKT Laboratories). Images were taken with a confocal laser-scanning microscope TCS SP8 (Leica) with 5× (whole body images) and 63× objectives (head region). Images were adjusted as necessary in Fiji (ImageJ) using cropping, brightness and contrast tools.

SDD-AGE

SDD-AGE was carried out as previously described (Halfmann and Lindquist, 2008). For sample preparation, worms were extracted in lysis buffer (100 mM Tris-Cl pH 7.5, 50 mM NaCl, 10 mM β-mercaptoethanol, 1× complete protease inhibitor) by sonication (four times, 10 pulses, duty cycle=40, output control=2; Branson sonifier). Lysed worms were centrifuged for 1 min at 500 g to remove debris and the supernatant was transferred to a new tube. % volume of 4×SDD-AGE sample buffer (2×TAE, 20% glycerol, 8% SDS, 0.05% bromphenol blue) was added to the lysates and incubated for 15 min at RT. Samples were loaded onto a 1.2% agarose gel in 1×TAE buffer (40 mM Tris-Cl, pH 7.6, 20 mM acetic acid, 1 mM EDTA) containing 0.1% SDS and proteins were blotted on nitrocellulose membranes by capillary transfer in 1× Tris buffer (150 mM NaCl, 50 mM Tris-Cl pH 7.5) over night at room temperature. The membrane was analyzed using an anti-GFP antibody (Covance).

Polysome Analysis

C. elegans N2 worms were cultivated in liquid culture at 20° C. in presence of E. coli OP50 as food source. Day 2 post-L4 worms were harvested on ice with 0.1 M NaCl and separated from bacteria via sucrose floatation. After an additional washing step, the nematodes were flash frozen in liquid nitrogen. Worm pellets were cryo-genic grinded using a cryo-mill (Retsch) for 30 sec at 22 Hz. Frozen worm powder was resuspended in lysis buffer (30 mM HEPES/KOH pH 7.4, 50 mM KoAc, 5 mM $MgCl_2$, 5% (w/v) mannitol, 100 µg/mL cycloheximide, 2 mM β-mercaptoethanol, 1× complete protease inhibitor) and centrifuged at 18,000 g for 15 min at 4° C. The supernatant was adjusted to 20 $A_{260}$ U/ml and 500 µl were loaded on a sucrose gradient (15%-45% in lysis buffer). Ribosomal species were separated by ultracentrifugation (TH-641 rotor) at 39,000 rpm for 2.5 hours (4° C.). Gradients were fractionated using a density gradient fractionator (Teledyne Isco, Inc.) monitoring the $A_{254}$ and fractions were directly analyzed by immunoblotting.

Paralysis Assay

To analyze the percentage of paralyzed worms, 100 semi-synchronized (timed egg lay for 5 h) young adult worms of each strain were placed on a plate containing 150 µM 5-fluorodeoxyuridine. Screening of paralyzed worms was started at day 6 of adulthood. Worms were scored as paralyzed when they only moved their heads but failed to undergo a full body wave propagation upon repeated prodding with a platinum wire worm picker.

Antibodies

Commercial antibodies used throughout this study were GFP (Covance, MMS-118P), FLAG (Sigma, F1804), Actin (Santa Cruz, sc-47778), and uL16 (Abgent, Aβ176039). Polyclonal antibody against C. elegans NAC (αNAC+ βNAC) was described previously (Kirstein-Miles et al., 2013). Antibody against uL24 was raised in rabbits immunized with recombinant full-length C. elegans RPL-26 protein. Tubulin antibodies were a kind gift from Thomas Mayer, University of Konstanz.

REFERENCES

Balchin, D., Hayer-Hartl, M., and Hartl, F. U. (2016). In vivo aspects of protein folding and quality control. *Science* 353, aac4354.

Brenner, S. (1974). The genetics of *Caenorhabditis elegans*. *Genetics* 77, 71-94.

Chae, J. I., Kim, D. W., Lee, N., Jeon, Y. J., Jeon, I., Kwon, J., Kim, J., Soh, Y., Lee, D. S., Seo, K. S., et al. (2012). Quantitative proteomic analysis of induced pluripotent stem cells derived from a human Huntington's disease patient. *Biochem J* 446, 359-371.

Cohen, E., Bieschke, J., Perciavalle, R. M., Kelly, J. W., and Dillin, A. (2006). Opposing activities protect against age-onset proteotoxicity. *Science* 313, 1604-1610.

del Alamo, M., Hogan, D. J., Pechmann, S., Albanese, V., Brown, P. O., and Frydman, J. (2011). Defining the specificity of cotranslationally acting chaperones by systematic analysis of mRNAs associated with ribosome-nascent chain complexes. *PLoS Biol* 9, e1001100.

Duttler, S., Pechmann, S., and Frydman, J. (2013). Principles of cotranslational ubiquitination and quality control at the ribosome. *Mol Cell* 50, 379-393.

Gamerdinger, M., Hanebuth, M. A., Frickey, T., and Deuerling, E. (2015). The principle of antagonism ensures protein targeting specificity at the endoplasmic reticulum. *Science* 348, 201-207.

Gotze, M., Pettelkau, J., Schaks, S., Bosse, K., Ihling, C. H., Krauth, F., Fritzsche, R., Kuhn, U., and Sinz, A. (2012).

StavroX—a software for analyzing crosslinked products in protein interaction studies. *J Am Soc Mass Spectrom* 23, 76-87.

Götze, M., Pettelkau, J., Schaks, S., Bosse, K., Ihling, C. H., Krauth, F., Fritzsche, R., Kühn, U., and Sinz, A. (2012). StavroX-A Software for Analyzing Crosslinked Products in Protein Interaction Studies. *Journal of The American Society for Mass Spectrometry* 23, 76-87.

Gupta, R., Kasturi, P., Bracher, A., Loew, C., Zheng, M., Villella, A., Garza, D., Hartl, F. U., and Raychaudhuri, S. (2011). Firefly luciferase mutants as sensors of proteome stress. *Nat Methods* 8, 879-884.

Halfmann, R., and Lindquist, S. (2008). Screening for amyloid aggregation by Semi-Denaturing Detergent-Agarose Gel Electrophoresis. *J Vis Exp*.

He, L., Sharpe, T., Mazur, A., and Hiller, S. (2016). A molecular mechanism of chaperone-client recognition. *Sci Adv* 2, el 601625.

Horowitz, S., Salmon, L., Koldewey, P., Ahlstrom, L. S., Martin, R., Quan, S., Afonine, P. V., van den Bedem, H., Wang, L., Xu, Q., et al. (2016). Visualizing chaperone-assisted protein folding. *Nat Struct Mol Biol* 23, 691-697.

Joachimiak, L. A., Walzthoeni, T., Liu, C. W., Aebersold, R., and Frydman, J. (2014). The structural basis of substrate recognition by the eukaryotic chaperonin TRiC/CCT. *Cell* 159, 1042-1055.

Kakkar, V., Mansson, C., de Mattos, E. P., Berginsk, S., van der Zwaag, M., van Waarde, M., Kloosterhuis, N. J., Melki, R., van Cruchten, R. T. P., Al-Karadaghi, S., et al. (2016). The S/T-Rich Motif in the DNAJB6 Chaperone Delays Polyglutamine Aggregation and the Onset of Disease in a Mouse Model. *Mol Cell* 62, 272-283.

Kim, S. H., Shim, K. S., and Lubec, G. (2002). Human brain nascent polypeptide-associated complex alpha subunit is decreased in patients with Alzheimer's disease and Down syndrome. *J Investig Med* 50, 293-301.

Kim, Y. E., Hipp, M. S., Bracher, A., Hayer-Hartl, M., and Hartl, F. U. (2013). Molecular chaperone functions in protein folding and proteostasis. *Annu Rev Biochem* 82, 323-355.

Kirstein-Miles, J., Scior, A., Deuerling, E., and Morimoto, R. I. (2013). The nascent polypeptide-associated complex is a key regulator of proteostasis. *EMBO J* 32, 1451-1468.

Labbadia, J., and Morimoto, R. I. (2013). Huntington's disease: underlying molecular mechanisms and emerging concepts. *Trends Biochem Sci* 38, 378-385.

Liu, Y., Hu, Y., Li, X., Niu, L., and Teng, M. (2010). The crystal structure of the human nascent polypeptide-associated complex domain reveals a nucleic acid-binding region on the NACA subunit. *Biochemistry* 49, 2890-2896.

Martin, E. M., Jackson, M. P., Gamerdinger, M., Gense, K., Karamonos, T. K., Humes, J. R., Deuerling, E., Ashcroft, A. E., and Radford, S. E. (2018). Conformational flexibility within the nascent polypeptide-associated complex enables its interactions with structurally diverse client proteins. *J Biol Chem* 293, 8554-8568.

Matos, C. A., de Macedo-Ribeiro, S., and Carvalho, A. L. (2011). Polyglutamine diseases: the special case of ataxin-3 and Machado-Joseph disease. *Prog Neurobiol* 95, 26-48.

Mello, C., and Fire, A. (1995). *DNA transformation. Methods Cell Biol* 48, 451-482.

Morley, J. F., Brignull, H. R., Weyers, J. J., and Morimoto, R. I. (2002). The threshold for polyglutamine-expansion protein aggregation and cellular toxicity is dynamic and influenced by aging in Caenorhabditis elegans. *Proc Natl Acad Sci USA* 99, 10417-10422.

Ott, A. K., Locher, L., Koch, M., and Deuerling, E. (2015). Functional Dissection of the Nascent Polypeptide-Associated Complex in Saccharomyces cerevisiae. *PLoS One* 10, e0143457.

Pech, M., Spreter, T., Beckmann, R., and Beatrix, B. (2010). Dual binding mode of the nascent polypeptide-associated complex reveals a novel universal adapter site on the ribosome. *J Biol Chem* 285, 19679-19687.

Pechmann, S., Willmund, F., and Frydman, J. (2013). The ribosome as a hub for protein quality control. *Mol Cell* 49, 411-421.

Preissler, S., and Deuerling, E. (2012). Ribosome-associated chaperones as key players in proteostasis. *Trends Biochem Sci* 37, 274-283.

Raue, U., Oellerer, S., and Rospert, S. (2007). Association of protein biogenesis factors at the yeast ribosomal tunnel exit is affected by the translational status and nascent polypeptide sequence. *J Biol Chem* 282, 7809-7816.

Saibil, H. (2013). Chaperone machines for protein folding, unfolding and disaggregation. *Nat Rev Mol Cell Biol* 14, 630-642.

Saio, T., Guan, X., Rossi, P., Economou, A., and Kalodimos, C. G. (2014). Structural basis for protein antiaggregation activity of the trigger factor chaperone. *Science* 344, 1250494.

Sala, A. J., Bott, L. C., and Morimoto, R. I. (2017). Shaping proteostasis at the cellular, tissue, and organismal level. *J Cell Biol* 216, 1231-1241.

Saunders, H. M., and Bottomley, S. P. (2009). Multi-domain misfolding: understanding the aggregation pathway of polyglutamine proteins. *Protein Eng Des Sel* 22, 447-451.

Scarff, C. A., Almeida, B., Fraga, J., Macedo-Ribeiro, S., Radford, S. E., and Ashcroft, A. E. (2015). Examination of Ataxin-3 (atx-3) Aggregation by Structural Mass Spectrometry Techniques: A Rationale for Expedited Aggregation upon Polyglutamine (polyQ) Expansion. *Mol Cell Proteomics* 14,1241-1253.

Schroder, H., Langer, T., Hartl, F. U., and Bukau, B. (1993). DnaK, DnaJ and GrpE form a cellular chaperone machinery capable of repairing heat-induced protein damage. *EMBO J* 12, 4137-4144.

Shen, D., Coleman, J., Chan, E., Nicholson, T. P., Dai, L., Sheppard, P. W., and Patton, W. F. (2011). Novel cell- and tissue-based assays for detecting misfolded and aggregated protein accumulation within aggresomes and inclusion bodies. *Cell Biochem Biophys* 60, 173-185.

Stewart, K. L., Hughes, E., Yates, E. A., Middleton, D. A., and Radford, S. E. (2017). Molecular Origins of the Compatibility between Glycosaminoglycans and Abeta40 Amyloid Fibrils. *J Mol Biol* 429, 2449-2462.

Stull, F., Koldewey, P., Humes, J. R., Radford, S. E., and Bardwell, J. C. A. (2016). Substrate protein folds while it is bound to the ATP-independent chaperone Spy. *Nat Struct Mol Biol* 23, 53-58.

Sun, L., Edelmann, F. T., Kaiser, C. J., Papsdorf, K., Gaiser, A. M., and Richter, K. (2012). The lid domain of Caenorhabditis elegans Hsc70 influences ATP turnover, cofactor binding and protein folding activity. *PLoS One* 7, e33980.

Tam, S., Geller, R., Spiess, C., and Frydman, J. (2006). The chaperonin TRiC controls polyglutamine aggregation and toxicity through subunit-specific interactions. *Nat Cell Biol* 8, 1155-1162.

Tam, S., Spiess, C., Auyeung, W., Joachimiak, L., Chen, B., Poirier, M. A., and Frydman, J. (2009). The chaperonin TRiC blocks a huntingtin sequence element that promotes the conformational switch to aggregation. *Nat Struct Mol Biol* 16, 1279-1285.

Trettel, F., Rigamonti, D., Hilditch-Maguire, P., Wheeler, V. C., Sharp, A. H., Persichetti, F., Cattaneo, E., and MacDonald, M. E. (2000). Dominant phenotypes produced by the HD mutation in STHdh(Q111) striatal cells. *Hum Mol Genet* 9, 2799-2809.

Walsh, D. M., Thulin, E., Minogue, A. M., Gustavsson, N., Pang, E., Teplow, D. B., and Linse, S. (2009). A facile method for expression and purification of the Alzheimer's disease-associated amyloid beta-peptide. *FEBS J* 276, 1266-1281.

Wang, F., Durfee, L. A., and Huibregtse, J. M. (2013). A cotranslational ubiquitination pathway for quality control of misfolded proteins. *Mol Cell* 50, 368-378.

Wang, L., Zhang, W., Wang, L., Zhang, X. C., Li, X., and Rao, Z. (2010). Crystal structures of NAC domains of human nascent polypeptide-associated complex (NAC) and its alphaNAC subunit. *Protein Cell* 1, 406-416.

Wang, S., Sakai, H., and Wiedmann, M. (1995). NAC covers ribosome-associated nascent chains thereby forming a protective environment for regions of nascent chains just emerging from the peptidyl transferase center. *J Cell Biol* 130, 519-528.

Wegrzyn, R. D., Hofmann, D., Merz, F., Nikolay, R., Rauch, T., Graf, C., and Deuerling, E. (2006). A conserved motif is prerequisite for the interaction of NAC with ribosomal protein L23 and nascent chains. *J Biol Chem* 281, 2847-2857.

Wiedmann, B., Sakai, H., Davis, T. A., and Wiedmann, M. (1994). A protein complex required for signal-sequence-specific sorting and translocation. *Nature* 370, 434-440.

Example 2

Dual Role of Ribosome-Binding Domain of NAC as a Potent Suppressor of Protein Aggregation and Aging-Related Proteinopathies

INTRODUCTION

The eukaryotic chaperonin 'KS1" TRiC/CCT controls polyQ aggregation and toxicity in neuronal cells. We found that just a single subunit of TRiC complex, CCT1, can also directly inhibit the aggregation and neurotoxicity associated with the causative agent of Huntington's disease (polyQ-expanded huntingtin exon1) by itself. We further narrowed down the active aggregation suppression domain to just a single domain of this subunit, the 140 amino acid apical domain of CCT1 (ApiCCT1), which prevents formation of toxic aggregates.

Although not wishing to be bound by a particular theory, the specific mechanism by which TRiC or its isolated domain derivatives suppresses aggregation may involve sequestering the hydrophobic surface of the N-terminal 17 amino acids (N17) of the Huntingtin exon1 and preventing Huntingtin self-oligomerization into toxic aggregation species.

More recently, we discovered another molecular chaperone complex, the nascent polypeptide-associated complex (NAC), also effectively suppress polyQ aggregation both in vivo and in vitro (see Example 1). We have shown that NAC can suppress aggregation and proteotoxicity of the aggregation-prone expanded polyQ proteins Htt and Ataxin-3. This seems to be a novel mechanism of NAC as polyQ aggregation suppression seems to be independent of the canonical ribosome-associated chaperone function of NAC. Interestingly, in contrast to TRiC domains, which bind to the N17 segment of Huntingtin, NAC seems to act directly on the expanded polyQ stretch. We have isolated this chaperone activity to a small ~40 amino acid sequence within the N-terminal domain of the beta subunit of NAC. It has been shown that this small peptide alone can supress mHttQ51 aggregation, even better than the full-length NAC chaperone.

Based on these results, we designed a fusion protein comprising the apical domain of CCT1 fused with the bNAC N-terminal sequence at its C-terminus (ApiCCT1-bNAC) as a unique inhibitor of polyglutamine aggregation and toxicity, particularly because each individual component interacts with two adjacent domains within the Htt Exon 1, both of which have been shown to modulate huntingtin aggregation and toxicity. This modified form of ApiCCT1 can better sequester early-stage huntingtin oligomers before they aggregate further into toxic fibril formations and significantly slow down the rate of huntingtin aggregation. Modified apical domains of this chaperonin can also be used to prevent aggregation and toxicity for other neurodegenerative diseases, including Parkinson's and Alzheimer's disease.

This novel approach provides a robust avenue for therapeutic applications with several advantages over existing approaches: (i) while other chaperones like Hsp70 and Hsp40 promiscuously interact with a wide range of substrates and cellular clients, 'KS2" TRiC, and in particular ApiCCT1, has a more specific client list. Thus, technologies enhancing ApiCCT1 activity should have minimal off-target effects on the cellular protein folding machinery. (ii) The apical domain does not functionally complement the normal cellular function of the TRiC complex, which again, minimizes the potential indirect impacts on cellular protein folding. (iii) ApiCCT1 along with its modified form ApiCCT1-bNAC are both small and stable polypeptides serving as a versatile scaffold for the design of optimized aggregation inhibitors beyond Huntington's disease. (iv) The fusion of both ApiCCT1 and the bNAC N-terminal peptide allow for highly specific targeting to huntingtin exon1s N17 and polyQ domains, making it a good foundation for the development and optimization of inhibitors of Htt aggregation and disease.

We have shown that elevated levels of the full length CCT1 subunit suppress neurotoxicity associated with Huntington's Disease in yeast model systems and tissue culture cells. In a system with purified components, ApiCCT1 specifically and efficiently inhibits polyQ aggregation of huntingtin exon1. With attachment of the bNAC N-terminal sequence, the fused protein works even more potently to inhibit huntingtin exon1 aggregation, as it can suppress aggregation even at sub-molar ratios.

TABLE 1a

| | | | | | | Intra- and inter-NAC crosslinks |
|---|---|---|---|---|---|---|
| Score | m/z | z | M + H+ | Calculated | Deviation | Peptide 1 |
| 231 | 594.99 | 3 | 1782.956 | 1782.953 | 1.31 | [QAK] |
| 124 | 593.648 | 3 | 1778.929 | 1778.928 | 0.47 | [VAEAAGLGDHIDKQAK] (SEQ ID NO: 9) |
| 111 | 1140.91 | 3 | 3420.702 | 3420.686 | 4.87 | [DDGTVIHFNNPK] (SEQ ID NO: 10) |
| 106 | 464.925 | 3 | 1392.76 | 1392.759 | 0.33 | [KLQAQQEHVR] (SEQ ID NO: 11) |
| 95 | 550.95 | 3 | 1650.834 | 1650.837 | −1.49 | [QKEVK] (SEQ ID NO: 12) |
| 83 | 817.758 | 3 | 2451.258 | 2451.255 | 1.41 | [IEDLTQHAQMSAIENLKPTR] (SEQ ID NO: 13) |
| 75 | 711.375 | 3 | 2132.111 | 2132.109 | 0.61 | [VAEAAGLGDHIDKQAKQSR] (SEQ ID NO: 14) |
| 73 | 539.313 | 3 | 1615.926 | 1615.928 | −1.36 | [IKKLQAQQEHVR] (SEQ ID NO: 15) |
| 66 | 823.088 | 3 | 2467.251 | 2467.25 | 0.43 | [IEDLTQHAQmSAIENLKPTR] (SEQ ID NO: 13) |
| 66 | 640.038 | 3 | 1918.099 | 1918.105 | −2.95 | [SKNILFVINKPDVFK] (SEQ ID NO: 16) |
| 61 | 593.647 | 3 | 1778.928 | 1778.928 | −0.37 | [VAEAAGLGDHIDKQAK] (SEQ ID NO: 9) |
| 57 | 632.037 | 3 | 1894.097 | 1894.101 | −1.82 | [LGLK] (SEQ ID NO: 17) |
| 52 | 551.948 | 3 | 1653.829 | 1653.83 | 0.35 | [VCIRK] (SEQ ID NO: 18) |
| 52 | 1139.56 | 3 | 3416.655 | 3416.66 | −1.62 | [DDGTVIHFNNPK] (SEQ ID NO: 10) |
| 52 | 1139.56 | 3 | 3416.655 | 3416.66 | −1.62 | [DDGTVIHFNNPKVQTSVPANTFSVTGSADNK] (SEQ ID NO: 19) |
| 48 | 676.735 | 3 | 2028.19 | 2028.189 | 0.23 | [KSKNILFVINKPDVFK] (SEQ ID NO: 20) |
| 45 | 602.312 | 3 | 1804.92 | 1804.922 | −0.98 | [IGGKGTPR] (SEQ ID NO: 21) |
| 44 | 823.085 | 3 | 2467.241 | 2467.25 | −3.39 | [IEDLTQHAQmSAIENLKPTR] (SEQ ID NO: 13) |
| 44 | 817.756 | 3 | 2451.254 | 2451.255 | −0.36 | [IEDLTQHAQMSAIENLKPTR] (SEQ ID NO 13) |
| 43 | 712.717 | 3 | 2136.136 | 2136.134 | 0.82 | [LGPDGK] (SEQ ID NO: 22) |
| 42 | 817.758 | 3 | 2451.259 | 2451.255 | 1.59 | [IEDLTQHAQMSAIENLKPTR] (SEQ ID NO: 13) |
| 37 | 906.168 | 3 | 2716.488 | 2716.495 | −2.73 | [QITEMLPGILNQLGPESLTHLKK] (SEQ ID NO: 23) |
| 36 | 911.505 | 3 | 2732.502 | 2732.49 | 4.16 | [QITEmLPGILNQLGPESLTHLKK] (SEQ ID NO: 23) |
| 35 | 433.451 | 5 | 2163.225 | 2163.229 | −2.11 | [IGGKGTPR] (SEQ ID NO: 21) |
| 35 | 747.379 | 3 | 2240.121 | 2240.131 | −4.09 | [QVTGVSR] (SEQ ID NO: 24) |
| 34 | 607.644 | 3 | 1820.917 | 1820.917 | −0.13 | [IGGKGTPR] (SEQ ID NO: 21) |
| 31 | 751.723 | 3 | 2253.153 | 2253.162 | −3.61 | {mTGSTETR] (SEQ ID NO: 25) |
| 29 | 816.777 | 3 | 2448.317 | 2448.313 | 1.8 | [AIAERIK] (SEQ ID NO: 26) |
| 28 | 711.375 | 3 | 2132.111 | 2132.109 | 0.83 | [LGPDGK] (SEQ ID NO: 22) |
| 26 | 556.282 | 3 | 1666.831 | 1666.832 | −0.36 | {mTGSTETROKEVK] (SEQ ID NO: 27) |
| 26 | 772.085 | 3 | 2314.24 | 2314.236 | 1.82 | [QAKQSR] (SEQ ID NO: 29) |
| 25 | 772.085 | 3 | 2314.241 | 2314.236 | 2.25 | [QAKQSR] (SEQ ID NO: 29) |
| 24 | 978.107 | 3 | 2932.308 | 2932.319 | −3.91 | {mTGSTETR] (SEQ ID NO: 25) |
| 24 | 691.408 | 3 | 2072.21 | 2072.201 | 4.58 | [IGGK] (SEQ ID NO: 30) |
| 23 | 691.408 | 3 | 2072.21 | 2072.212 | −0.84 | [KAR] |
| 22 | 556.282 | 3 | 1666.831 | 1666.832 | −0.36 | [EVK] |
| 21 | 1032.54 | 3 | 3095.601 | 3095.612 | −3.42 | [SEKKARKLFSK] (SEQ ID NO: 31) |
| 20 | 478.29 | 3 | 1432.854 | 1432.852 | 1.2 | [QSR] |
| 18 | 550.277 | 3 | 1648.815 | 1648.821 | −3.71 | {mTGSTETRQKEVK] (SEQ ID NO: 27) |
| 18 | 736.346 | 3 | 2207.025 | 2207.029 | −1.93 | {MTGSTETR] (SEQ ID NO: 25) |
| 160 | 519.74 | 2 | 1038.473 | 1038.477 | −3.73 | {MTGSTETR] (SEQ ID NO: 25) |
| 151 | 379.233 | 2 | 757.459 | 757.457 | 2.64 | [NKAIR] (SEQ ID NO: 28) |
| 147 | 527.739 | 2 | 1054.472 | 1054.472 | −0.49 | {mTGSTETR] (SEQ ID NO: 25) |
| 134 | 471.275 | 2 | 941.543 | 941.541 | 1.56 | [IGGKGTPR] (SEQ ID NO: 21) |
| 103 | 473.289 | 2 | 945.57 | 945.567 | 3.43 | [IGGK] (SEQ ID NO: 30) |
| 97 | 471.275 | 2 | 941.543 | 941.541 | 1.56 | [IGGK] (SEQ ID NO: 30) |
| 96 | 522.308 | 2 | 1043.609 | 1043.609 | 0.18 | [KLANNVTK] (SEQ ID NO: 32) |
| 91 | 851.991 | 2 | 1702.974 | 1702.978 | −2.29 | [NILFVINKPDVFK] (SEQ ID NO: 33) |
| 90 | 657.393 | 2 | 1313.778 | 1313.779 | −0.76 | [LGLKQVTGVSR] (SEQ ID NO: 34) |
| 87 | 540.556 | 4 | 2159.201 | 2159.204 | −1.38 | [IGGKGTPR] (SEQ ID NO: 21) |
| 87 | 851.993 | 2 | 1702.98 | 1702.978 | 1 | [NILFVINKPDVFK] (SEQ ID NO: 33) |
| 55 | 657.393 | 2 | 1313.778 | 1313.779 | −0.76 | [LGLK] (SEQ ID NO: 17) |
| 53 | 389.739 | 2 | 778.47 | 778.471 | −0.92 | [KLFSK] (SEQ ID NO: 35) |
| 52 | 659.405 | 2 | 1317.803 | 1317.804 | −0.69 | [LGLK] (SEQ ID NO: 17) |
| 48 | 891.98 | 2 | 1782.952 | 1782.953 | −0.89 | [QAK] |
| 47 | 541.561 | 4 | 2163.222 | 2163.229 | −3.56 | [IGGKGTPR] (SEQ ID NO: 21) |
| 45 | 855.928 | 4 | 3420.689 | 3420.686 | 1.03 | [DDGTVIHFNNPK] (SEQ ID NO: 10) |
| 42 | 586.376 | 2 | 1171.745 | 1171.745 | −0.33 | [KLFSKLGLK] (SEQ ID NO: 36) |
| 41 | 473.287 | 2 | 945.567 | 945.567 | 0.66 | [IGGK] (SEQ ID NO: 30) |
| 40 | 783.872 | 2 | 1566.736 | 1566.743 | −4.55 | [NETK] (SEQ ID NO: 37) |
| 36 | 433.452 | 5 | 2163.233 | 2163.229 | 1.42 | [IGGKGTPR] (SEQ ID NO: 21) |
| 29 | 480.293 | 2 | 959.579 | 959.577 | 2.02 | [ALK] |
| 29 | 983.996 | 4 | 3932.961 | 3932.959 | 0.6 | [SPGSDTYIIFGEAKIEDLTQHAQmSAIENLKPTR] (SEQ ID NO: 38) |
| 28 | 796.984 | 2 | 1592.96 | 1592.964 | −2.72 | [VCIRK] (SEQ ID NO: 18) |
| 24 | 562.291 | 5 | 2807.424 | 2807.428 | −1.29 | {MmDSKAIAER] (SEQ ID NO: 39) |
| 24 | 839.19 | 4 | 3353.737 | 3353.741 | −1.17 | [KKVIHK] (SEQ ID NO: 40) |
| 23 | 562.291 | 5 | 2807.424 | 2807.428 | −1.29 | {mMDSKAIAER] (SEQ ID NO: 39) |
| 22 | 983.994 | 4 | 3932.954 | 3932.959 | −1.23 | [SPGSDTYIIFGEAKIEDLTQHAQmSAIENLKPTR] (SEQ ID NO: 38) |

TABLE 1a-continued

Intra- and inter-NAC crosslinks

| Protein 1 | From | To | Peptide 2 | Protein 2 | From | To | Site 1 | Site 2 |
|---|---|---|---|---|---|---|---|---|
| alpha-NAC | 52 | 54 | [VAEAAGLGDHIDK] (SEQ ID NO: 41) | alpha-NAC | 39 | 51 | K3 | K13 |
| alpha-NAC | 39 | 54 | 0 | dead-end | 0 | 0 | K13 | x0 |
| beta-NAC | 70 | 81 | [VQTSVPANTFSVTGSADNK] (SEQ ID NO: 42) | beta-NAC | 82 | 100 | K12 | T3 |
| beta-NAC | 13 | 22 | 0 | dead-end | 0 | 0 | K1 | x0 |
| alpha-NAC | 9 | 13 | {MTGSTETR} (SEQ ID NO: 25) | alpha-NAC | 0 | 8 | K2 | {0 |
| alpha-NAC | 114 | 133 | 0 | dead-end | 0 | 0 | K17 | x0 |
| alpha-NAC | 39 | 57 | 1 | intrapeptidal | 0 | 0 | K13 | K16 |
| beta-NAC | 11 | 22 | 1 | intrapeptidal | 0 | 0 | K2 | K3 |
| alpha-NAC | 114 | 133 | 0 | dead-end | 0 | 0 | K17 | x0 |
| alpha-NAC | 85 | 99 | 0 | dead-end | 0 | 0 | K2 | x0 |
| alpha-NAC | 39 | 54 | 0 | dead-end | 0 | 0 | K16 | x0 |
| alpha-NAC | 69 | 72 | [LANNVTKLGPDGK] (SEQ ID NO: 43) | beta-NAC | 124 | 136 | K4 | K13 |
| alpha-NAC | 80 | 84 | {mTGSTETR} (SEQ ID NO: 25) | alpha-NAC | 0 | 8 | K5 | {0 |
| beta-NAC | 70 | 81 | [VQTSVPANTFSVTGSADNK] (SEQ ID NO: 42) | beta-NAC | 82 | 100 | K12 | T3 |
| beta-NAC | 70 | 100 | 0 | dead-end | 0 | 0 | K12 | x0 |
| alpha-NAC | 84 | 99 | 1 | intrapeptidal | 0 | 0 | K1 | K3 |
| beta-NAC | 23 | 30 | {MTGSTETR} (SEQ ID NO: 25) | alpha-NAC | 0 | 8 | K4 | {0 |
| alpha-NAC | 114 | 133 | 0 | dead-end | 0 | 0 | K17 | x0 |
| alpha-NAC | 114 | 133 | 0 | dead-end | 0 | 0 | K17 | x0 |
| beta-NAC | 131 | 136 | {mMDSKAIAERIK} (SEQ ID NO: 44) | beta-NAC | 0 | 12 | K6 | K12 |
| alpha-NAC | 114 | 133 | 0 | dead-end | 0 | 0 | K17 | x0 |
| beta-NAC | 101 | 123 | 0 | dead-end | 0 | 0 | K23 | x0 |
| beta-NAC | 101 | 123 | 0 | dead-end | 0 | 0 | K22 | x0 |
| beta-NAC | 23 | 30 | [KLQAQQEHVR] (SEQ ID NO: 11) | beta-NAC | 13 | 22 | K4 | K1 |
| alpha-NAC | 73 | 79 | [DDGTVIHFNNPK] (SEQ ID NO: 10) | beta-NAC | 70 | 81 | S6 | K12 |
| beta-NAC | 23 | 30 | {mTGSTETR} (SEQ ID NO: 25) | alpha-NAC | 0 | 8 | K4 | T2 |
| alpha-NAC | 0 | 8 | [QSRSEKKARK] (SEQ ID NO: 45) | alpha-NAC | 55 | 64 | {0 | K6 |
| beta-NAC | 6 | 12 | {mTGSTETRQKEVK} (SEQ ID NO: 27) | alpha-NAC | 0 | 13 | K7 | T2 |
| beta-NAC | 131 | 136 | {mMDSKAIAERIK} (SEQ ID NO: 44) | beta-NAC | 0 | 12 | K6 | K12 |
| alpha-NAC | 0 | 13 | 0 | dead-end | 0 | 0 | T5 | x0 |
| alpha-NAC | 52 | 57 | [DIELVISQANTTR] (SEQ ID NO: 46) | alpha-NAC | 160 | 172 | K3 | T12 |
| alpha-NAC | 52 | 57 | [DIELVISQANTTR] (SEQ ID NO: 46) | alpha-NAC | 160 | 172 | K3 | T12 |
| alpha-NAC | 0 | 8 | [GEDEDVPELVGDFDAASK] (SEQ ID NO: 47) | beta-NAC | 137 | 154 | S4 | K18 |
| beta-NAC | 23 | 26 | [QVTGVSRVCIRKSK] (SEQ ID NO: 48) | alpha-NAC | 73 | 86 | K4 | S6 |
| alpha-NAC | 61 | 63 | [QVTGVSRVCIRKSK] (SEQ ID NO: 48) | alpha-NAC | 73 | 86 | K1 | S6 |
| alpha-NAC | 11 | 13 | [mTGSTETRQK] (SEQ ID NO: 49) | alpha-NAC | 0 | 10 | K3 | T5 |
| alpha-NAC | 58 | 68 | [EADNDIVNAIMSLTM] (SEQ ID NO: 50) | alpha-NAC | 181 | 196 | K11 | T14 |
| alpha-NAC | 55 | 57 | [LFSKLGLK] (SEQ ID NO: 51) | alpha-NAC | 65 | 72 | S2 | K8 |
| alpha-NAC | 0 | 13 | 1 | intrapeptidal | 0 | 0 | {0 | K10 |
| alpha-NAC | 0 | 8 | [mmDSKAIAER] (SEQ ID NO: 39) | beta-NAC | 0 | 10 | S4 | K5 |
| alpha-NAC | 0 | 8 | 0 | dead-end | 0 | 0 | {0 | x0 |
| alpha-NAC | 173 | 177 | 0 | dead-end | 0 | 0 | K2 | x0 |
| alpha-NAC | 0 | 8 | 0 | dead-end | 0 | 0 | {0 | x0 |
| beta-NAC | 23 | 30 | 0 | dead-end | 0 | 0 | K4 | x0 |
| beta-NAC | 23 | 26 | [GTPR] (SEQ ID NO: 52) | beta-NAC | 27 | 30 | K4 | T2 |
| beta-NAC | 23 | 26 | [GTPR] (SEQ ID NO: 52) | beta-NAC | 27 | 30 | K4 | T2 |
| beta-NAC | 123 | 130 | 0 | dead-end | 0 | 0 | K1 | x0 |
| alpha-NAC | 87 | 99 | 0 | dead-end | 0 | 0 | K8 | x0 |
| alpha-NAC | 69 | 79 | 0 | dead-end | 0 | 0 | K4 | x0 |
| beta-NAC | 23 | 30 | [KLQAQQEHVR] (SEQ ID NO: 11) | beta-NAC | 13 | 22 | K4 | K1 |
| alpha-NAC | 87 | 99 | 0 | dead-end | 0 | 0 | K8 | x0 |
| >sp|alpha | 69 | 72 | [QVTGVSR] (SEQ ID NO: 24) | alpha-NAC | 73 | 79 | K4 | T3 |
| alpha-NAC | 64 | 68 | 0 | dead-end | 0 | 0 | K1 | x0 |
| alpha-NAC | 69 | 72 | [QVTGVSR] (SEQ ID NO: 24) | alpha-NAC | 73 | 79 | K4 | T3 |
| alpha-NAC | 52 | 54 | [VAEAAGLGDHIDK] (SEQ ID NO: 41) | alpha-NAC | 39 | 51 | K3 | K13 |
| beta-NAC | 23 | 30 | [KLQAQQEHVR] (SEQ ID NO: 11) | beta-NAC | 13 | 22 | K4 | K1 |
| beta-NAC | 70 | 81 | [VQTSVPANTFSVTGSADNK] (SEQ ID NO: 42) | beta-NAC | 82 | 100 | K12 | T3 |
| alpha-NAC | 64 | 72 | 1 | intrapeptidal | 0 | 0 | K1 | K5 |

TABLE 1a-continued

Intra- and inter-NAC crosslinks

| beta-NAC | 23 | 26 | [GTPR] (SEQ ID NO: 52) | beta-NAC | 27 | 30 | K4 | T2 |
| beta-NAC | 155 | 158 | [NETKADEQ] (SEQ ID NO: 53) | beta-NAC | 155 | 163 | K4 | T3 |
| beta-NAC | 23 | 30 | [KLQAQQEHVR] (SEQ ID NO: 11) | beta-NAC | 13 | 22 | K4 | K1 |
| alpha-NAC | 178 | 180 | [SEKK] (SEQ ID NO: 54) | alpha-NAC | 58 | 61 | K3 | K3 |
| alpha-NAC | 100 | 133 | 0 | dead-end | 0 | 0 | T6 | x0 |
| alpha-NAC | 80 | 84 | [VCIRKSK] (SEQ ID NO: 55) | alpha-NAC | 80 | 86 | K5 | K7 |
| beta-NAC | 0 | 10 | [TAAADDKKLQSNLK] (SEQ ID NO: 56) | beta-NAC | 39 | 52 | {0 | K8 |
| beta-NAC | 33 | 38 | [LGPDGKGEDEDVPELVGDFDAASK] (SEQ ID NO: 57) | beta-NAC | 131 | 154 | K2 | K6 |
| beta-NAC | 0 | 10 | [TAAADDKKLQSNLK] (SEQ ID NO: 56) | beta-NAC | 39 | 52 | {0 | K8 |
| alpha-NAC | 100 | 133 | 0 | dead-end | 0 | 0 | Y7 | x0 |

TABLE 1b

Intramolecular 78Q crosslinks.

| Score | m/z | z | M + H+ | Calculated | Deviation | Peptide 1 |
|---|---|---|---|---|---|---|
| 106 | 561.65 | 3 | 1682.9 | 1682.932 | −2.25 | [LIGEELAQLKEQR] (SEQ ID NO: 58) |
| 61 | 385.21 | 3 | 1153.6 | 1153.621 | 2.17 | [VHKTDLER] (SEQ ID NO: 59) |
| 54 | 799.71 | 3 | 2397.1 | 2397.109 | 0.61 | [NISQDmTQTSGTNLTSEELR] (SEQ ID NO: 60) |
| 42 | 398.23 | 3 | 1192.7 | 1192.672 | −1.01 | [NDLK] (SEQ ID NO: 61) |
| 38 | 385.21 | 3 | 1153.6 | 1153.621 | 2.17 | [VHK] |
| 37 | 396.89 | 3 | 1188.6 | 1188.647 | 0.25 | [NDLKTEGKK} (SEQ ID NO: 62) |
| 30 | 396.89 | 3 | 1188.6 | 1188.647 | −0.25 | [NDLK] (SEQ ID NO: 61) |
| 30 | 794.38 | 3 | 2381.1 | 2381.114 | 3.94 | [NISQDMTQTSGTNLTSEELR] (SEQ ID NO: 60) |
| 27 | 500.62 | 3 | 1499.8 | 1499.848 | −0.92 | [TEGKK} (SEQ ID NO: 63) |
| 25 | 767.06 | 3 | 2299.2 | 2299.165 | 0.86 | [VQQMHRPK] (SEQ ID NO: 105) |
| 22 | 398.23 | 3 | 1192.7 | 1192.672 | 0.1 | [NDLK] (SEQ ID NO: 61) |
| 18 | 379.21 | 3 | 1135.6 | 1135.611 | 2.42 | [VHKTDLER] (SEQ ID NO: 59) |
| 17 | 386.55 | 3 | 1157.6 | 1157.646 | −2.97 | [VHK] |
| 115 | 577.31 | 2 | 1153.6 | 1153.621 | −0.66 | [VHKTDLER] (SEQ ID NO: 59) |
| 91 | 577.31 | 2 | 1153.6 | 1153.621 | −0.66 | [VHK] |
| 83 | 735.83 | 2 | 1470.6 | 1470.642 | 0.38 | [MAEGGVTSEDYR] (SEQ ID NO: 64) |
| 77 | 735.83 | 2 | 1470.6 | 1470.642 | 1.24 | [MAEGGVTSEDYR] (SEQ ID NO: 64) |
| 75 | 841.97 | 2 | 1682.9 | 1682.932 | 0 | [LIGEELAQLKEQR] (SEQ ID NO: 58) |
| 74 | 585.82 | 2 | 1170.6 | 1170.636 | 0.98 | [NDLKTEGKK} (SEQ ID NO: 62) |
| 73 | 667.12 | 4 | 2665.5 | 2665.482 | −4.33 | [VHKTDLER] (SEQ ID NO: 59) |
| 71 | 743.82 | 2 | 1486.6 | 1486.637 | −0.46 | [mAEGGVTSEDYR] (SEQ ID NO: 64) |
| 70 | 573.32 | 4 | 2290.3 | 2290.259 | −0.26 | [VQQmHRPKLIGEELAQLK] (SEQ ID NO: 65) |
| 64 | 585.82 | 2 | 1170.6 | 1170.636 | −1.5 | [NDLKTEGKK} (SEQ ID NO: 62) |
| 62 | 569.32 | 4 | 2274.3 | 2274.264 | 1.02 | [VQQMHRPKLIGEELAQLK] (SEQ ID NO: 65) |
| 50 | 596.84 | 2 | 1192.7 | 1192.672 | −2.71 | [NDLK] (SEQ ID NO: 61) |
| 50 | 667.12 | 4 | 2665.5 | 2665.482 | −4.33 | [TDLER] (SEQ ID NO: 66) |
| 49 | 579.33 | 2 | 1157.6 | 1157.646 | −0.73 | [VHK] |
| 49 | 667.12 | 4 | 2665.5 | 2665.482 | −4.33 | [LIGEELAQLK] (SEQ ID NO: 58) |
| 44 | 666.12 | 4 | 2661.4 | 2661.457 | −3.24 | LIGEELAQLKEQRVHKTDLER (SEQ ID NO: 103) |
| 43 | 666.12 | 4 | 2661.4 | 2661.457 | −3.24 | [TDLER] (SEQ ID NO: 66) |
| 43 | 666.12 | 4 | 2661.4 | 2661.457 | −3.24 | [VHKTDLER] (SEQ ID NO: 59) |
| 42 | 666.12 | 4 | 2661.4 | 2661.457 | −3.24 | [LIGEELAQLK] (SEQ ID NO: 58) |
| 40 | 727.86 | 2 | 1454.7 | 1454.716 | −0.8 | [EAYFEKQQQK] (SEQ ID NO: 71) |

TABLE 1b-continued

Intramolecular 78Q crosslinks.

| | | | | | | | |
|---|---|---|---|---|---|---|---|
| 39 | 729.87 | 2 | 1458.7 | 1458.741 | −3.95 | | [QQQK] (SEQ ID NO: 104) |
| 36 | 743.82 | 2 | 1486.6 | 1486.637 | 1.5 | | [mAEGGVTSEDYR] (SEQ ID NO: 64) |
| 32 | 727.86 | 2 | 1454.7 | 1454.716 | −0.8 | | [QQQK] (SEQ ID NO: 104) |
| 27 | 675.34 | 2 | 1349.7 | 1349.673 | 0.79 | | [AIQLSmQGSSR] (SEQ ID NO: 72) |
| 27 | 667.34 | 2 | 1333.7 | 1333.678 | −1.88 | | [AIQLSMQGSSR] (SEQ ID NO: 72) |
| 22 | 475.51 | 4 | 1899 | 1899.038 | −1.93 | | [KRR] |

| Protein 1 | From | To | Peptide 2 | Protein 2 | From | To | Site 1 | Site 2 |
|---|---|---|---|---|---|---|---|---|
| Atx3 78Q | 208 | 220 | 0 | dead-end | 0 | 0 | K10 | x0 |
| Atx3 78Q | 221 | 228 | 0 | dead-end | 0 | 0 | K3 | x0 |
| Atx3 78Q | 280 | 299 | 0 | dead-end | 0 | 0 | S10 | x0 |
| Atx3 78Q | 434 | 437 | [TEGKK} (SEQ ID NO: 63) | Atx3 78Q | 438 | 443 | K4 | T1 |
| Atx3 78Q | 221 | 223 | [TDLER] (SEQ ID NO: 66) | Atx3 78Q | 224 | 228 | K3 | T1 |
| Atx3 78Q | 434 | 443 | 0 | dead-end | 0 | 0 | K4 | x0 |
| Atx3 78Q | 434 | 437 | [TEGKK} (SEQ ID NO: 63) | Atx3 78Q | 438 | 443 | K4 | T1 |
| Atx3 78Q | 280 | 299 | 0 | dead-end | 0 | 0 | T12 | x0 |
| Atx3 78Q | 438 | 443 | [EQRVHK] (SEQ ID NO: 67) | Atx3 78Q | 218 | 223 | K5 | K6 |
| Atx3 78Q | 200 | 207 | {MTGSTETRQK] (SEQ ID NO: 49) | alpha-NAC | 0 | 10 | K8 | T7 |
| Atx3 78Q | 434 | 437 | [TEGKK} (SEQ ID NO: 63) | Atx3 78Q | 438 | 443 | K4 | K5 |
| Atx3 78Q | 221 | 228 | 1 | intrapeptidal | 0 | 0 | K3 | T4 |
| Atx3 78Q | 221 | 223 | [TDLER] (SEQ ID NO: 66) | Atx3 78Q | 224 | 228 | K3 | T1 |
| Atx3 78Q | 221 | 228 | 0 | dead-end | 0 | 0 | K3 | x0 |
| Atx3 78Q | 221 | 223 | [TDLER] (SEQ ID NO: 66) | Atx3 78Q | 224 | 228 | K3 | T1 |
| Atx3 78Q | 65 | 76 | 0 | dead-end | 0 | 0 | S8 | x0 |
| Atx3 78Q | 65 | 76 | 0 | dead-end | 0 | 0 | Y11 | x0 |
| Atx3 78Q | 208 | 220 | 0 | dead-end | 0 | 0 | K10 | x0 |
| Atx3 78Q | 434 | 443 | 1 | intrapeptidal | 0 | 0 | K4 | K8 |
| Atx3 78Q | 221 | 228 | [LIGEELAQLKEQR] (SEQ ID NO: 58) | Atx3 78Q | 208 | 220 | T4 | K10 |
| Atx3 78Q | 65 | 76 | 0 | dead-end | 0 | 0 | S8 | x0 |
| Atx3 78Q | 200 | 217 | 0 | dead-end | 0 | 0 | K8 | x0 |
| Atx3 78Q | 434 | 443 | 1 | intrapeptidal | 0 | 0 | K8 | T5 |
| Atx3 78Q | 200 | 217 | 0 | dead-end | 0 | 0 | K8 | x0 |
| Atx3 78Q | 434 | 437 | [TEGKK} (SEQ ID NO: 63) | Atx3 78Q | 438 | 443 | K4 | T1 |
| Atx3 78Q | 224 | 228 | LIGEELAQLKEQRVHK (SEQ ID NO: 68) | Atx3 78Q | 208 | 223 | T1 | K16 |
| Atx3 78Q | 221 | 223 | [TDLER] (SEQ ID NO: 66) | Atx3 78Q | 224 | 228 | K3 | T1 |
| Atx3 78Q | 208 | 217 | [EQRVHKTDLER] (SEQ ID NO: 69) | Atx3 78Q | 218 | 228 | K10 | T7 |
| Atx3 78Q | 208 | 228 | 0 | dead-end | 0 | 0 | T17 | x0 |
| Atx3 78Q | 224 | 228 | LIGEELAQLKEQRVHK (SEQ ID NO: 68) | Atx3 78Q | 208 | 223 | T1 | K16 |
| Atx3 78Q | 221 | 228 | [LIGEELAQLKEQR] (SEQ ID NO: 58) | Atx3 78Q | 208 | 220 | T4 | K10 |
| Atx3 78Q | 208 | 217 | [EQRVHKTDLER] (SEQ ID NO: 69) | Atx3 78Q | 218 | 228 | K10 | T7 |
| Atx3 78Q | 303 | 312 | 0 | dead-end | 0 | 0 | K6 | x0 |
| Atx3 78Q | 309 | 312 | [EAYFEK] (SEQ ID NO: 70) | Atx3 78Q | 303 | 308 | K4 | K6 |
| Atx3 78Q | 65 | 76 | 0 | dead-end | 0 | 0 | S8 | x0 |
| Atx3 78Q | 309 | 312 | [EAYFEK] (SEQ ID NO: 70) | Atx3 78Q | 303 | 308 | K4 | K6 |
| Atx3 78Q | 269 | 279 | 0 | dead-end | 0 | 0 | S10 | x0 |
| Atx3 78Q | 269 | 279 | 0 | dead-end | 0 | 0 | S10 | x0 |
| Atx3 78Q | 300 | 302 | [EAYFEKQQQK] (SEQ ID NO: 71) | Atx3 78Q | 303 | 312 | K1 | K6 |

TABLE 1c

Crosslinks identified within NAC-Atx3 78Q complex.

| Score | m/z | z | M + H+ | Calculated | Deviation | Peptide 1 |
|---|---|---|---|---|---|---|
| 45 | 632.035 | 3 | 1894.091 | 1894.084 | 3.54 | [RKKK] (SEQ ID NO: 109) |
| 38 | 1026.208 | 3 | 3076.609 | 3076.594 | 4.83 | [LGLK] (SEQ ID NO: 17) |
| 31 | 1158.192 | 3 | 3472.563 | 3472.554 | 2.37 | [VQQmHRPK] (SEQ ID NO: 105) |
| 25 | 772.085 | 3 | 2314.24 | 2314.245 | −2.09 | [SEKKAR] (SEQ ID NO: 106) |
| 25 | 767.06 | 3 | 2299.167 | 2299.165 | 0.86 | [VQQMHRPK] (SEQ ID NO: 105) |
| 21 | 790.709 | 3 | 2370.111 | 2370.11 | 0.57 | [NETKADEQ} (SEQ ID NO: 53) |
| 15 | 770.747 | 3 | 2310.227 | 2310.22 | 3.02 | [SEKKAR] (SEQ ID NO: 106) |
| 13 | 772.085 | 3 | 2314.241 | 2314.245 | −1.65 | [SEKKAR] (SEQ ID NO: 106) |
| 47 | 1066.949 | 5 | 5330.716 | 5330.718 | −0.39 | [LSVTNIPGIEEVNMIK] (SEQ ID NO: 107) |
| 36 | 777.121 | 4 | 3105.46 | 3105.469 | −2.73 | {MMDSK] (SEQ ID NO: 108) |
| 35 | 777.121 | 4 | 3105.463 | 3105.469 | −1.7 | {MMDSK] (SEQ ID NO: 108) |
| 32 | 539.817 | 2 | 1078.628 | 1078.629 | −1.58 | [EVK] |
| 27 | 667.123 | 4 | 2665.471 | 2665.483 | −4.83 | [IGGKGTPR] (SEQ ID NO: 21) |
| 24 | 1020.487 | 4 | 4078.928 | 4078.946 | −4.37 | [QAKQSR] (SEQ ID NO: 29) |
| 20 | 667.123 | 4 | 2665.471 | 2665.483 | −4.83 | [IGGKGTPRRK] |
| 19 | 791.134 | 4 | 3161.513 | 3161.52 | −2.25 | [IGGKGTPR] (SEQ ID NO: 21) |
| 19 | 837.673 | 4 | 3347.669 | 3347.677 | −2.16 | [QAK] |
| 18 | 837.675 | 4 | 3347.679 | 3347.677 | 0.75 | [QAK] |

| Protein 1 | From | To | Peptide 2 | Protein 2 | From | To | Site 1 | Site 2 |
|---|---|---|---|---|---|---|---|---|
| beta-NAC | 31 | 34 | [AIQLSmQGSSR] (SEQ ID NO: 72) | Atx3 78Q | 269 | 279 | K3 | S5 |
| alpha-NAC | 69 | 72 | [NISQDMTQTSGTNLTSEELRKR] (SEQ ID NO: 73) | Atx3 78Q | 280 | 301 | K4 | S3 |
| Atx3 78Q | 200 | 207 | [TVEEDENEDVEEDSTGIEEK] (SEQ ID NO: 74) | alpha-NAC | 140 | 159 | K8 | K20 |
| alpha-NAC | 58 | 63 | [REAYFEKQQQK] (SEQ ID NO: 75) | Atx3 78Q | 302 | 312 | K3 | K7 |
| Atx3 78Q | 200 | 207 | {MTGSTETRQK] (SEQ ID NO: 49) | alpha-NAC | 0 | 10 | K8 | T7 |
| beta-NAC | 155 | 163 | [EAYFEKQQQK] (SEQ ID NO: 71) | Atx3 78Q | 303 | 312 | K4 | K6 |
| alpha-NAC | 58 | 63 | [REAYFEKQQQK] (SEQ ID NO: 75) | Atx3 78Q | 302 | 312 | K4 | Y4 |
| alpha-NAC | 58 | 63 | [REAYFEKQQQK] (SEQ ID NO: 75) | Atx3 78Q | 302 | 312 | K4 | K11 |
| beta-NAC | 54 | 69 | [NISQDMTQTSGTNLTSEELRKRREAYFEK] (SEQ ID NO: 76) | Atx3 78Q | 280 | 308 | K16 | K29 |
| beta-NAC | 0 | 5 | [NISQDMTQTSGTNLTSEELRK] (SEQ ID NO: 77) | Atx3 78Q | 280 | 300 | {0 | T7 |
| beta-NAC | 0 | 5 | [NISQDMTQTSGTNLTSEELRK] (SEQ ID NO: 77) | Atx3 78Q | 280 | 300 | {0 | S3 |
| alpha-NAC | 11 | 13 | [TEGKK} (SEQ ID NO: 63) | Atx3 78Q | 438 | 443 | K3 | K5 |
| beta-NAC | 23 | 30 | [KRREAYFEKQQQK] (SEQ ID NO: 78) | Atx3 78Q | 300 | 312 | T6 | K1 |
| alpha-NAC | 52 | 57 | {SYYHHHHHHHLENLYFQGMESIFHEK] (SEQ ID NO: 79) | Atx3 78Q | 0 | 25 | K3 | K25 |
| beta-NAC | 23 | 32 | [REAYFEKQQQK] (SEQ ID NO: 75) | Atx3 78Q | 302 | 312 | T6 | K11 |
| beta-NAC | 23 | 30 | [VLEANDGSGMLDEDEEDLQR] (SEQ ID NO: 80) | Atx3 78Q | 229 | 248 | K4 | S8 |
| alpha-NAC | 52 | 54 | [TFLQQPSGNmDDSGFFSIQVISNALK] (SEQ ID NO: 81) | Atx3 78Q | 77 | 102 | K3 | S17 |
| alpha-NAC | 52 | 54 | [TFLQQPSGNmDDSGFFSIQVISNALK] (SEQ ID NO: 82) | Atx3 78Q | 77 | 102 | K3 | S22 |

TABLE 2

Intra- and inter-NAC/Aβ40 crosslinks

| Score | m/z | z | M + H+ | Calculated | Deviation | Peptide 1 |
|---|---|---|---|---|---|---|
| 231 | 756.419 | 2 | 1511.831 | 1511.832 | −0.68 | [LAEALPKQSVDGK] (SEQ ID NO: 83) |
| 175 | 730.889 | 2 | 1460.770 | 1460.767 | 2.48 | [ETIMNQEKLAK] (SEQ ID NO: 84) |
| 169 | 512.315 | 3 | 1534.931 | 1534.918 | 8.75 | [KVVHR] (SEQ ID NO: 85) |
| 169 | 1149.282 | 4 | 4594.107 | 4594.148 | −8.90 | [LAEALPKQSVDGKAPLATGEDDDD EVPDLVENFDEASKNEAN} (SEQ ID NO: 86) |
| 164 | 1156.810 | 4 | 4624.217 | 4624.234 | −3.72 | [LAEALPKQSVDGK] (SEQ ID NO: 83) |
| 161 | 495.954 | 3 | 1485.848 | 1485.850 | −0.84 | [AKQSR] (SEQ ID NO: 87) |
| 159 | 571.341 | 2 | 1141.675 | 1141.676 | −0.75 | [KAMSKLGLR] (SEQ ID NO: 88) |
| 156 | 539.954 | 3 | 1617.848 | 1617.844 | 2.63 | [TATADDK] (SEQ ID NO: 89) |
| 151 | 452.790 | 2 | 904.572 | 904.573 | −0.50 | [KKVVHR] (SEQ ID NO: 90) |
| 151 | 1153.795 | 4 | 4612.157 | 4612.158 | −0.32 | [LAEALPKQSVDGKAPLATGEDDDD EVPDLVENFDEASKNEAN} (SEQ ID NO: 86) |
| 150 | 1156.808 | 4 | 4624.211 | 4624.234 | −4.84 | [LAEALPKQSVDGK] (SEQ ID NO: 83) |
| 148 | 458.268 | 2 | 915.528 | 915.526 | 2.40 | [IGGKGTAR] (SEQ ID NO: 91) |
| 147 | 852.463 | 2 | 1703.919 | 1703.921 | −1.23 | [TATADDKKLQFSLK] (SEQ ID NO: 95) |

TABLE 2-continued

Intra- and inter-NAC/Aβ40 crosslinks

| | | | | | | |
|---|---|---|---|---|---|---|
| 145 | 1092.481 | 3 | 3275.428 | 3275.423 | 1.27 | [APLATGEDDDDEVPDLVENFDEASK NEAN} (SEQ ID NO: 92) |
| 140 | 503.259 | 2 | 1005.511 | 1005.510 | 1.43 | [TATADDKK] (SEQ ID NO: 94) |
| 136 | 559.643 | 3 | 1676.914 | 1676.918 | −2.10 | (IGGKGTAR) (SEQ ID NO: 91) |

| Protein 1 | From | To | Peptide 2 | Protein 2 | From | To | Site 1 | Site 2 |
|---|---|---|---|---|---|---|---|---|
| beta-NAC | 121 | 133 | 0 | dead-end | 0 | 0 | K7 | x0 |
| beta-NAC | 3 | 13 | 0 | dead-end | 0 | 0 | K8 | x0 |
| beta-NAC | 31 | 35 | [IGGKGTAR] (SEQ ID NO: 91) | beta-NAC | 20 | 27 | K1 | K4 |
| beta-NAC | 121 | 163 | 1 | intrapeptidal | 0 | 0 | K7 | K13 |
| beta-NAC | 121 | 133 | [APLATGEDDDDEVPDLV ENFDEASKNEAN} (SEQ ID NO: 92) | beta-NAC | 134 | 163 | K7 | T5 |
| alpha-NAC | 67 | 71 | [IGGKGTAR] (SEQ ID NO: 91) | beta-NAC | 20 | 27 | K2 | K4 |
| alpha-NAC | 78 | 86 | 1 | intrapeptidal | 0 | 0 | K5 | S4 |
| beta-NAC | 36 | 42 | [IGGKGTAR] (SEQ ID NO: 91) | beta-NAC | 20 | 27 | T1 | K4 |
| beta-NAC | 30 | 35 | 1 | intrapeptidal | 0 | 0 | K1 | K2 |
| beta-NAC | 121 | 163 | 0 | dead-end | 0 | 0 | K13 | x0 |
| beta-NAC | 121 | 133 | [APLATGEDDDDEVPDLV ENFDEASKNEAN} (SEQ ID NO: 92) | beta-NAC | 134 | 163 | K7 | T5 |
| beta-NAC | 20 | 27 | 0 | dead-end | 0 | 0 | K4 | x0 |
| beta-NAC | 36 | 49 | 1 | intrapeptidal | 0 | 0 | K7 | K8 |
| beta-NAC | 134 | 163 | 0 | dead-end | 0 | 0 | S24 | x0 |
| beta-NAC | 36 | 43 | 0 | dead-end | 0 | 0 | K7 | x0 |
| beta-NAC | 20 | 27 | {MDAEFR] (SEQ ID NO: 93) | Abeta40 | 0 | 6 | K4 | {0 |
| 135 | 677.733 | 3 | 2031.186 | 2031.189 | −1.59 | [KSKNILFVITKPDVYK] (SEQ ID NO: 96) |
| 134 | 499.607 | 3 | 1496.807 | 1496.807 | −0.07 | [KVVHR] (SEQ ID NO: 85) |
| 134 | 397.748 | 2 | 794.489 | 794.488 | 0.59 | [KVVHR] (SEQ ID NO: 85) |
| 133 | 462.710 | 2 | 924.413 | 924.413 | −0.35 | {MDAEFR] (SEQ ID NO: 93) |
| 132 | 502.942 | 3 | 1506.812 | 1506.812 | −0.26 | [AKQSR] (SEQ ID NO: 87) |
| 131 | 512.311 | 3 | 1534.919 | 1534.918 | 0.62 | [KVVHR] (SEQ ID NO: 85) |
| 124 | 566.839 | 4 | 2264.333 | 2264.336 | −1.42 | (IGGKGTAR) (SEQ ID NO: 91) |
| 123 | 510.309 | 2 | 1019.611 | 1019.614 | −2.62 | [KLQFSLK] (SEQ ID NO: 97) |
| 117 | 543.977 | 3 | 1629.917 | 1629.920 | −1.54 | [TATADDK] (SEQ ID NO: 89) |
| 113 | 555.619 | 3 | 1664.842 | 1664.842 | −0.08 | (IGGKGTAR) (SEQ ID NO: 91) |
| 112 | 563.821 | 4 | 2252.263 | 2252.261 | 0.93 | (IGGKGTAR) (SEQ ID NO: 91) |
| 111 | 503.630 | 3 | 1508.877 | 1508.882 | −3.58 | [KVVHR] (SEQ ID NO: 85) |
| 111 | 470.707 | 2 | 940.406 | 940.408 | −1.74 | {mDAEFR] (SEQ ID NO: 93) |
| 108 | 579.340 | 2 | 1157.672 | 1157.671 | 0.55 | [KAmSKLGLR] (SEQ ID NO: 88) |
| 100 | 582.651 | 3 | 1745.937 | 1745.939 | −1.29 | (IGGKGTAR) (SEQ ID NO: 91) |
| 98 | 384.484 | 4 | 1534.913 | 1534.918 | −3.19 | [KVVHR] (SEQ ID NO: 85) |
| 96 | 406.979 | 4 | 1624.893 | 1624.902 | −5.12 | [KVVHR] (SEQ ID NO: 85) |
| 96 | 499.980 | 3 | 1497.926 | 1497.925 | 0.87 | [AKQSR] (SEQ ID NO: 87) |
| 93 | 586.676 | 3 | 1758.014 | 1758.015 | −0.10 | (IGGKGTAR) (SEQ ID NO: 91) |
| 93 | 350.721 | 2 | 700.434 | 700.435 | −1.97 | [AKAVR] (SEQ ID NO: 98) |
| alpha-NAC | 98 | 113 | 1 | intrapeptidal | 0 | 0 | K1 | K3 |
| beta-NAC | 31 | 35 | [TATADDK] (SEQ ID NO: 89) | beta-NAC | 36 | 42 | K1 | T1 |
| beta-NAC | 31 | 35 | 0 | dead-end | 0 | 0 | K1 | x0 |
| Abeta40 | 0 | 6 | 0 | dead-end | 0 | 0 | {0 | x0 |
| alpha-NAC | 67 | 71 | {MDAEFR] (SEQ ID NO: 93) | Abeta40 | 0 | 6 | K2 | {0 |
| beta-NAC | 31 | 35 | [IGGKGTAR] (SEQ ID NO: 91) | beta-NAC | 20 | 27 | K1 | K4 |
| beta-NAC | 20 | 27 | [LAEALPKQSVDGK] (SEQ ID NO: 83) | beta-NAC | 121 | 133 | K4 | K7 |
| beta-NAC | 43 | 49 | 0 | dead-end | 0 | 0 | K1 | x0 |
| beta-NAC | 36 | 42 | [IGGKGTAR] (SEQ ID NO: 91) | beta-NAC | 20 | 27 | T1 | K4 |
| beta-NAC | 20 | 27 | {MDAEFR] (SEQ ID NO: 93) | Abeta40 | 0 | 6 | K4 | {0 |
| beta-NAC | 20 | 27 | [LAEALPKQSVDGK] (SEQ ID NO: 83) | beta-NAC | 121 | 133 | K4 | K7 |
| beta-NAC | 31 | 35 | [TATADDK] (SEQ ID NO: 89) | beta-NAC | 36 | 42 | K1 | T1 |
| Abeta40 | 0 | 6 | 0 | dead-end | 0 | 0 | {0 | x0 |
| alpha-NAC | 78 | 86 | 1 | intrapeptidal | 0 | 0 | K5 | S4 |
| beta-NAC | 20 | 27 | [TATADDKK] (SEQ ID NO: 94) | beta-NAC | 36 | 43 | K4 | K7 |
| beta-NAC | 31 | 35 | [IGGKGTAR] (SEQ ID NO: 91) | beta-NAC | 20 | 27 | K1 | K4 |

TABLE 2-continued

Intra- and inter-NAC/Aβ40 crosslinks

| | | | | | | | | |
|---|---|---|---|---|---|---|---|---|
| beta-NAC | 31 | 35 | [TATADDKK] (SEQ ID NO: 94) | beta-NAC | 36 | 43 | K1 | T1 |
| alpha-NAC | 67 | 71 | [IGGKGTAR] (SEQ ID NO: 91) | beta-NAC | 20 | 27 | K2 | K4 |
| beta-NAC | 20 | 27 | [TATADDKK] (SEQ ID NO: 94) | beta-NAC | 36 | 43 | K4 | K7 |
| alpha-NAC | 193 | 197 | 0 | dead-end | 0 | 0 | K2 | x0 |
| 91 | 578.672 | 3 | 1734.001 | 1734.007 | −3.49 | [LQFSLK] (SEQ ID NO: 99) | | |
| 91 | 574.651 | 3 | 1721.938 | 1721.932 | 3.64 | [TATADDK] (SEQ ID NO: 89) | | |
| 88 | 449.262 | 2 | 897.517 | 897.515 | 2.32 | [IGGKGTAR] (SEQ ID NO: 91) | | |
| 73 | 360.702 | 2 | 720.397 | 720.396 | 0.95 | [KAMSK] (SEQ ID NO: 101) | | |
| 71 | 542.304 | 3 | 1624.898 | 1624.902 | −2.13 | [KVVHR] (SEQ ID NO: 85) | | |
| 70 | 544.656 | 3 | 1631.954 | 1631.948 | 3.52 | [LQFSLK] (SEQ ID NO: 99) | | |
| 66 | 861.468 | 2 | 1721.929 | 1721.932 | −1.67 | [LQFSLK] (SEQ ID NO: 99) | | |
| 57 | 554.072 | 4 | 2213.267 | 2213.271 | −1.76 | [IGGKGTAR] (SEQ ID NO: 91) | | |
| 51 | 820.919 | 2 | 1640.830 | 1640.835 | −3.01 | [LQFSLK] (SEQ ID NO: 99) | | |
| 42 | 446.264 | 2 | 891.521 | 891.519 | 3.15 | [LQFSLK] (SEQ ID NO: 99) | | |
| 69 | 384.485 | 4 | 1534.917 | 1534.918 | −0.32 | [KVVHR] (SEQ ID NO: 85) | | |
| 117 | 543.979 | 3 | 1629.923 | 1629.920 | 2.23 | [TATADDK] (SEQ ID NO: 89) | | |
| 68 | 563.821 | 4 | 2252.261 | 2252.261 | −0.13 | [IGGKGTAR] (SEQ ID NO: 91) | | |
| 82 | 559.643 | 3 | 1676.913 | 1676.918 | −2.64 | [IGGKGTAR] (SEQ ID NO: 91) | | |
| 112 | 555.622 | 3 | 1664.851 | 1664.842 | 4.98 | [IGGKGTAR] (SEQ ID NO: 91) | | |
| 80 | 1049.776 | 4 | 4196.082 | 4196.068 | 3.33 | [LAEALPKQSVDGK] (SEQ ID NO: 83) | | |
| beta-NAC | 44 | 49 | [TATADDKK] (SEQ ID NO: 94) | beta-NAC | 36 | 43 | S4 | K7 |
| beta-NAC | 36 | 42 | [LQFSLKK] (SEQ ID NO: 100) | beta-NAC | 44 | 50 | T3 | K6 |
| beta-NAC | 20 | 27 | 1 | intrapeptidal | 0 | 0 | K4 | T6 |
| alpha-NAC | 78 | 82 | 0 | dead-end | 0 | 0 | K1 | x0 |
| beta-NAC | 31 | 35 | [TATADDKK] (SEQ ID NO: 94) | beta-NAC | 36 | 43 | K1 | K7 |
| beta-NAC | 44 | 49 | [IGGKGTAR] (SEQ ID NO: 91) | beta-NAC | 20 | 27 | S4 | K4 |
| beta-NAC | 44 | 49 | [TATADDKK] (SEQ ID NO: 94) | beta-NAC | 36 | 43 | S4 | K7 |
| beta-NAC | 20 | 27 | [ETIMNQEKLAK] (SEQ ID NO: 84) | beta-NAC | 3 | 13 | K4 | K8 |
| beta-NAC | 44 | 49 | {MDAEFR} (SEQ ID NO: 93) | Abeta40 | 0 | 6 | S4 | {0 |
| beta-NAC | 44 | 49 | 0 | dead-end | 0 | 0 | S4 | x0 |
| beta-NAC | 31 | 35 | [IGGKGTAR] (SEQ ID NO: 91) | beta-NAC | 20 | 27 | K1 | K4 |
| beta-NAC | 36 | 42 | [IGGKGTAR] (SEQ ID NO: 91) | beta-NAC | 20 | 27 | T1 | K4 |
| beta-NAC | 20 | 27 | [LAEALPKQSVDGK] (SEQ ID NO: 83) | beta-NAC | 121 | 133 | K4 | K7 |
| beta-NAC | 20 | 27 | {MDAEFR} (SEQ ID NO: 93) | Abeta40 | 0 | 6 | K4 | {0 |
| beta-NAC | 20 | 27 | {MDAEFR} (SEQ ID NO: 93) | Abeta40 | 0 | 6 | K4 | {0 |
| beta-NAC | 121 | 133 | [APLATGEDDDDEVPDLVENFDEASK] (SEQ ID NO: 102) | beta-NAC | 134 | 158 | K7 | T5 |

TABLE 3

*C. elegans* strains.

| | |
|---|---|
| DEU117 | rmIs132 [unc-54p::Q35::YFP]; gamEx17 [myo-3p::empty::unc-54 3'UTR (50 ng/μl), myo-2p::mCherry::unc-54 3'UTR (2.5 ng/μl), DNA ladder (100 ng/μl)] |
| DEU118 | rmIs132 [unc-54p::Q35::YFP]; gamEx18 [myo-3p::3xFLAG::αNAC::unc-54 3'UTR (25 ng/μl), myo-3p::3xFLAG::βNAC::unc-54 3'UTR (25 ng/μl), myo-2p::mCherry::unc-54 3'UTR (2.5 ng/μl), DNA ladder (100 ng/μl)] |
| DEU119 | rmIs132 [unc-54p::Q35::YFP]; gamEx19 [myo-3p::3xFLAG::ΔUBA-αNAC::unc-54 3'UTR (25 ng/μl), myo-3p::3xFLAG::βNAC::unc-54 3'UTR (25 ng/μl), myo-2p::mCherry::unc-54 3'UTR (2.5 ng/μl), DNA ladder (100 ng/μl)] |
| DEU120 | rmIs132 [unc-54p::Q35::YFP]; gamEx20 [myo-3p::3xFLAG::αNAC::unc-54 3'UTR (25 ng/μl), myo-3p::3xFLAG::RRK/AAA-βNAC::unc-54 3'UTR (25 ng/μl), myo-2p::mCherry::unc-54 3'UTR (2.5 ng/μl), DNA ladder (100 ng/μl)] |
| DEU121 | rmIs132 [unc-54p::Q35::YFP]; gamEx21 [myo-3p::3xFLAG::αNAC::unc-54 3'UTR (25 ng/μl), myo-3p::3xFLAG::ΔNβ-NAC::unc-54 3'UTR (25 ng/μl), myo-2p::mCherry::unc-54 3'UTR (2.5 ng/μl), DNA ladder (100 ng/μl)] |
| DEU122 | marIs135 [unc-54p::FlucDM::EGFP]; gamEx22 [myo-3p::empty::unc-54 3'UTR (50 ng/μl), myo-2p::mCherry::unc-54 3-UTR (2.5 ng/μl), DNA ladder (50 ng/μl)] |
| DEU123 | marIs135 [unc-54p::FlucDM::EGFP]; gamEx23 [myo-3p::3xFLAG::αNAC::unc-43 3'UTR (25 ng/μl), myo-3p::3xFLAG::βNAC::unc-54 3'UTR (25 ng/μl), myo-2p::mCherry::unc-54 3'UTR (2.5 ng/μl), DNA ladder (50 ng/μl)] |
| DEU124 | marIs135 [unc-54p::FlucDM::EGFP]; gamEx24 [myo-3p::3xFLAG::αNAC::unc-54 3'UTR (25 ng/μl), myo-3p::3xFLAG::ΔNβ-NAC::unc-54 3'UTR (25 ng/μl), myo-2p::mCherry::unc-54 3'UTR (2.5 ng/μl), DNA ladder (50 ng/μl)] |

What is claimed is:

1. An isolated peptide consisting of an amino acid sequence selected from the group consisting of SEQ ID NO:1 and SEQ ID NO:2, or a sequence having at least 90% identity to an amino acid sequence selected from the group consisting of SEQ ID NO:1 and SEQ ID NO:2, wherein the isolated peptide suppresses aggregation of a protein comprising a polyglutamine (polyQ) sequence.

2. The isolated peptide of claim 1, wherein the protein comprising the polyQ sequence is polyQ-expanded huntingtin exon1 or Ataxin-3.

3. A fusion protein comprising a peptide comprising an amino acid sequence selected from the group consisting of SEQ ID NOS:1-3 connected to a peptide comprising an apical domain of chaperonin containing TCP1 subunit 1 (CCT1).

4. The fusion protein of claim 3, wherein the apical domain of CCT1 comprises an amino acid sequence of SEQ ID NO:7, or a sequence having at least 90% identity to the amino acid sequence of SEQ ID NO:7, wherein the fusion protein suppresses aggregation of a protein comprising a polyQ sequence.

5. The fusion protein of claim 3, wherein the fusion protein comprises an amino acid sequence of SEQ ID NO:8, or a sequence having at least 90% identity to the sequence of SEQ ID NO:8, wherein the fusion protein suppresses aggregation of a protein comprising a polyQ sequence.

6. The fusion protein of claim 3, further comprising a cell-penetrating peptide.

7. A composition comprising the fusion protein of claim 3 and a pharmaceutically acceptable excipient.

8. A method of suppressing aggregation of a protein comprising a polyglutamine (PolyQ) sequence in a subject, the method comprising administering a therapeutically effective amount of the composition of claim 7 to the subject.

9. The method of claim 8, wherein the protein comprising the PolyQ sequence is polyQ-expanded huntingtin exon1 or Ataxin-3.

* * * * *

SEQUENCE LISTING

<160> NUMBER OF SEQ ID NOS: 109

<210> SEQ ID NO 1
<211> LENGTH: 40
<212> TYPE: PRT
<213> ORGANISM: Caenorhabditis elegans

<400> SEQUENCE: 1

Met Asp Ser Lys Ala Ile Ala Glu Arg Ile Lys Lys Leu Gln Ala Gln
1               5                   10                  15

Gln Glu His Val Arg Ile Gly Gly Lys Gly Thr Pro Arg Arg Lys Lys
            20                  25                  30

Lys Val Ile His Lys Thr Ala Ala
        35                  40

<210> SEQ ID NO 2
<211> LENGTH: 38
<212> TYPE: PRT
<213> ORGANISM: Homo sapiens

<400> SEQUENCE: 2

Met Lys Glu Thr Ile Met Asn Gln Glu Lys Leu Ala Lys Leu Gln Ala
1               5                   10                  15

Gln Val Arg Ile Gly Gly Lys Gly Thr Ala Arg Arg Lys Lys Lys Val
            20                  25                  30

Val His Arg Thr Ala Thr
        35

<210> SEQ ID NO 3
<211> LENGTH: 16
<212> TYPE: PRT
<213> ORGANISM: Homo sapiens

<400> SEQUENCE: 3

Lys Gly Thr Ala Arg Arg Lys Lys Lys Val Val His Arg Thr Ala Thr
1               5                   10                  15

<210> SEQ ID NO 4
<211> LENGTH: 72
<212> TYPE: PRT
<213> ORGANISM: Homo sapiens

<400> SEQUENCE: 4

Met Pro Gly Glu Ala Thr Glu Thr Val Pro Ala Thr Glu Gln Glu Leu
1               5                   10                  15

Pro Gln Pro Gln Ala Glu Thr Gly Ser Gly Thr Glu Ser Asp Ser Asp
            20                  25                  30

Glu Ser Val Pro Glu Leu Glu Glu Gln Asp Ser Thr Gln Ala Thr Thr
        35                  40                  45

Gln Gln Ala Gln Leu Ala Ala Ala Glu Ile Asp Glu Glu Pro Val
    50                  55                  60

Ser Lys Ala Lys Gln Ser Arg Ser
65                  70

<210> SEQ ID NO 5
<211> LENGTH: 401
<212> TYPE: PRT
<213> ORGANISM: Homo sapiens
<300> PUBLICATION INFORMATION:
<308> DATABASE ACCESSION NUMBER: NCBI/NP_001008897
<309> DATABASE ENTRY DATE: 2019-02-03
<313> RELEVANT RESIDUES IN SEQ ID NO: (1)..(401)

<400> SEQUENCE: 5

```
Met Ser Ser Lys Ile Ile Gly Ile Asn Gly Asp Phe Phe Ala Asn Met
1               5                   10                  15

Val Val Asp Ala Val Leu Ala Ile Lys Tyr Thr Asp Ile Arg Gly Gln
            20                  25                  30

Pro Arg Tyr Pro Val Asn Ser Val Asn Ile Leu Lys Ala His Gly Arg
            35                  40                  45

Ser Gln Met Glu Ser Met Leu Ile Ser Gly Tyr Ala Leu Asn Cys Val
    50                  55                  60

Val Gly Ser Gln Gly Met Pro Lys Arg Ile Val Asn Ala Lys Ile Ala
65                  70                  75                  80

Cys Leu Asp Phe Ser Leu Gln Lys Thr Lys Met Lys Leu Gly Val Gln
                85                  90                  95

Val Val Ile Thr Asp Pro Glu Lys Leu Asp Gln Ile Arg Gln Arg Glu
            100                 105                 110

Ser Asp Ile Thr Lys Glu Arg Ile Gln Lys Ile Leu Ala Thr Gly Ala
            115                 120                 125

Asn Val Ile Leu Thr Thr Gly Gly Ile Asp Asp Met Cys Leu Lys Tyr
130                 135                 140

Phe Val Glu Ala Gly Ala Met Ala Val Arg Arg Val Leu Lys Arg Asp
145                 150                 155                 160

Leu Lys Arg Ile Ala Lys Ala Ser Gly Ala Thr Ile Leu Ser Thr Leu
                165                 170                 175

Ala Asn Leu Glu Gly Glu Glu Thr Phe Glu Ala Ala Met Leu Gly Gln
            180                 185                 190

Ala Glu Glu Val Val Gln Glu Arg Ile Cys Asp Asp Glu Leu Ile Leu
            195                 200                 205

Ile Lys Asn Thr Lys Ala Arg Thr Ser Ala Ser Ile Ile Leu Arg Gly
            210                 215                 220

Ala Asn Asp Phe Met Cys Asp Glu Met Glu Arg Ser Leu His Asp Ala
225                 230                 235                 240

Leu Cys Val Val Lys Arg Val Leu Glu Ser Lys Ser Val Val Pro Gly
                245                 250                 255

Gly Gly Ala Val Glu Ala Ala Leu Ser Ile Tyr Leu Glu Asn Tyr Ala
            260                 265                 270

Thr Ser Met Gly Ser Arg Glu Gln Leu Ala Ile Ala Glu Phe Ala Arg
            275                 280                 285

Ser Leu Leu Val Ile Pro Asn Thr Leu Ala Val Asn Ala Ala Gln Asp
    290                 295                 300

Ser Thr Asp Leu Val Ala Lys Leu Arg Ala Phe His Asn Glu Ala Gln
305                 310                 315                 320

Val Asn Pro Glu Arg Lys Asn Leu Lys Trp Ile Gly Leu Asp Leu Ser
                325                 330                 335

Asn Gly Lys Pro Arg Asp Asn Lys Gln Ala Gly Val Phe Glu Pro Thr
            340                 345                 350

Ile Val Lys Val Lys Ser Leu Lys Phe Ala Thr Glu Ala Ala Ile Thr
            355                 360                 365

Ile Leu Arg Ile Asp Asp Leu Ile Lys Leu His Pro Glu Ser Lys Asp
            370                 375                 380

Asp Lys His Gly Ser Tyr Glu Asp Ala Val His Ser Gly Ala Leu Asn
385                 390                 395                 400

Asp
```

```
<210> SEQ ID NO 6
<211> LENGTH: 556
<212> TYPE: PRT
<213> ORGANISM: Homo sapiens
<300> PUBLICATION INFORMATION:
<308> DATABASE ACCESSION NUMBER: NCBI/NP_110379
<309> DATABASE ENTRY DATE: 2019-02-03
<313> RELEVANT RESIDUES IN SEQ ID NO: (1)..(556)

<400> SEQUENCE: 6

Met Glu Gly Pro Leu Ser Val Phe Gly Asp Arg Ser Thr Gly Glu Thr
1               5                   10                  15

Ile Arg Ser Gln Asn Val Met Ala Ala Ser Ile Ala Asn Ile Val
            20                  25                  30

Lys Ser Ser Leu Gly Pro Val Gly Leu Asp Lys Met Leu Val Asp Asp
        35                  40                  45

Ile Gly Asp Val Thr Ile Thr Asn Asp Gly Ala Thr Ile Leu Lys Leu
    50                  55                  60

Leu Glu Val Glu His Pro Ala Ala Lys Val Leu Cys Glu Leu Ala Asp
65                  70                  75                  80

Leu Gln Asp Lys Glu Val Gly Asp Gly Thr Thr Ser Val Ile Ile
                85                  90                  95

Ala Ala Glu Leu Leu Lys Asn Ala Asp Glu Leu Val Lys Gln Lys Ile
            100                 105                 110

His Pro Thr Ser Val Ile Ser Gly Tyr Arg Leu Ala Cys Lys Glu Ala
        115                 120                 125

Val Arg Tyr Ile Asn Glu Asn Leu Ile Val Asn Thr Asp Glu Leu Gly
    130                 135                 140

Arg Asp Cys Leu Ile Asn Ala Ala Lys Thr Ser Met Ser Ser Lys Ile
145                 150                 155                 160

Ile Gly Ile Asn Gly Asp Phe Phe Ala Asn Met Val Val Asp Ala Val
                165                 170                 175

Leu Ala Ile Lys Tyr Thr Asp Ile Arg Gly Gln Pro Arg Tyr Pro Val
            180                 185                 190

Asn Ser Val Asn Ile Leu Lys Ala His Gly Arg Ser Gln Met Glu Ser
        195                 200                 205

Met Leu Ile Ser Gly Tyr Ala Leu Asn Cys Val Val Gly Ser Gln Gly
    210                 215                 220

Met Pro Lys Arg Ile Val Asn Ala Lys Ile Ala Cys Leu Asp Phe Ser
225                 230                 235                 240

Leu Gln Lys Thr Lys Met Lys Leu Gly Val Gln Val Ile Thr Asp
                245                 250                 255

Pro Glu Lys Leu Asp Gln Ile Arg Gln Arg Glu Ser Asp Ile Thr Lys
            260                 265                 270

Glu Arg Ile Gln Lys Ile Leu Ala Thr Gly Ala Asn Val Ile Leu Thr
        275                 280                 285

Thr Gly Gly Ile Asp Asp Met Cys Leu Lys Tyr Phe Val Glu Ala Gly
    290                 295                 300

Ala Met Ala Val Arg Arg Val Leu Lys Arg Asp Leu Lys Arg Ile Ala
305                 310                 315                 320

Lys Ala Ser Gly Ala Thr Ile Leu Ser Thr Leu Ala Asn Leu Glu Gly
                325                 330                 335

Glu Glu Thr Phe Glu Ala Ala Met Leu Gly Gln Ala Glu Glu Val Val
            340                 345                 350
```

```
Gln Glu Arg Ile Cys Asp Asp Glu Leu Ile Leu Ile Lys Asn Thr Lys
            355                 360                 365

Ala Arg Thr Ser Ala Ser Ile Ile Leu Arg Gly Ala Asn Asp Phe Met
370                 375                 380

Cys Asp Glu Met Glu Arg Ser Leu His Asp Ala Leu Cys Val Val Lys
385                 390                 395                 400

Arg Val Leu Glu Ser Lys Ser Val Pro Gly Gly Ala Val Glu
            405                 410                 415

Ala Ala Leu Ser Ile Tyr Leu Glu Asn Tyr Ala Thr Ser Met Gly Ser
            420                 425                 430

Arg Glu Gln Leu Ala Ile Ala Glu Phe Ala Arg Ser Leu Leu Val Ile
            435                 440                 445

Pro Asn Thr Leu Ala Val Asn Ala Ala Gln Asp Ser Thr Asp Leu Val
            450                 455                 460

Ala Lys Leu Arg Ala Phe His Asn Glu Ala Gln Val Asn Pro Glu Arg
465                 470                 475                 480

Lys Asn Leu Lys Trp Ile Gly Leu Asp Leu Ser Asn Gly Lys Pro Arg
                485                 490                 495

Asp Asn Lys Gln Ala Gly Val Phe Glu Pro Thr Ile Val Lys Val Lys
            500                 505                 510

Ser Leu Lys Phe Ala Thr Glu Ala Ala Ile Thr Ile Leu Arg Ile Asp
            515                 520                 525

Asp Leu Ile Lys Leu His Pro Glu Ser Lys Asp Asp Lys His Gly Ser
            530                 535                 540

Tyr Glu Asp Ala Val His Ser Gly Ala Leu Asn Asp
545                 550                 555

<210> SEQ ID NO 7
<211> LENGTH: 175
<212> TYPE: PRT
<213> ORGANISM: Artificial Sequence
<220> FEATURE:
<223> OTHER INFORMATION: Apical domain of CTT1

<400> SEQUENCE: 7

Met Val Pro Gly Tyr Ala Leu Asn Cys Thr Val Ala Ser Gln Ala Met
1               5                   10                  15

Pro Lys Arg Ile Ala Gly Gly Asn Val Lys Ile Ala Cys Leu Asp Leu
            20                  25                  30

Asn Leu Gln Lys Ala Arg Met Ala Met Gly Val Gln Ile Asn Ile Asp
        35                  40                  45

Asp Pro Glu Gln Leu Glu Gln Ile Arg Lys Arg Glu Ala Gly Ile Val
    50                  55                  60

Leu Glu Arg Val Lys Lys Ile Ile Asp Ala Gly Ala Gln Val Val Leu
65                  70                  75                  80

Thr Thr Lys Gly Ile Asp Asp Leu Cys Leu Lys Glu Phe Val Glu Ala
                85                  90                  95

Lys Ile Met Gly Val Arg Arg Cys Lys Lys Glu Asp Leu Arg Arg Ile
            100                 105                 110

Ala Arg Ala Thr Gly Ala Thr Leu Val Ser Ser Met Ser Asn Leu Glu
        115                 120                 125

Gly Glu Glu Thr Phe Glu Ser Ser Tyr Leu Gly Leu Cys Asp Glu Val
    130                 135                 140

Val Gln Ala Lys Phe Ser Asp Asp Glu Cys Ile Leu Ile Lys Gly Thr
145                 150                 155                 160
```

Ser Lys Ala Ala Ala Ala Leu Glu His His His His His His
            165                 170                 175

<210> SEQ ID NO 8
<211> LENGTH: 214
<212> TYPE: PRT
<213> ORGANISM: Artificial Sequence
<220> FEATURE:
<223> OTHER INFORMATION: ApiCCT1-N-terminal beta NAC fusion protein

<400> SEQUENCE: 8

Met Gly Val Pro Gly Tyr Ala Leu Asn Cys Thr Val Ala Ser Gln Ala
1               5                   10                  15

Met Pro Lys Arg Ile Ala Gly Gly Asn Val Lys Ile Ala Cys Leu Asp
            20                  25                  30

Leu Asn Leu Gln Lys Ala Arg Met Ala Met Gly Val Gln Ile Asn Ile
        35                  40                  45

Asp Asp Pro Glu Gln Leu Glu Gln Ile Arg Lys Arg Glu Ala Gly Ile
    50                  55                  60

Val Leu Glu Arg Val Lys Lys Ile Ile Asp Ala Gly Ala Gln Val Val
65                  70                  75                  80

Leu Thr Thr Lys Gly Ile Asp Asp Leu Cys Leu Lys Glu Phe Val Glu
                85                  90                  95

Ala Lys Ile Met Gly Val Arg Arg Cys Lys Lys Glu Asp Leu Arg Arg
            100                 105                 110

Ile Ala Arg Ala Thr Gly Ala Thr Leu Val Ser Ser Met Ser Asn Leu
        115                 120                 125

Glu Gly Glu Glu Thr Phe Glu Ser Ser Tyr Leu Gly Leu Cys Asp Glu
    130                 135                 140

Val Val Gln Ala Lys Phe Ser Asp Asp Glu Cys Ile Leu Ile Lys Gly
145                 150                 155                 160

Thr Ser Lys Ala Ala Ala Ala Leu Glu Gly Gly Ser Gly Gly Ser
                165                 170                 175

Met Lys Glu Thr Ile Met Asn Gln Glu Lys Leu Ala Lys Leu Gln Ala
            180                 185                 190

Gln Val Arg Ile Gly Gly Lys Gly Thr Ala Arg Arg Lys Lys Lys Val
        195                 200                 205

Val His Arg Thr Ala Thr
    210

<210> SEQ ID NO 9
<211> LENGTH: 16
<212> TYPE: PRT
<213> ORGANISM: Homo sapiens

<400> SEQUENCE: 9

Val Ala Glu Ala Ala Gly Leu Gly Asp His Ile Asp Lys Gln Ala Lys
1               5                   10                  15

<210> SEQ ID NO 10
<211> LENGTH: 12
<212> TYPE: PRT
<213> ORGANISM: Homo sapiens

<400> SEQUENCE: 10

Asp Asp Gly Thr Val Ile His Phe Asn Asn Pro Lys
1               5                   10

<210> SEQ ID NO 11

```
<211> LENGTH: 10
<212> TYPE: PRT
<213> ORGANISM: Homo sapiens

<400> SEQUENCE: 11

Lys Leu Gln Ala Gln Gln Glu His Val Arg
1               5                   10

<210> SEQ ID NO 12
<211> LENGTH: 5
<212> TYPE: PRT
<213> ORGANISM: Homo sapiens

<400> SEQUENCE: 12

Gln Lys Glu Val Lys
1               5

<210> SEQ ID NO 13
<211> LENGTH: 20
<212> TYPE: PRT
<213> ORGANISM: Homo sapiens

<400> SEQUENCE: 13

Ile Glu Asp Leu Thr Gln His Ala Gln Met Ser Ala Ile Glu Asn Leu
1               5                   10                  15

Lys Pro Thr Arg
            20

<210> SEQ ID NO 14
<211> LENGTH: 19
<212> TYPE: PRT
<213> ORGANISM: Homo sapiens

<400> SEQUENCE: 14

Val Ala Glu Ala Ala Gly Leu Gly Asp His Ile Asp Lys Gln Ala Lys
1               5                   10                  15

Gln Ser Arg

<210> SEQ ID NO 15
<211> LENGTH: 12
<212> TYPE: PRT
<213> ORGANISM: Homo sapiens

<400> SEQUENCE: 15

Ile Lys Lys Leu Gln Ala Gln Gln Glu His Val Arg
1               5                   10

<210> SEQ ID NO 16
<211> LENGTH: 15
<212> TYPE: PRT
<213> ORGANISM: Homo sapiens

<400> SEQUENCE: 16

Ser Lys Asn Ile Leu Phe Val Ile Asn Lys Pro Asp Val Phe Lys
1               5                   10                  15

<210> SEQ ID NO 17
<211> LENGTH: 4
<212> TYPE: PRT
<213> ORGANISM: Homo sapiens

<400> SEQUENCE: 17

Leu Gly Leu Lys
1
```

```
<210> SEQ ID NO 18
<211> LENGTH: 5
<212> TYPE: PRT
<213> ORGANISM: Homo sapiens

<400> SEQUENCE: 18

Val Cys Ile Arg Lys
1               5

<210> SEQ ID NO 19
<211> LENGTH: 31
<212> TYPE: PRT
<213> ORGANISM: Homo sapiens

<400> SEQUENCE: 19

Asp Asp Gly Thr Val Ile His Phe Asn Asn Pro Lys Val Gln Thr Ser
1               5                   10                  15

Val Pro Ala Asn Thr Phe Ser Val Thr Gly Ser Ala Asp Asn Lys
            20                  25                  30

<210> SEQ ID NO 20
<211> LENGTH: 16
<212> TYPE: PRT
<213> ORGANISM: Homo sapiens

<400> SEQUENCE: 20

Lys Ser Lys Asn Ile Leu Phe Val Ile Asn Lys Pro Asp Val Phe Lys
1               5                   10                  15

<210> SEQ ID NO 21
<211> LENGTH: 8
<212> TYPE: PRT
<213> ORGANISM: Homo sapiens

<400> SEQUENCE: 21

Ile Gly Gly Lys Gly Thr Pro Arg
1               5

<210> SEQ ID NO 22
<211> LENGTH: 6
<212> TYPE: PRT
<213> ORGANISM: Homo sapiens

<400> SEQUENCE: 22

Leu Gly Pro Asp Gly Lys
1               5

<210> SEQ ID NO 23
<211> LENGTH: 23
<212> TYPE: PRT
<213> ORGANISM: Homo sapiens

<400> SEQUENCE: 23

Gln Ile Thr Glu Met Leu Pro Gly Ile Leu Asn Gln Leu Gly Pro Glu
1               5                   10                  15

Ser Leu Thr His Leu Lys Lys
            20

<210> SEQ ID NO 24
<211> LENGTH: 7
<212> TYPE: PRT
<213> ORGANISM: Homo sapiens
```

```
<400> SEQUENCE: 24

Gln Val Thr Gly Val Ser Arg
1               5

<210> SEQ ID NO 25
<211> LENGTH: 8
<212> TYPE: PRT
<213> ORGANISM: Homo sapiens

<400> SEQUENCE: 25

Met Thr Gly Ser Thr Glu Thr Arg
1               5

<210> SEQ ID NO 26
<211> LENGTH: 7
<212> TYPE: PRT
<213> ORGANISM: Homo sapiens

<400> SEQUENCE: 26

Ala Ile Ala Glu Arg Ile Lys
1               5

<210> SEQ ID NO 27
<211> LENGTH: 13
<212> TYPE: PRT
<213> ORGANISM: Homo sapiens

<400> SEQUENCE: 27

Met Thr Gly Ser Thr Glu Thr Arg Gln Lys Glu Val Lys
1               5                   10

<210> SEQ ID NO 28
<211> LENGTH: 5
<212> TYPE: PRT
<213> ORGANISM: Homo sapiens

<400> SEQUENCE: 28

Asn Lys Ala Ile Arg
1               5

<210> SEQ ID NO 29
<211> LENGTH: 6
<212> TYPE: PRT
<213> ORGANISM: Homo sapiens

<400> SEQUENCE: 29

Gln Ala Lys Gln Ser Arg
1               5

<210> SEQ ID NO 30
<211> LENGTH: 4
<212> TYPE: PRT
<213> ORGANISM: Homo sapiens

<400> SEQUENCE: 30

Ile Gly Gly Lys
1

<210> SEQ ID NO 31
<211> LENGTH: 11
<212> TYPE: PRT
<213> ORGANISM: Homo sapiens

<400> SEQUENCE: 31
```

```
Ser Glu Lys Lys Ala Arg Lys Leu Phe Ser Lys
1               5                   10
```

<210> SEQ ID NO 32
<211> LENGTH: 8
<212> TYPE: PRT
<213> ORGANISM: Homo sapiens

<400> SEQUENCE: 32

```
Lys Leu Ala Asn Asn Val Thr Lys
1               5
```

<210> SEQ ID NO 33
<211> LENGTH: 13
<212> TYPE: PRT
<213> ORGANISM: Homo sapiens

<400> SEQUENCE: 33

```
Asn Ile Leu Phe Val Ile Asn Lys Pro Asp Val Phe Lys
1               5                   10
```

<210> SEQ ID NO 34
<211> LENGTH: 11
<212> TYPE: PRT
<213> ORGANISM: Homo sapiens

<400> SEQUENCE: 34

```
Leu Gly Leu Lys Gln Val Thr Gly Val Ser Arg
1               5                   10
```

<210> SEQ ID NO 35
<211> LENGTH: 5
<212> TYPE: PRT
<213> ORGANISM: Homo sapiens

<400> SEQUENCE: 35

```
Lys Leu Phe Ser Lys
1               5
```

<210> SEQ ID NO 36
<211> LENGTH: 9
<212> TYPE: PRT
<213> ORGANISM: Homo sapiens

<400> SEQUENCE: 36

```
Lys Leu Phe Ser Lys Leu Gly Leu Lys
1               5
```

<210> SEQ ID NO 37
<211> LENGTH: 4
<212> TYPE: PRT
<213> ORGANISM: Homo sapiens

<400> SEQUENCE: 37

```
Asn Glu Thr Lys
1
```

<210> SEQ ID NO 38
<211> LENGTH: 34
<212> TYPE: PRT
<213> ORGANISM: Homo sapiens

<400> SEQUENCE: 38

```
Ser Pro Gly Ser Asp Thr Tyr Ile Ile Phe Gly Glu Ala Lys Ile Glu
1               5                   10                  15
```

Asp Leu Thr Gln His Ala Gln Met Ser Ala Ile Glu Asn Leu Lys Pro
            20                  25                  30

Thr Arg

<210> SEQ ID NO 39
<211> LENGTH: 10
<212> TYPE: PRT
<213> ORGANISM: Homo sapiens

<400> SEQUENCE: 39

Met Met Asp Ser Lys Ala Ile Ala Glu Arg
1               5                   10

<210> SEQ ID NO 40
<211> LENGTH: 6
<212> TYPE: PRT
<213> ORGANISM: Homo sapiens

<400> SEQUENCE: 40

Lys Lys Val Ile His Lys
1               5

<210> SEQ ID NO 41
<211> LENGTH: 13
<212> TYPE: PRT
<213> ORGANISM: Homo sapiens

<400> SEQUENCE: 41

Val Ala Glu Ala Ala Gly Leu Gly Asp His Ile Asp Lys
1               5                   10

<210> SEQ ID NO 42
<211> LENGTH: 19
<212> TYPE: PRT
<213> ORGANISM: Homo sapiens

<400> SEQUENCE: 42

Val Gln Thr Ser Val Pro Ala Asn Thr Phe Ser Val Thr Gly Ser Ala
1               5                   10                  15

Asp Asn Lys

<210> SEQ ID NO 43
<211> LENGTH: 13
<212> TYPE: PRT
<213> ORGANISM: Homo sapiens

<400> SEQUENCE: 43

Leu Ala Asn Asn Val Thr Lys Leu Gly Pro Asp Gly Lys
1               5                   10

<210> SEQ ID NO 44
<211> LENGTH: 12
<212> TYPE: PRT
<213> ORGANISM: Homo sapiens

<400> SEQUENCE: 44

Met Met Asp Ser Lys Ala Ile Ala Glu Arg Ile Lys
1               5                   10

<210> SEQ ID NO 45
<211> LENGTH: 10
<212> TYPE: PRT
<213> ORGANISM: Homo sapiens

```
<400> SEQUENCE: 45

Gln Ser Arg Ser Glu Lys Lys Ala Arg Lys
1               5                   10

<210> SEQ ID NO 46
<211> LENGTH: 13
<212> TYPE: PRT
<213> ORGANISM: Homo sapiens

<400> SEQUENCE: 46

Asp Ile Glu Leu Val Ile Ser Gln Ala Asn Thr Thr Arg
1               5                   10

<210> SEQ ID NO 47
<211> LENGTH: 18
<212> TYPE: PRT
<213> ORGANISM: Homo sapiens

<400> SEQUENCE: 47

Gly Glu Asp Glu Asp Val Pro Glu Leu Val Gly Asp Phe Asp Ala Ala
1               5                   10                  15

Ser Lys

<210> SEQ ID NO 48
<211> LENGTH: 14
<212> TYPE: PRT
<213> ORGANISM: Homo sapiens

<400> SEQUENCE: 48

Gln Val Thr Gly Val Ser Arg Val Cys Ile Arg Lys Ser Lys
1               5                   10

<210> SEQ ID NO 49
<211> LENGTH: 10
<212> TYPE: PRT
<213> ORGANISM: Homo sapiens

<400> SEQUENCE: 49

Met Thr Gly Ser Thr Glu Thr Arg Gln Lys
1               5                   10

<210> SEQ ID NO 50
<211> LENGTH: 15
<212> TYPE: PRT
<213> ORGANISM: Homo sapiens

<400> SEQUENCE: 50

Glu Ala Asp Asn Asp Ile Val Asn Ala Ile Met Ser Leu Thr Met
1               5                   10                  15

<210> SEQ ID NO 51
<211> LENGTH: 8
<212> TYPE: PRT
<213> ORGANISM: Homo sapiens

<400> SEQUENCE: 51

Leu Phe Ser Lys Leu Gly Leu Lys
1               5

<210> SEQ ID NO 52
<211> LENGTH: 4
<212> TYPE: PRT
<213> ORGANISM: Homo sapiens
```

<400> SEQUENCE: 52

Gly Thr Pro Arg
1

<210> SEQ ID NO 53
<211> LENGTH: 8
<212> TYPE: PRT
<213> ORGANISM: Homo sapiens

<400> SEQUENCE: 53

Asn Glu Thr Lys Ala Asp Glu Gln
1               5

<210> SEQ ID NO 54
<211> LENGTH: 4
<212> TYPE: PRT
<213> ORGANISM: Homo sapiens

<400> SEQUENCE: 54

Ser Glu Lys Lys
1

<210> SEQ ID NO 55
<211> LENGTH: 7
<212> TYPE: PRT
<213> ORGANISM: Homo sapiens

<400> SEQUENCE: 55

Val Cys Ile Arg Lys Ser Lys
1               5

<210> SEQ ID NO 56
<211> LENGTH: 14
<212> TYPE: PRT
<213> ORGANISM: Homo sapiens

<400> SEQUENCE: 56

Thr Ala Ala Ala Asp Lys Lys Leu Gln Ser Asn Leu Lys
1               5                   10

<210> SEQ ID NO 57
<211> LENGTH: 24
<212> TYPE: PRT
<213> ORGANISM: Homo sapiens

<400> SEQUENCE: 57

Leu Gly Pro Asp Gly Lys Gly Glu Asp Glu Asp Val Pro Glu Leu Val
1               5                   10                  15

Gly Asp Phe Asp Ala Ala Ser Lys
            20

<210> SEQ ID NO 58
<211> LENGTH: 13
<212> TYPE: PRT
<213> ORGANISM: Homo sapiens

<400> SEQUENCE: 58

Leu Ile Gly Glu Glu Leu Ala Gln Leu Lys Glu Gln Arg
1               5                   10

<210> SEQ ID NO 59
<211> LENGTH: 8
<212> TYPE: PRT

```
<213> ORGANISM: Homo sapiens

<400> SEQUENCE: 59

Val His Lys Thr Asp Leu Glu Arg
1               5

<210> SEQ ID NO 60
<211> LENGTH: 20
<212> TYPE: PRT
<213> ORGANISM: Homo sapiens

<400> SEQUENCE: 60

Asn Ile Ser Gln Asp Met Thr Gln Thr Ser Gly Thr Asn Leu Thr Ser
1               5                   10                  15

Glu Glu Leu Arg
            20

<210> SEQ ID NO 61
<211> LENGTH: 4
<212> TYPE: PRT
<213> ORGANISM: Homo sapiens

<400> SEQUENCE: 61

Asn Asp Leu Lys
1

<210> SEQ ID NO 62
<211> LENGTH: 9
<212> TYPE: PRT
<213> ORGANISM: Homo sapiens

<400> SEQUENCE: 62

Asn Asp Leu Lys Thr Glu Gly Lys Lys
1               5

<210> SEQ ID NO 63
<211> LENGTH: 5
<212> TYPE: PRT
<213> ORGANISM: Homo sapiens

<400> SEQUENCE: 63

Thr Glu Gly Lys Lys
1               5

<210> SEQ ID NO 64
<211> LENGTH: 12
<212> TYPE: PRT
<213> ORGANISM: Homo sapiens

<400> SEQUENCE: 64

Met Ala Glu Gly Gly Val Thr Ser Glu Asp Tyr Arg
1               5                   10

<210> SEQ ID NO 65
<211> LENGTH: 18
<212> TYPE: PRT
<213> ORGANISM: Homo sapiens

<400> SEQUENCE: 65

Val Gln Gln Met His Arg Pro Lys Leu Ile Gly Glu Glu Leu Ala Gln
1               5                   10                  15

Leu Lys
```

-continued

```
<210> SEQ ID NO 66
<211> LENGTH: 5
<212> TYPE: PRT
<213> ORGANISM: Homo sapiens

<400> SEQUENCE: 66

Thr Asp Leu Glu Arg
1               5

<210> SEQ ID NO 67
<211> LENGTH: 6
<212> TYPE: PRT
<213> ORGANISM: Homo sapiens

<400> SEQUENCE: 67

Glu Gln Arg Val His Lys
1               5

<210> SEQ ID NO 68
<211> LENGTH: 16
<212> TYPE: PRT
<213> ORGANISM: Homo sapiens

<400> SEQUENCE: 68

Leu Ile Gly Glu Glu Leu Ala Gln Leu Lys Glu Gln Arg Val His Lys
1               5                   10                  15

<210> SEQ ID NO 69
<211> LENGTH: 11
<212> TYPE: PRT
<213> ORGANISM: Homo sapiens

<400> SEQUENCE: 69

Glu Gln Arg Val His Lys Thr Asp Leu Glu Arg
1               5                   10

<210> SEQ ID NO 70
<211> LENGTH: 6
<212> TYPE: PRT
<213> ORGANISM: Homo sapiens

<400> SEQUENCE: 70

Glu Ala Tyr Phe Glu Lys
1               5

<210> SEQ ID NO 71
<211> LENGTH: 10
<212> TYPE: PRT
<213> ORGANISM: Homo sapiens

<400> SEQUENCE: 71

Glu Ala Tyr Phe Glu Lys Gln Gln Gln Lys
1               5                   10

<210> SEQ ID NO 72
<211> LENGTH: 11
<212> TYPE: PRT
<213> ORGANISM: Homo sapiens

<400> SEQUENCE: 72

Ala Ile Gln Leu Ser Met Gln Gly Ser Ser Arg
1               5                   10

<210> SEQ ID NO 73
<211> LENGTH: 22
```

<212> TYPE: PRT
<213> ORGANISM: Homo sapiens

<400> SEQUENCE: 73

Asn Ile Ser Gln Asp Met Thr Gln Thr Ser Gly Thr Asn Leu Thr Ser
1               5                   10                  15

Glu Glu Leu Arg Lys Arg
            20

<210> SEQ ID NO 74
<211> LENGTH: 20
<212> TYPE: PRT
<213> ORGANISM: Homo sapiens

<400> SEQUENCE: 74

Thr Val Glu Glu Asp Glu Asn Glu Asp Val Glu Glu Asp Ser Thr Gly
1               5                   10                  15

Ile Glu Glu Lys
            20

<210> SEQ ID NO 75
<211> LENGTH: 11
<212> TYPE: PRT
<213> ORGANISM: Homo sapiens

<400> SEQUENCE: 75

Arg Glu Ala Tyr Phe Glu Lys Gln Gln Gln Lys
1               5                   10

<210> SEQ ID NO 76
<211> LENGTH: 29
<212> TYPE: PRT
<213> ORGANISM: Homo sapiens

<400> SEQUENCE: 76

Asn Ile Ser Gln Asp Met Thr Gln Thr Ser Gly Thr Asn Leu Thr Ser
1               5                   10                  15

Glu Glu Leu Arg Lys Arg Arg Glu Ala Tyr Phe Glu Lys
            20                  25

<210> SEQ ID NO 77
<211> LENGTH: 21
<212> TYPE: PRT
<213> ORGANISM: Homo sapiens

<400> SEQUENCE: 77

Asn Ile Ser Gln Asp Met Thr Gln Thr Ser Gly Thr Asn Leu Thr Ser
1               5                   10                  15

Glu Glu Leu Arg Lys
            20

<210> SEQ ID NO 78
<211> LENGTH: 13
<212> TYPE: PRT
<213> ORGANISM: Homo sapiens

<400> SEQUENCE: 78

Lys Arg Arg Glu Ala Tyr Phe Glu Lys Gln Gln Gln Lys
1               5                   10

<210> SEQ ID NO 79
<211> LENGTH: 25
<212> TYPE: PRT

-continued

<213> ORGANISM: Homo sapiens

<400> SEQUENCE: 79

Ser Tyr Tyr His His His His His Leu Glu Asn Leu Tyr Phe Gln
1               5                   10                  15

Gly Met Glu Ser Ile Phe His Glu Lys
            20                  25

<210> SEQ ID NO 80
<211> LENGTH: 20
<212> TYPE: PRT
<213> ORGANISM: Homo sapiens

<400> SEQUENCE: 80

Val Leu Glu Ala Asn Asp Gly Ser Gly Met Leu Asp Glu Asp Glu
1               5                   10                  15

Asp Leu Gln Arg
            20

<210> SEQ ID NO 81
<211> LENGTH: 26
<212> TYPE: PRT
<213> ORGANISM: Homo sapiens

<400> SEQUENCE: 81

Thr Phe Leu Gln Gln Pro Ser Gly Asn Met Asp Asp Ser Gly Phe Phe
1               5                   10                  15

Ser Ile Gln Val Ile Ser Asn Ala Leu Lys
            20                  25

<210> SEQ ID NO 82
<211> LENGTH: 26
<212> TYPE: PRT
<213> ORGANISM: Homo sapiens

<400> SEQUENCE: 82

Thr Phe Leu Gln Gln Pro Ser Gly Asn Met Asp Asp Ser Gly Phe Phe
1               5                   10                  15

Ser Ile Gln Val Ile Ser Asn Ala Leu Lys
            20                  25

<210> SEQ ID NO 83
<211> LENGTH: 13
<212> TYPE: PRT
<213> ORGANISM: Homo sapiens

<400> SEQUENCE: 83

Leu Ala Glu Ala Leu Pro Lys Gln Ser Val Asp Gly Lys
1               5                   10

<210> SEQ ID NO 84
<211> LENGTH: 11
<212> TYPE: PRT
<213> ORGANISM: Homo sapiens

<400> SEQUENCE: 84

Glu Thr Ile Met Asn Gln Glu Lys Leu Ala Lys
1               5                   10

<210> SEQ ID NO 85
<211> LENGTH: 5
<212> TYPE: PRT
<213> ORGANISM: Homo sapiens

```
<400> SEQUENCE: 85

Lys Val Val His Arg
1               5

<210> SEQ ID NO 86
<211> LENGTH: 42
<212> TYPE: PRT
<213> ORGANISM: Homo sapiens

<400> SEQUENCE: 86

Leu Ala Glu Ala Leu Pro Lys Gln Ser Val Asp Gly Lys Ala Pro Leu
1               5                   10                  15

Ala Thr Gly Glu Asp Asp Asp Asp Glu Val Pro Asp Leu Val Glu Asn
                20                  25                  30

Phe Asp Glu Ala Ser Lys Asn Glu Ala Asn
            35                  40

<210> SEQ ID NO 87
<211> LENGTH: 5
<212> TYPE: PRT
<213> ORGANISM: Homo sapiens

<400> SEQUENCE: 87

Ala Lys Gln Ser Arg
1               5

<210> SEQ ID NO 88
<211> LENGTH: 9
<212> TYPE: PRT
<213> ORGANISM: Homo sapiens

<400> SEQUENCE: 88

Lys Ala Met Ser Lys Leu Gly Leu Arg
1               5

<210> SEQ ID NO 89
<211> LENGTH: 7
<212> TYPE: PRT
<213> ORGANISM: Homo sapiens

<400> SEQUENCE: 89

Thr Ala Thr Ala Asp Asp Lys
1               5

<210> SEQ ID NO 90
<211> LENGTH: 6
<212> TYPE: PRT
<213> ORGANISM: Homo sapiens

<400> SEQUENCE: 90

Lys Lys Val Val His Arg
1               5

<210> SEQ ID NO 91
<211> LENGTH: 8
<212> TYPE: PRT
<213> ORGANISM: Homo sapiens

<400> SEQUENCE: 91

Ile Gly Gly Lys Gly Thr Ala Arg
1               5
```

```
<210> SEQ ID NO 92
<211> LENGTH: 29
<212> TYPE: PRT
<213> ORGANISM: Homo sapiens

<400> SEQUENCE: 92

Ala Pro Leu Ala Thr Gly Glu Asp Asp Asp Glu Val Pro Asp Leu
1               5                   10                  15

Val Glu Asn Phe Asp Glu Ala Ser Lys Asn Glu Ala Asn
            20                  25

<210> SEQ ID NO 93
<211> LENGTH: 6
<212> TYPE: PRT
<213> ORGANISM: Homo sapiens

<400> SEQUENCE: 93

Met Asp Ala Glu Phe Arg
1               5

<210> SEQ ID NO 94
<211> LENGTH: 8
<212> TYPE: PRT
<213> ORGANISM: Homo sapiens

<400> SEQUENCE: 94

Thr Ala Thr Ala Asp Asp Lys Lys
1               5

<210> SEQ ID NO 95
<211> LENGTH: 14
<212> TYPE: PRT
<213> ORGANISM: Homo sapiens

<400> SEQUENCE: 95

Thr Ala Thr Ala Asp Asp Lys Lys Leu Gln Phe Ser Leu Lys
1               5                   10

<210> SEQ ID NO 96
<211> LENGTH: 16
<212> TYPE: PRT
<213> ORGANISM: Homo sapiens

<400> SEQUENCE: 96

Lys Ser Lys Asn Ile Leu Phe Val Ile Thr Lys Pro Asp Val Tyr Lys
1               5                   10                  15

<210> SEQ ID NO 97
<211> LENGTH: 7
<212> TYPE: PRT
<213> ORGANISM: Homo sapiens

<400> SEQUENCE: 97

Lys Leu Gln Phe Ser Leu Lys
1               5

<210> SEQ ID NO 98
<211> LENGTH: 5
<212> TYPE: PRT
<213> ORGANISM: Homo sapiens

<400> SEQUENCE: 98

Ala Lys Ala Val Arg
1               5
```

<210> SEQ ID NO 99
<211> LENGTH: 6
<212> TYPE: PRT
<213> ORGANISM: Homo sapiens

<400> SEQUENCE: 99

Leu Gln Phe Ser Leu Lys
1               5

<210> SEQ ID NO 100
<211> LENGTH: 7
<212> TYPE: PRT
<213> ORGANISM: Homo sapiens

<400> SEQUENCE: 100

Leu Gln Phe Ser Leu Lys Lys
1               5

<210> SEQ ID NO 101
<211> LENGTH: 5
<212> TYPE: PRT
<213> ORGANISM: Homo sapiens

<400> SEQUENCE: 101

Lys Ala Met Ser Lys
1               5

<210> SEQ ID NO 102
<211> LENGTH: 25
<212> TYPE: PRT
<213> ORGANISM: Homo sapiens

<400> SEQUENCE: 102

Ala Pro Leu Ala Thr Gly Glu Asp Asp Asp Glu Val Pro Asp Leu
1               5                   10                  15

Val Glu Asn Phe Asp Glu Ala Ser Lys
            20                  25

<210> SEQ ID NO 103
<211> LENGTH: 21
<212> TYPE: PRT
<213> ORGANISM: Homo sapiens

<400> SEQUENCE: 103

Leu Ile Gly Glu Glu Leu Ala Gln Leu Lys Glu Gln Arg Val His Lys
1               5                   10                  15

Thr Asp Leu Glu Arg
            20

<210> SEQ ID NO 104
<211> LENGTH: 4
<212> TYPE: PRT
<213> ORGANISM: Homo sapiens

<400> SEQUENCE: 104

Gln Gln Gln Lys
1

<210> SEQ ID NO 105
<211> LENGTH: 8
<212> TYPE: PRT
<213> ORGANISM: Homo sapiens

<400> SEQUENCE: 105

```
Val Gln Gln Met His Arg Pro Lys
1               5

<210> SEQ ID NO 106
<211> LENGTH: 6
<212> TYPE: PRT
<213> ORGANISM: Homo sapiens

<400> SEQUENCE: 106

Ser Glu Lys Lys Ala Arg
1               5

<210> SEQ ID NO 107
<211> LENGTH: 16
<212> TYPE: PRT
<213> ORGANISM: Homo sapiens

<400> SEQUENCE: 107

Leu Ser Val Thr Asn Ile Pro Gly Ile Glu Glu Val Asn Met Ile Lys
1               5                   10                  15

<210> SEQ ID NO 108
<211> LENGTH: 5
<212> TYPE: PRT
<213> ORGANISM: Homo sapiens

<400> SEQUENCE: 108

Met Met Asp Ser Lys
1               5

<210> SEQ ID NO 109
<211> LENGTH: 4
<212> TYPE: PRT
<213> ORGANISM: Homo sapiens

<400> SEQUENCE: 109

Arg Lys Lys Lys
1
```